(12) United States Patent
Tagge et al.

(10) Patent No.: US 10,039,563 B2
(45) Date of Patent: Aug. 7, 2018

(54) SUTURER

(71) Applicant: Invictus Medical Innovations, LLC, Salt Lake City, UT (US)

(72) Inventors: Bryan C. Tagge, Salt Lake City, UT (US); Adam Liberatore, Logan, UT (US); Daniel Gerbec, Logan, UT (US); James Robbins, North Logan, UT (US)

(73) Assignee: INVICTUS MEDICAL INNOVATIONS, LLC, Salt Lake City, UT (US)

( * ) Notice: Subject to any disclaimer, the term of this patent is extended or adjusted under 35 U.S.C. 154(b) by 331 days.

(21) Appl. No.: 14/214,029

(22) Filed: Mar. 14, 2014

(65) Prior Publication Data

US 2014/0276988 A1 Sep. 18, 2014

Related U.S. Application Data

(60) Provisional application No. 61/794,746, filed on Mar. 15, 2013, provisional application No. 61/883,079, filed on Sep. 26, 2013, provisional application No. 61/952,042, filed on Mar. 12, 2014.

(51) Int. Cl.
| | |
|---|---|
| *A61B 17/04* | (2006.01) |
| *A61B 17/062* | (2006.01) |
| *A61B 17/24* | (2006.01) |
| *A61B 17/06* | (2006.01) |
| *A61B 17/00* | (2006.01) |

(52) U.S. Cl.
CPC .......... *A61B 17/24* (2013.01); *A61B 17/0491* (2013.01); *A61B 17/0625* (2013.01); *A61B 17/06114* (2013.01); *A61B 17/06161* (2013.01); *A61B 17/0469* (2013.01); *A61B 17/0482* (2013.01); *A61B 17/062* (2013.01); *A61B 2017/0053* (2013.01); *A61B 2017/0609* (2013.01); *A61B 2017/06047* (2013.01)

(58) Field of Classification Search
CPC . A61B 17/0469; A61B 17/0482; A61B 17/04; A61B 17/0491; A61B 17/062; A61B 17/0625; A61B 17/0483; A61B 2017/0609; A61B 2017/047; A61B 17/24
See application file for complete search history.

(56) References Cited

U.S. PATENT DOCUMENTS

| | | | |
|---|---|---|---|
| 1,037,864 | A | 9/1912 | Carlson et al. |
| 1,352,508 | A | 9/1920 | Ftacek |
| 2,516,710 | A | 7/1950 | Mascolo |

(Continued)

FOREIGN PATENT DOCUMENTS

RU 2 076 639 C1 4/1997

OTHER PUBLICATIONS

International Search Report dated Aug. 14, 2014 as received in Application No. PCT/US2014/030664.

(Continued)

*Primary Examiner* — Christopher L Templeton
(74) *Attorney, Agent, or Firm* — Maschoff Brennan

(57) ABSTRACT

A suturer may include a base mechanism. The base mechanism may include a first arm having a first driving member. The base mechanism may include a second arm having a second driving member. The suturer may be configured to selectively pass a needle from an enclosed position within the first arm to an enclosed position within the second arm.

12 Claims, 47 Drawing Sheets

(56) References Cited

U.S. PATENT DOCUMENTS

| | | | |
|---|---|---|---|
| 2,601,564 A | 6/1952 | Smith | |
| 3,901,244 A | 8/1975 | Schweizer | |
| 4,236,470 A | 12/1980 | Stenson | |
| 4,345,601 A | 8/1982 | Fukuda | |
| 4,873,976 A | 10/1989 | Schreiber | |
| 5,037,021 A | 8/1991 | Mills et al. | |
| 5,080,663 A | 1/1992 | Mills et al. | |
| 5,364,408 A | 11/1994 | Gordon | |
| 5,389,103 A | 2/1995 | Melzer et al. | |
| 5,458,609 A | 10/1995 | Gordon et al. | |
| 5,474,571 A | 12/1995 | Lang | |
| 5,478,344 A | 12/1995 | Stone et al. | |
| 5,484,451 A | 2/1996 | Akopov et al. | |
| 5,503,638 A * | 4/1996 | Cooper | A61B 17/07207 606/148 |
| 5,520,700 A | 5/1996 | Beyar et al. | |
| 5,540,240 A | 7/1996 | Bauer | |
| 5,540,704 A | 7/1996 | Gordon et al. | |
| 5,569,301 A | 10/1996 | Granger et al. | |
| 5,571,090 A | 11/1996 | Sherts | |
| 5,571,119 A | 11/1996 | Atala | |
| 5,603,718 A | 2/1997 | Xu | |
| 5,618,290 A | 4/1997 | Toy | |
| 5,632,751 A | 5/1997 | Piraka | |
| 5,645,552 A | 7/1997 | Sherts | |
| 5,674,229 A * | 10/1997 | Tovey | A61B 17/0469 606/139 |
| 5,674,230 A * | 10/1997 | Tovey | A61B 17/0469 606/139 |
| 5,690,652 A | 11/1997 | Wurster et al. | |
| 5,690,653 A | 11/1997 | Richardson et al. | |
| 5,693,071 A * | 12/1997 | Gorecki | A61B 17/0469 606/222 |
| 5,735,862 A | 4/1998 | Jennings et al. | |
| 5,759,188 A | 6/1998 | Yoon | |
| 5,769,892 A * | 6/1998 | Kingwell | A61B 17/07292 227/178.1 |
| 5,810,855 A * | 9/1998 | Rayburn | A61B 17/07207 227/176.1 |
| 5,814,054 A | 9/1998 | Kortenbach et al. | |
| 5,814,057 A * | 9/1998 | Oi | A61B 17/072 227/178.1 |
| 5,908,428 A * | 6/1999 | Scirica | A61B 17/0469 206/339 |
| 5,938,668 A | 8/1999 | Scirica et al. | |
| 6,048,351 A | 4/2000 | Gordon et al. | |
| 6,056,771 A | 5/2000 | Proto | |
| 6,099,551 A * | 8/2000 | Gabbay | A61B 17/07207 227/176.1 |
| 6,273,897 B1 * | 8/2001 | Dalessandro | A61B 17/07207 606/139 |
| 6,955,643 B2 | 10/2005 | Gellman et al. | |
| 6,984,237 B2 | 1/2006 | Hatch | |
| 7,166,116 B2 | 1/2007 | Lizardi et al. | |
| 7,442,198 B2 | 10/2008 | Gellman et al. | |
| 7,615,059 B2 | 11/2009 | Watschke et al. | |
| 7,842,050 B2 | 11/2010 | Diduch | |
| 7,862,572 B2 * | 1/2011 | Meade | A61B 17/0482 606/145 |
| 8,088,131 B2 | 1/2012 | Watschke | |
| 8,097,006 B2 | 1/2012 | Prestel et al. | |
| 8,123,762 B2 | 2/2012 | Chu et al. | |
| 8,177,794 B2 | 5/2012 | Cabrera et al. | |
| 8,192,450 B2 | 6/2012 | Gonzales et al. | |
| 9,125,645 B1 * | 9/2015 | Martin | A61B 17/0469 |
| 2003/0023250 A1 | 1/2003 | Watschke et al. | |
| 2003/0233106 A1 | 12/2003 | Dreyfuss | |
| 2005/0222610 A1 | 10/2005 | Melker | |
| 2006/0036232 A1 * | 2/2006 | Primavera | A61B 17/0469 604/411 |
| 2006/0163313 A1 | 7/2006 | Larson | |
| 2007/0293946 A1 | 12/2007 | Gonzales et al. | |
| 2008/0027468 A1 | 1/2008 | Fenton, Jr. et al. | |
| 2009/0012538 A1 * | 1/2009 | Saliman | A61B 17/0491 606/145 |
| 2009/0084389 A1 | 4/2009 | Gonzales | |
| 2009/0209980 A1 * | 8/2009 | Harris | A61B 17/0491 606/144 |
| 2011/0152891 A1 * | 6/2011 | McLawhorn | A61B 17/0625 606/145 |
| 2011/0313433 A1 * | 12/2011 | Woodard, Jr. | A61B 17/0469 606/145 |
| 2012/0150197 A1 * | 6/2012 | Malkowski | A61B 17/0625 606/144 |
| 2012/0277768 A1 * | 11/2012 | Viola | A61B 17/0469 606/145 |
| 2013/0041388 A1 * | 2/2013 | Lane | A61B 17/0467 606/145 |
| 2013/0144315 A1 * | 6/2013 | Hart | A61B 1/00066 606/144 |
| 2013/0245647 A1 * | 9/2013 | Martin | A61B 17/0469 606/147 |

OTHER PUBLICATIONS

Written Opinion of the International Searching Authority dated Aug. 14, 2014 as received in Application No. PCT/US2014/030664.

\* cited by examiner

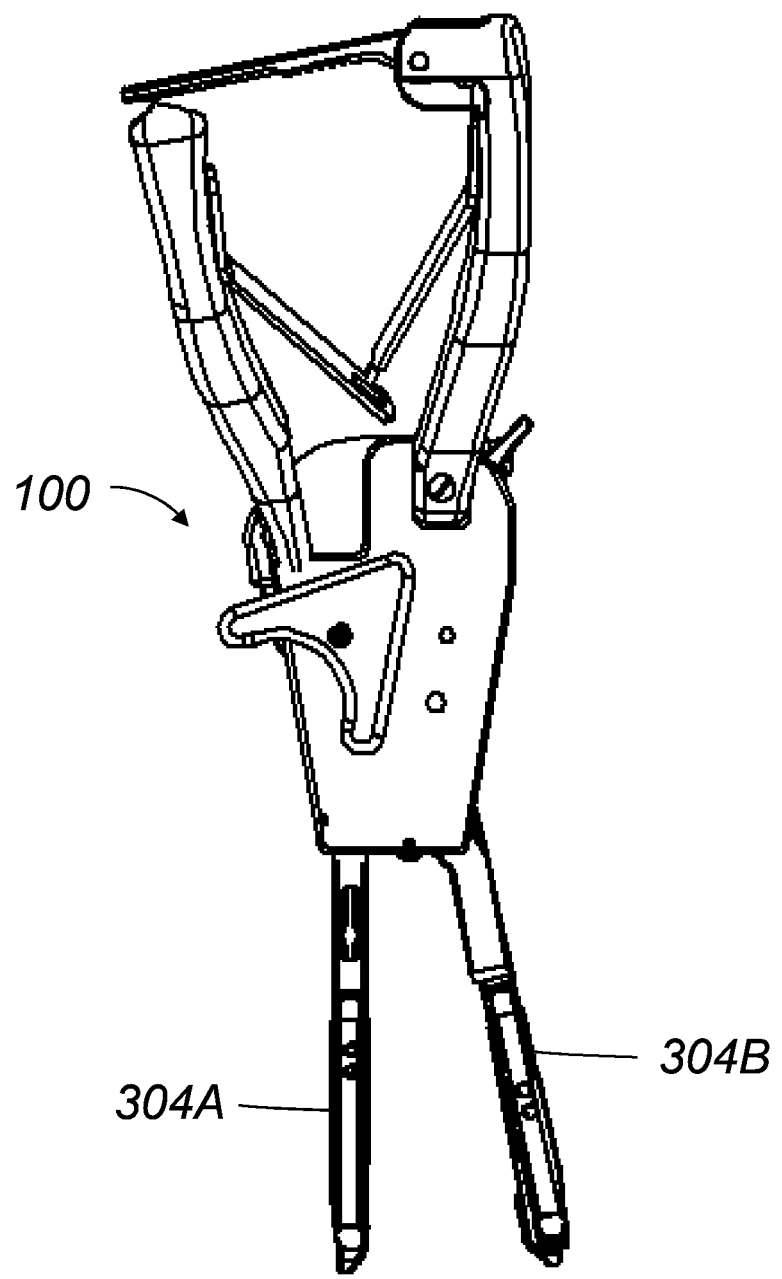
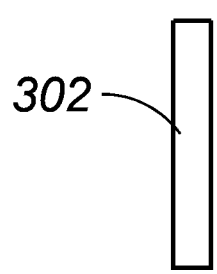
Fig. 3A

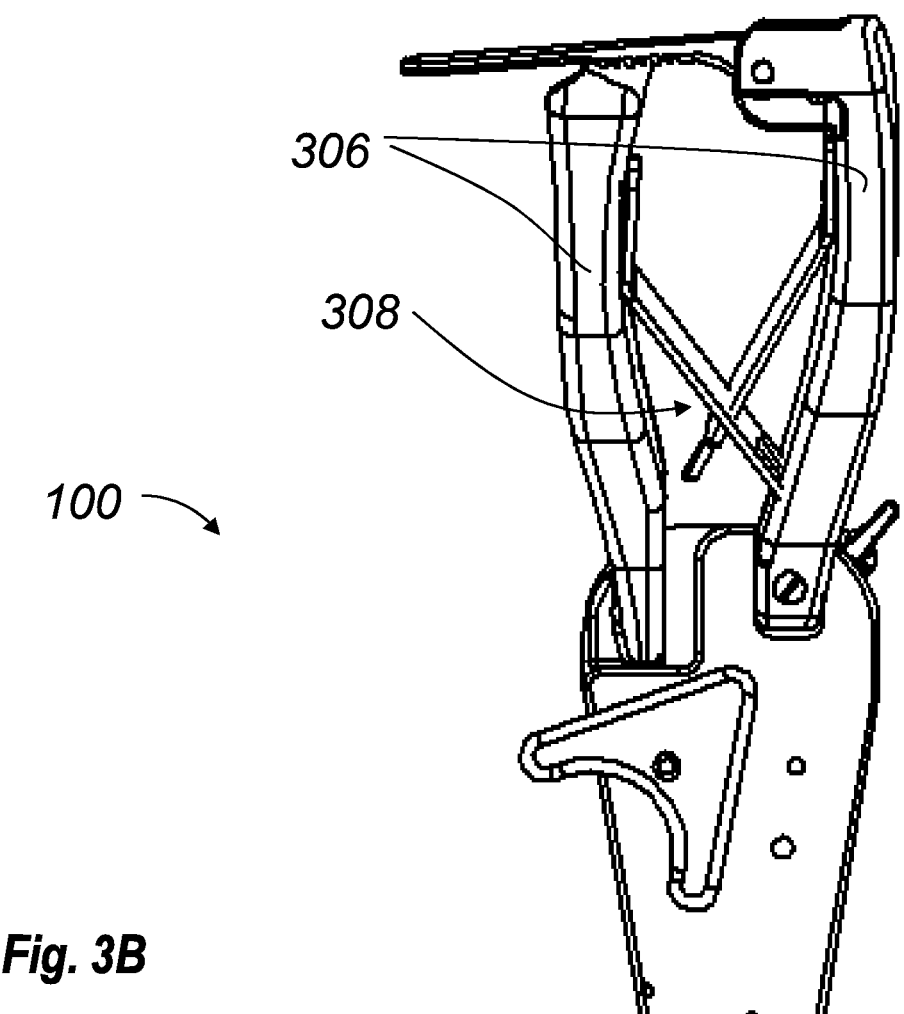
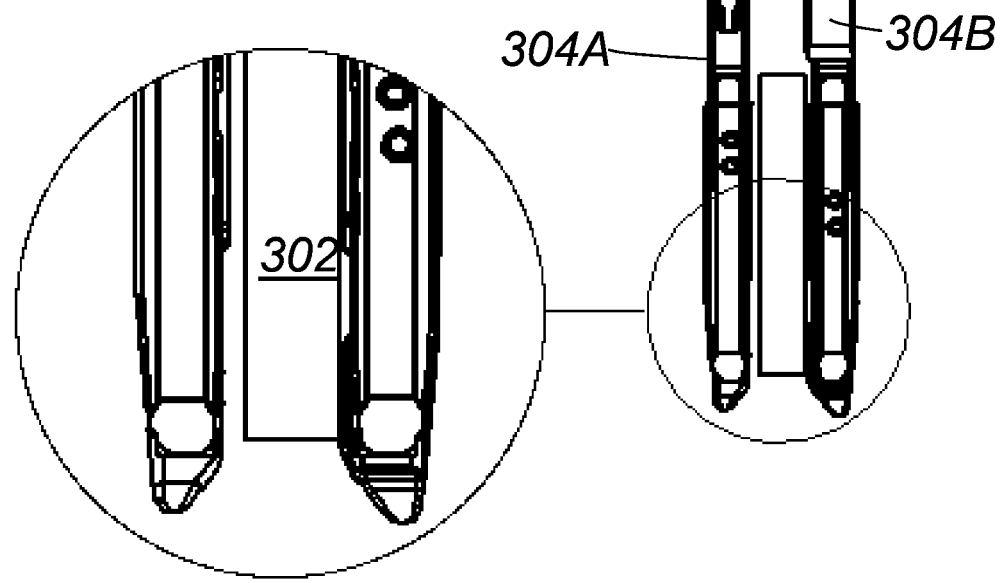
Fig. 3B

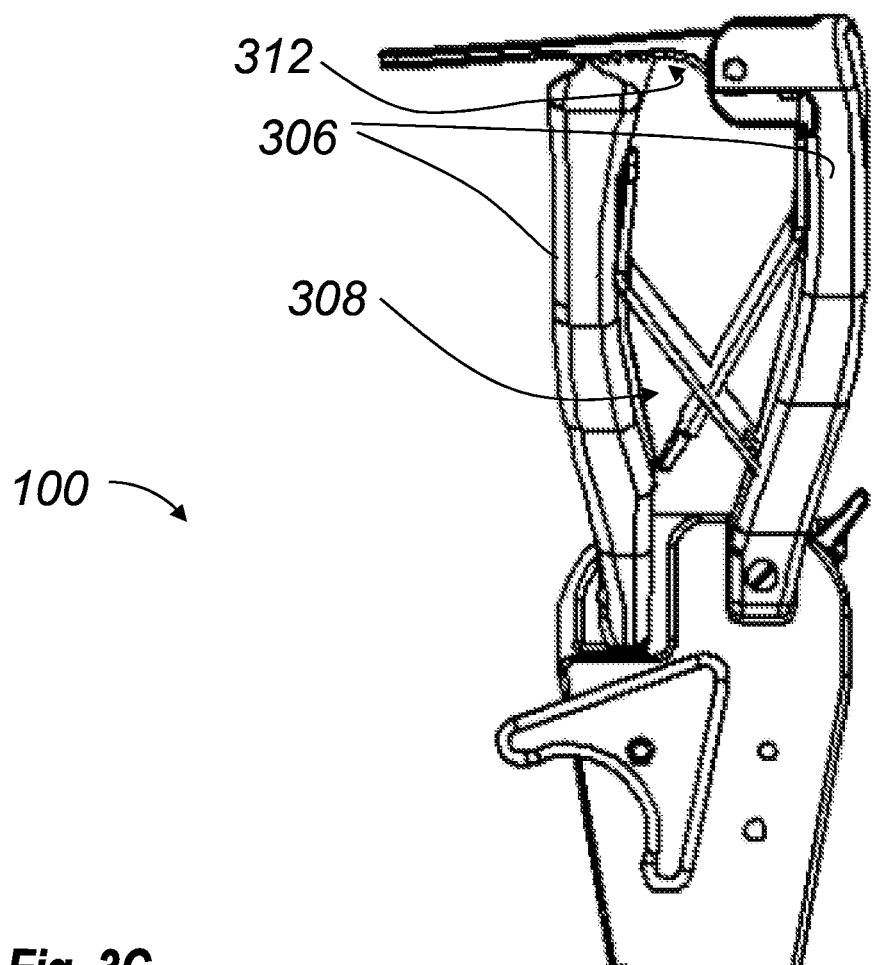
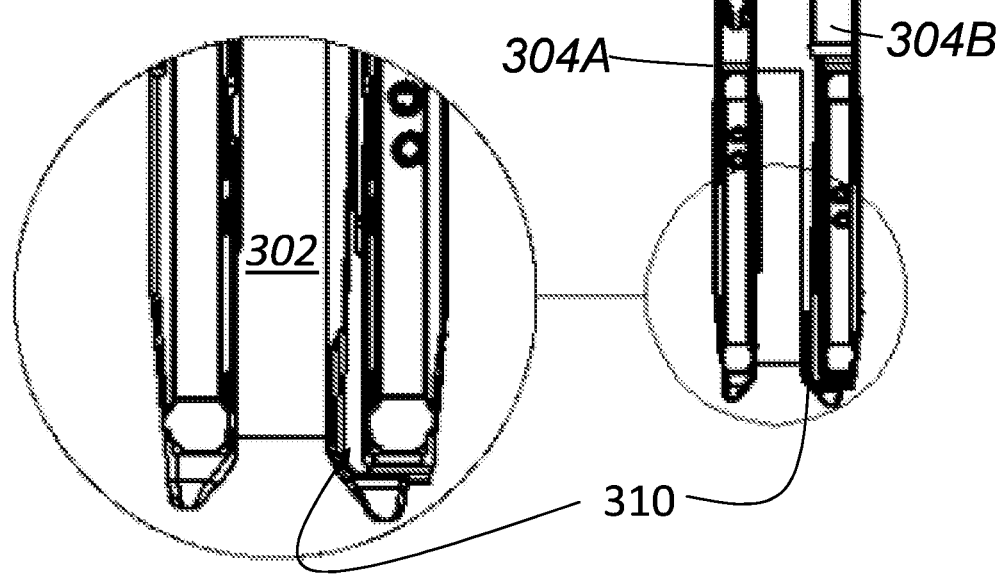
Fig. 3C

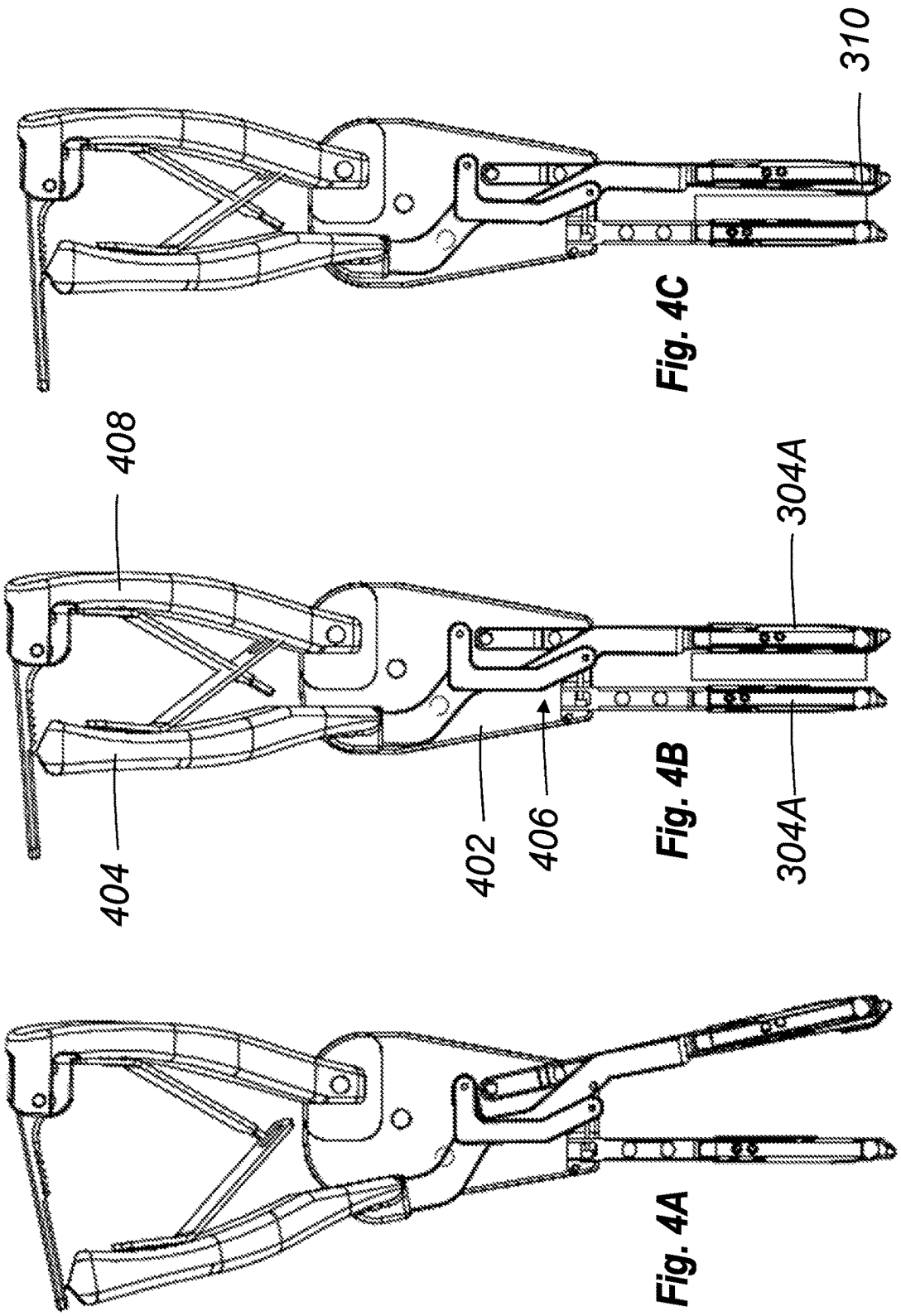

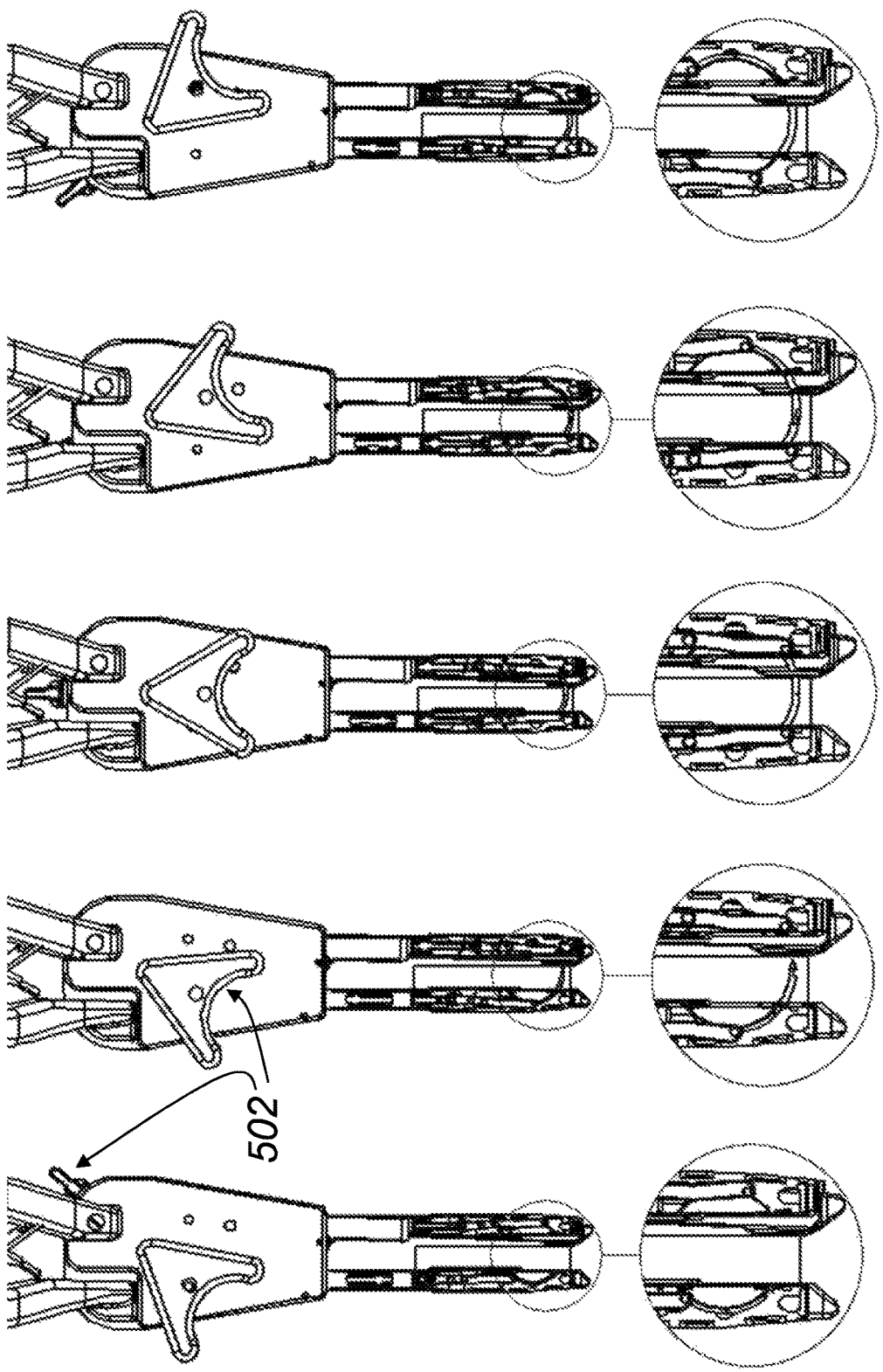

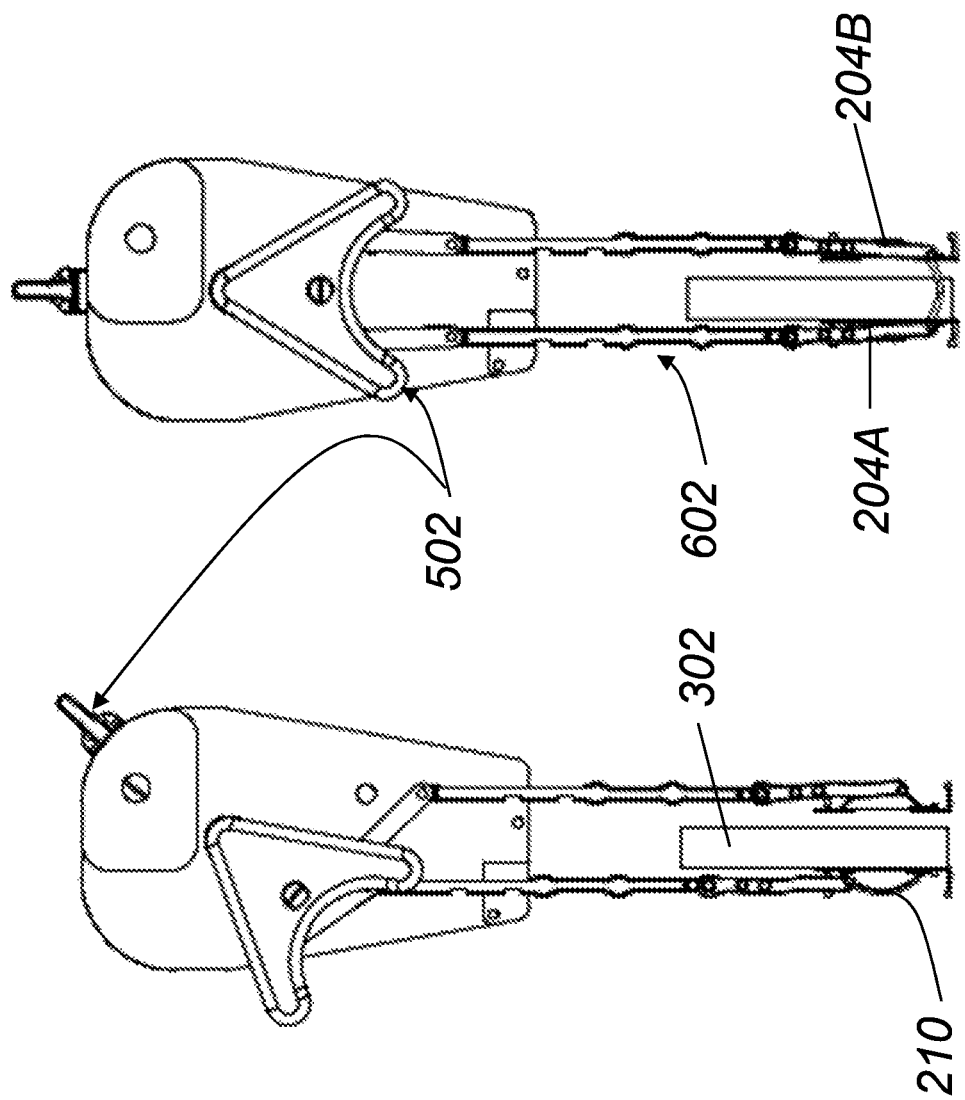

SUTURER

CROSS-REFERENCE TO RELATED APPLICATIONS

This application claims priority to U.S. Provisional Application No. 61/794,746, filed Mar. 15, 2013, titled SUTURE PASSING SYSTEM, to U.S. Provisional Application No. 61/883,079, filed Sep. 26, 2013, titled SUTURING TISSUE, and to U.S. Provisional Application No. 61/952,042, filed Mar. 12, 2014, titled SUTURER, all of which are incorporated herein by reference in their entireties.

BACKGROUND

Field

The embodiments discussed herein relate to suture passing systems and devices.

Relevant Technology

Numerous devices have been developed for the passing of suture through soft tissue or bone. However, many of these suture passers are configured to allow the passing of suture in only one direction. Though this is acceptable in traditional surgeries, laparoscopic/endoscopic procedures as well as other procedures in a more confined space than traditional surgery may benefit from passage of the suture in two or more directions. Several laparoscopic/endoscopic surgical instruments have been produced to allow this two-way passage. However, these instruments do not lend themselves to use in confined anatomical spaces, such as a nasal cavity during medialization of the middle turbinate or during a septoplasty. The exposed needle of conventional laparoscopic/endoscopic suturing devices poses significant risk to the tissue of such a confined anatomical space.

Thus, a manual needle driver is generally used to pass a suture needle from one side of an anatomical wall to the other in the nasal cavity. In such a confined anatomical space, the surgeon is challenged to deliver the needle to the desired location without causing damage to the adjacent tissue. Further, passing the needle through the anatomical wall with the manual needle driver is difficult and the surgeon's hands and wrists are placed in awkward positions in order to manipulate the instrument. The difficulty of this procedure and the skill required to complete it limits the number of surgeons willing to do it. This then limits the options of patients who require the procedure. Alternative devices have been developed to remedy this situation, such as a septal stapler described in U.S. Pat. No. 7,438,208. However, the staples utilized are not as efficient or controllable as sutures generally used.

The technology and methodology for the medialization of the middle turbinate and septoplasty procedures, as well as the passing of suture through soft tissue and bone, in general, would benefit from further development.

The subject matter claimed herein is not limited to embodiments that solve any disadvantages or that operate only in environments such as those described above. Rather, this background is only provided to illustrate one exemplary technology area where some embodiments described herein may be practiced

SUMMARY

Embodiments relate to systems and devices for suture passing systems and devices. In particular, embodiments may relate to systems and devices for placing sutures in a restricted space.

In one embodiment, a suture-passing device may include a base mechanism. The base mechanism may include a first arm and a second arm. The suture-passing device may be configured to selectively pass a needle from an enclosed position within the first arm to an enclosed position within the second arm.

In another embodiment, the needle of the suture-passing device may be selectively passed from the enclosed position within the second arm to the enclosed position within the first arm.

In another embodiment, a device for suturing may include a base mechanism and a cartridge. The base mechanism may include a moveable joint between a pair of handles a first end and a pair of elongated members at a second end. The cartridge may be configured to be removably attached to the base mechanism. The cartridge may include a first arm and a second arm. Each of the first arm and the second arm may include a housing, a driving member, and a guide. The driving member may be disposed in the housing and may include dual shafts having a space therebetween. The guide may be attached to the housing and may include a guide surface extending therefrom. The guide surface may be at least partially disposed in a space between the shafts of the driving member. The first arm and the second arm may be positioned with the guides extending away from one another.

In another embodiment, the dual shafts of the device may be configured to engage and move a needle.

In another embodiment, the device may further include a needle having a shape generally corresponding to the guide surface. The needle may include notches in a first end section and a second end section.

In another embodiment, the needle may have a shape of an arc having a radius.

In another embodiment, the guide surface may have a shape of an arc having the radius of the needle shape.

In another embodiment, a method of passing a suture through tissue includes positioning a first arm and a second arm of a suture-passing device on opposite sides of the tissue. The first arm and the second arm may be attached to a first handle and a second handle by a moveable joint. Each of the first arm and the second arm may include a driver member having dual shafts, the driving member disposed in an opening in a housing, and a guide disposed over the opening and including a guide surface extending at least partially into a space between the dual shafts of the driving member. The method may further include loading a suture into an opening in a needle disposed around and having a shape generally corresponding to the guide surfaces. The method may further include moving the first and second handles toward one another to clamp the tissue between the guides. The method may further include actuating the driving members such that the driving member of the first arm engages with a notch in a first end of the needle and moves the needle along the guide surface of the first arm, through the tissue into the tissue and in contact with the guide surface of the second arm such that the driving member of the second arm engages with the notch in the needle to pull the needle into the second arm.

In another embodiment, moving the first handle and the second handle toward one another to clamp the tissue between the guides includes squeezing the handles to lock a protruding region of the second arm onto the tissue.

In another embodiment, moving the first handle and the second handle toward one another includes squeezing the handles to position the first arm and the second arm parallel with one another.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages will be set forth in the description which follows, and in part will be obvious from the description, or may be learned by the practice of the embodiments. The features and advantages of the embodiments will be realized and obtained by means of the instruments and combinations particularly pointed out in the claims. These and other features will become more fully apparent from the following description and claims, or may be learned by the practice of the embodiments as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3A is a top view of the example suture passer of FIG. 1A in an open configuration with a diagrammatic anatomic wall;

FIG. 3B is a top view of the example suture passer of FIG. 3A in a closed configuration about the anatomic wall;

FIG. 3C is a top view of the example suture passer of FIG. 3A in a clamped configuration about the anatomic wall;

FIG. 4A is a top cutaway view of the example suture passer of FIG. 3A;

FIG. 4B is a top cutaway view of the example suture passer of FIG. 3B;

FIG. 4C is a top cutaway view of the example suture passer of FIG. 3C;

FIGS. 5A-5E are top views of the example suture passer of FIG. 3C in various states of passing a suture needle through the anatomic wall;

FIG. 6A is a top cutaway view of the example suture passer of FIG. 5A;

FIG. 6B is a top cutaway view of the example suture passer of FIG. 5C;

FIG. 6C is a top cutaway view of the example suture passer of FIG. 5E;

DESCRIPTION OF EMBODIMENTS

Figure 1A:
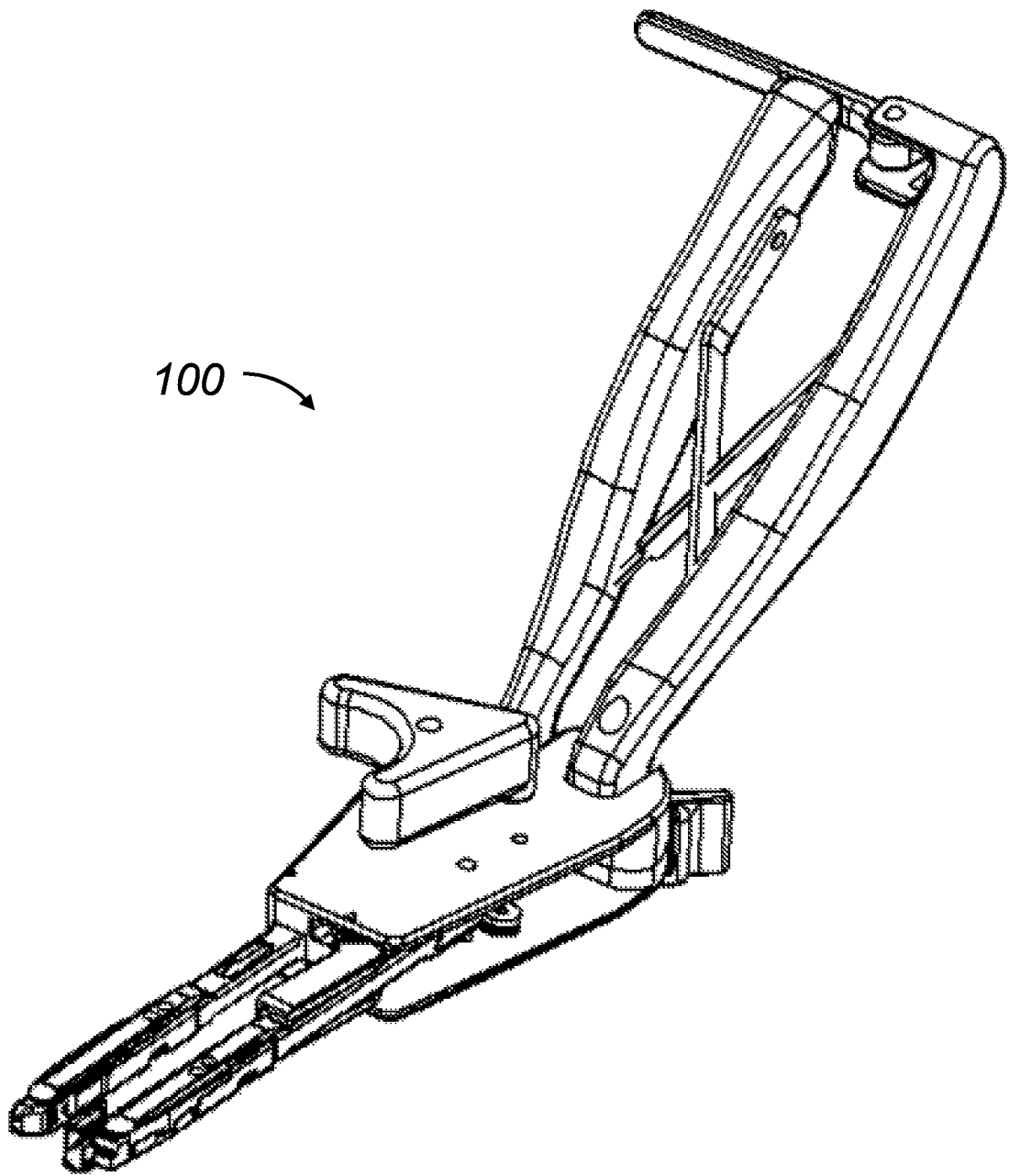
FIG. 1A is a top perspective view of an example suture passer in a clamped configuration.

Conventional needle drivers may allow a practitioner—typically a surgeon—to pass a suture needle from one side of the anatomic wall to the other. In tight spaces, the practitioner is challenged to deliver the needle to the desired location without damaging nearby tissue with the needle point. Conventional needle drivers generally include exposed needles that present a significant risk of undesirable damage to surrounding tissue. The risk of damage is particularly significant during introduction and removal of the conventional needle driver at the restricted space. Furthermore, arms of conventional needle drivers are generally not long enough for use in a nasal cavity—particularly for medicalization of a middle turbinate or a general septoplasty.

Passing the needle through the anatomic wall with a conventional needle driver may be difficult, often requiring the practitioner's hands and wrists to be located in awkward positions to manipulate the needle driver. Furthermore, the needle is generally repositioned relative to the needle driver prior to each needle insertion through the anatomic wall. Repetitive placement of the practitioner's hands and wrists into awkward positions may produce painful repetitive motion injuries, thus jeopardizing the practitioner's clinical effectiveness, as well as their livelihood.

Embodiments of the invention relate to systems and devices for suture passing systems and devices. In particular, embodiments described herein may relate to systems and devices for placing sutures in a restricted space. Some embodiments may be used in a nasal cavity.

Advantageously, in contrast to conventional needle drivers, embodiments described herein may guard a patient's anatomy from a sharp needle tip until the needle is actually passed through the anatomic wall. Thus, damage to nearby tissue and the complications associated with the tissue damage may be reduced and potentially eliminated when compared to conventional needle drivers.

Advantageously, embodiments may reduce and potentially eliminate a practitioner's risk of injury when compared to conventional needle drivers by reducing the need for the practitioner to extraordinarily manipulate the suture passing system. Thus, the practitioner's clinical effectiveness and livelihood may be better protected when compared to conventional needle drivers.

Furthermore, the suture needle of the disclosed embodiments may not be repositioned relative to the rest of the suture passer. Advantageously, procedure time may be reduced, providing a number of benefits, including: shortening the time a patient is under anesthetic, reduced patient costs, and improved facility efficiency.

Suture passing systems described herein may be used, for example, for lateralization of the middle turbinate after endoscopic sinus surgery. The suture passing system may allow medialization of the middle turbinate to the nasal septum by passing absorbable suture through the appropriate anatomic walls.

Lateralization of the middle turbinate and the formation of synechia remains one of the most frustrating complications following endoscopic sinus surgery. These complications often lead to recurrence of symptoms, and in many instances, may require revision surgery. Conventional techniques, maneuvers, and devices used to lateralize middle turbinates generally result in relatively high rates of synechia formation. Conventionally, manually suturing the middle turbinates to the nasal septum has been technically difficult. Advantageously, embodiments described herein may be employed in techniques to conveniently and safely secure the middle turbinates to the nasal septum.

Suture passing systems described herein may further be used for mucoperiosteal flap reapproximation after septoplasty surgery. Surgery on the nasal septum, including the commonly-performed septoplasty surgery, generally requires the reapproximation of mucoperiosteal flaps created during the surgical procedure. Commonly, the nose may be packed with gauze and other materials to apply pressure on each side of the mucoperiosteal flaps to prompt the reapproximation of the flaps. Often, the packing may be painful and uncomfortable for the patients. Many practitioners manually place absorbable quilting suture that may decrease the need for packing. However, placing the absorbable quilting suture may be tedious and somewhat difficult to perform manually.

Conventionally, septoplasty flap reapproximation may alternatively be performed via absorbable staples. Stapling the septoplasty flap generally may not allow the flaps to be tightened together. The staples generally come in only one size and may often fail to cinch the flaps together. Furthermore, device failure is often common. Many practitioners prefer to suture rather than staple the septum, as suturing is a more traditional approach. Furthermore, many practitioners have concerns that the larger staples increase the risk of postoperative complications such as septal perforation. Advantageously, embodiments described herein may be employed to conveniently and safely suture mucoperiosteal flaps for reapproximation.

Devices, systems, and methods for suturing tissue are described herein. In various embodiments, such devices, systems, and methods may enable a suture to be passed through soft tissue and bone in a confined space. The device for passing suture may then be repositioned and the suture may be passed again through the soft tissue and bone. This will enable attachment of soft tissue in a confined space, such as the nasal cavity. In this application, "suture" refers to any sort of flexible material than may be utilized to attach or reattach soft tissue. "Suture needle" may refer to a specific device for passing suture through soft tissue, including at least two pointed ends for puncturing soft tissue and at least one medial aperture for retaining the suture.

Reference will now be made to the figures wherein like structures will be provided with like reference designations. The drawings are diagrammatic and schematic representations of exemplary embodiments and, accordingly, are not limiting of the scope of the claimed subject matter, nor are the drawings necessarily drawn to scale.

FIG. 1A is a top perspective view of an example suture passer 100 in a clamped configuration.

Figure 1B:
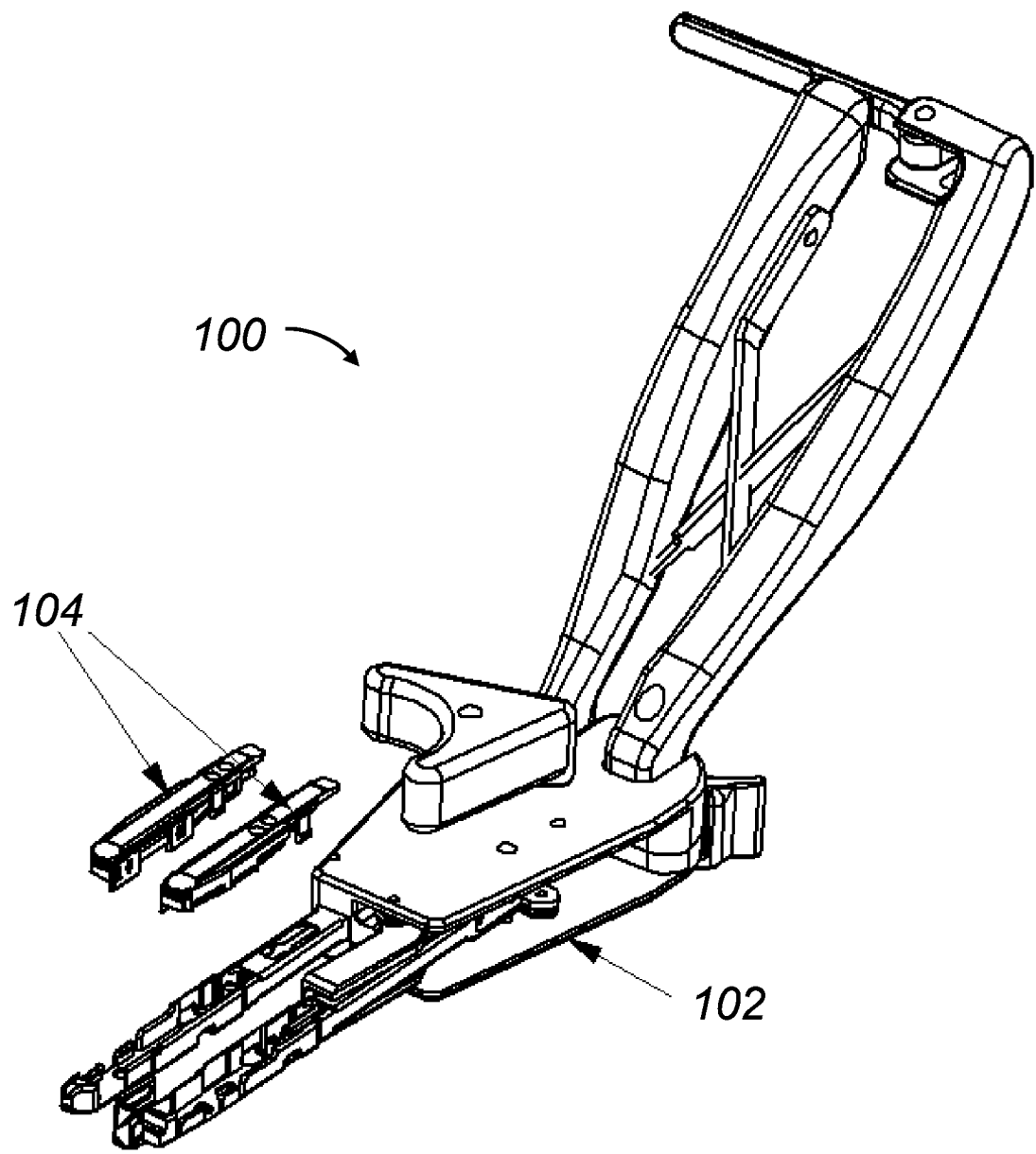
FIG. 1B is a top perspective exploded view of the example suture passer of FIG. 1.

FIG. 1B is a top perspective exploded view of the example suture passer 100 of FIG. 1A. In some embodiments, the suture passer may include a base mechanism 102 and a cartridge 104. The base mechanism 102 may be cleanable, sterilizable, and reusable. Preferably, the cartridge 104 is disposable. A clean and sterile cartridge 104 may be temporarily assembled to the base mechanism 102 for a suturing procedure and removed and discarded after the suturing procedure.

However, in some embodiments, the entire suture passer 100 may be disposable. In such embodiments, the cartridge 104 may be formed into the base mechanism 102. A clean and sterile suture passer 100 may be used for a single suturing procedure and discarded after the suturing procedure.

Figure 2A:
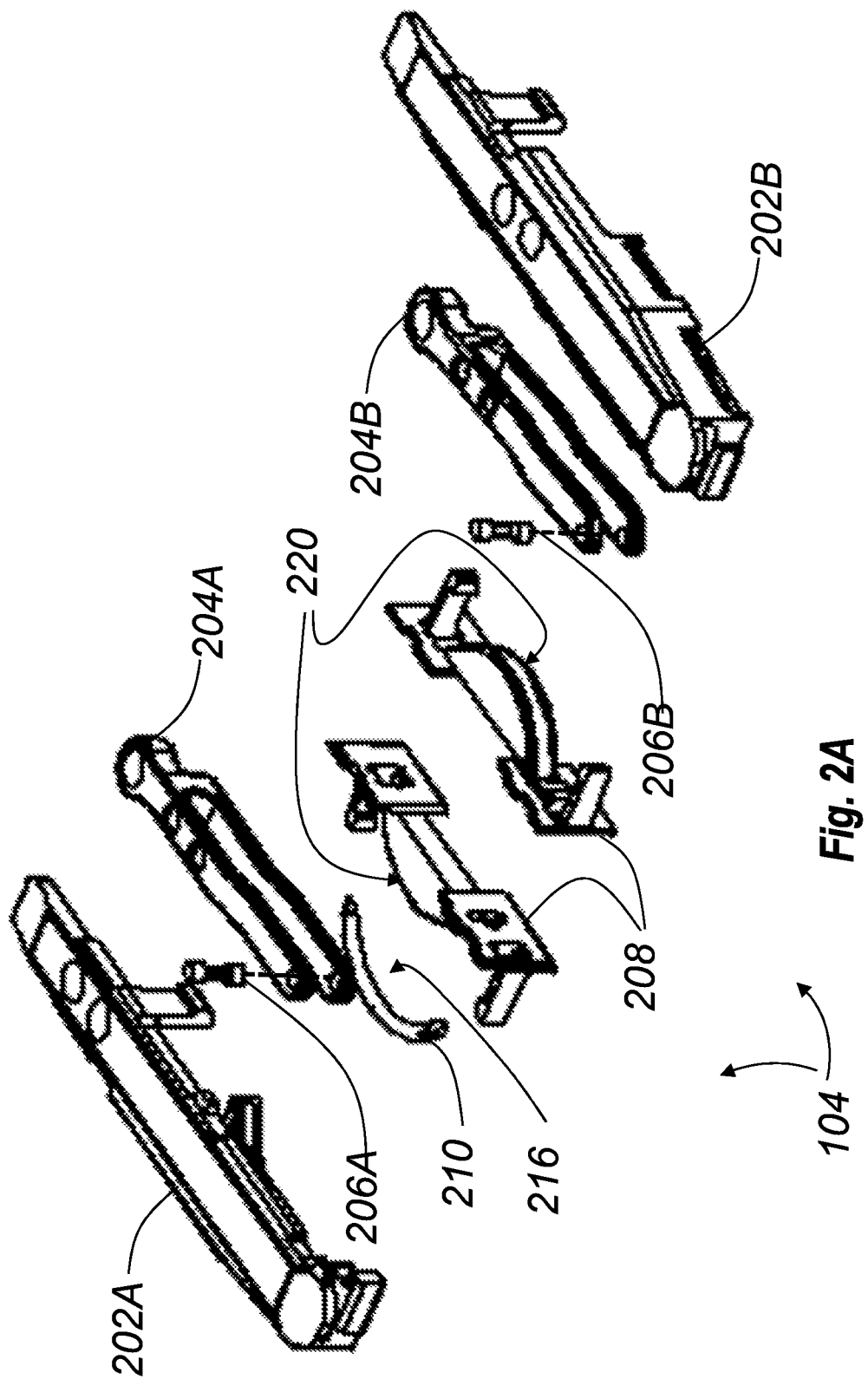
FIG. 2A is a top perspective exploded view of a cartridge that may be included in the suture passer of FIG. 1.

FIG. 2A is a top perspective exploded view of the cartridge 104. The cartridge may include a pair of housings 202A and 202B (collectively "housings 202"). Driving members 204A and 204B (collectively "driving members 204") may be located in each of the housings 202. Each of the driving members 204 may include a shaft 206A and 206B (collectively "shafts 206") for engaging and moving a needle 210 during a suturing procedure as described herein.

Figure 2B:
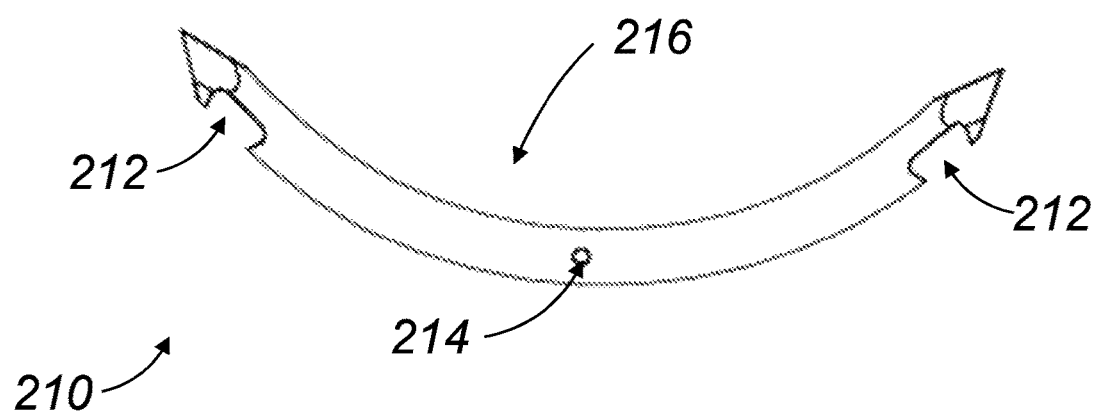
FIG. 2B is a top view of a needle that may be used in the suture passer of FIG. 1A.

FIG. 2B is a top view of the needle 210. The needle 210 may include openings 212 configured to interface with the shafts 206 during a suturing procedure. Suture (not shown) such as absorbable suture may interface with the needle 210 via an opening 214. The needle 210 may be arced with a nominal radius, as indicated generally at 216.

Referring again to FIG. 2A, each of the housings 202 may include a guide 208. Each guide 208 may include a guide surface 220 having approximately the same nominal radius as the nominal radius 216 of the needle 210. The needle 210 may be located within the housing 202A such that the cartridge 104 may be inserted into a restricted anatomic space without risk of damaging tissue with a sharp point of the needle 210.

During a suturing procedure, the housings 202 are preferably positioned such that the radius of each guide surface 220 are nominally concentric, i.e., such that the needle 210 may move between the guide surfaces 220 along an arced path having approximately the same nominal radius as the nominal radius 216 of the needle 210 and the guide surfaces 220. During a suturing procedure, the driving member 204A may be driven forward such that the shaft 206A interfaces with one of the openings 212 of the needle 210 and drives the needle 210 out of the housing 202A. The needle 210 may be driven by the driving member 204A such that the needle 210 is received by the housing 202B while the driving member 204B is located in a forward position. Following a tip of the needle 210 being received in the housing 202B, the driving member 204B may be driven rearward such that the shaft 206B interfaces with another of the openings 212 of the needle 210 and pulls the needle 210 into the housing 202B with assistance from the guide 208. The process may be reversed to drive the needle 210 from the housing 202B to the housing 202A.

In some embodiments, the cartridge 104 may be removably attached to the base mechanism 102 (shown in FIG. 1B). Attaching and removing the cartridge 104 to and from the base mechanism 102 may be accomplished with assistance from loading trays and unloading trays.

Figure 10:
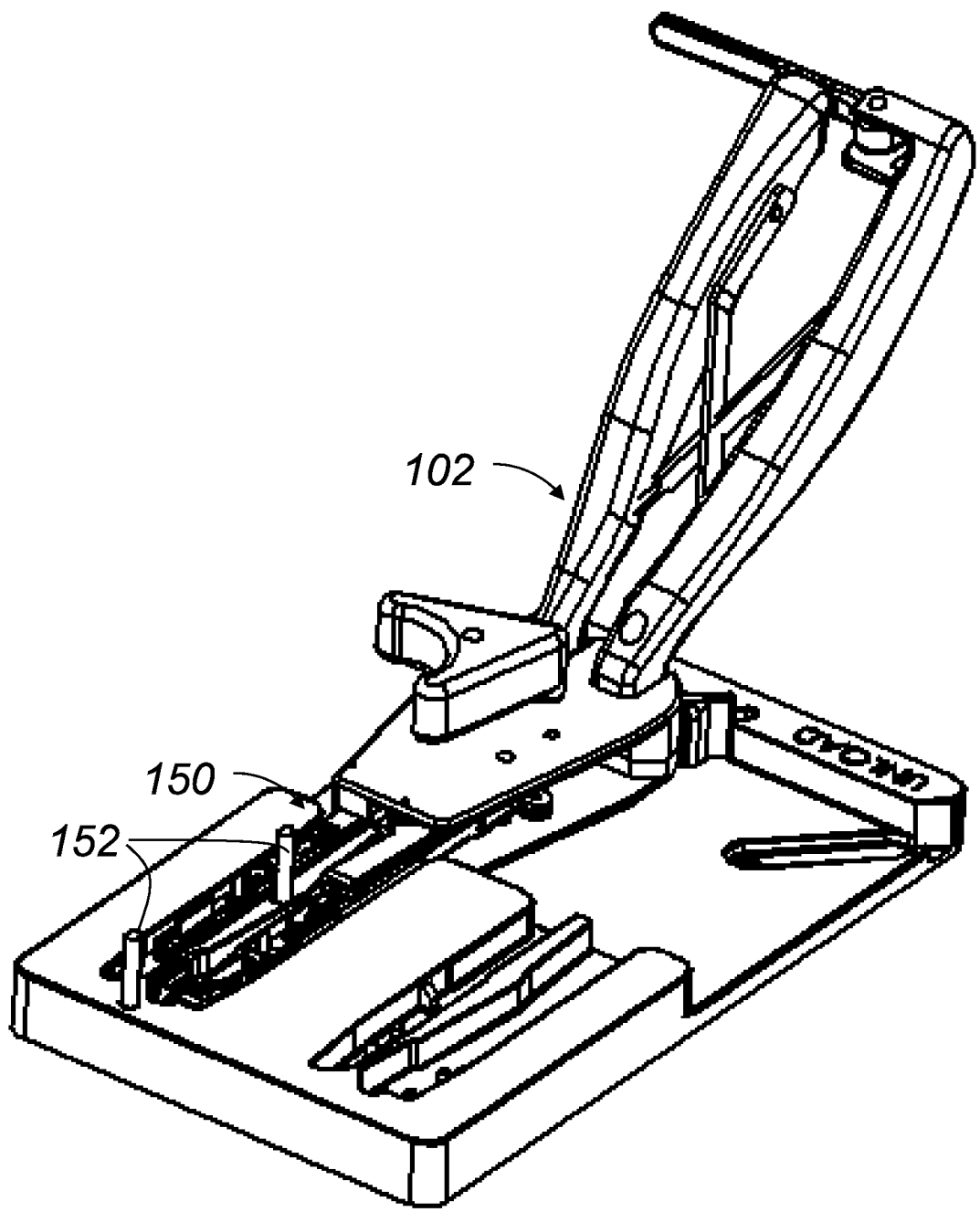
FIG. 10 is a top perspective view of a base mechanism of the example suture passer of FIG. 1A in an example loading tray.

FIG. 10 is a top perspective view of the base mechanism 102 in an example loading tray 150. The loading tray 150 is shaped such that the base mechanism 102 is properly positioned to receive the cartridge 104 (not shown). The loading tray 150 may include protrusions 152.

Figure 11:
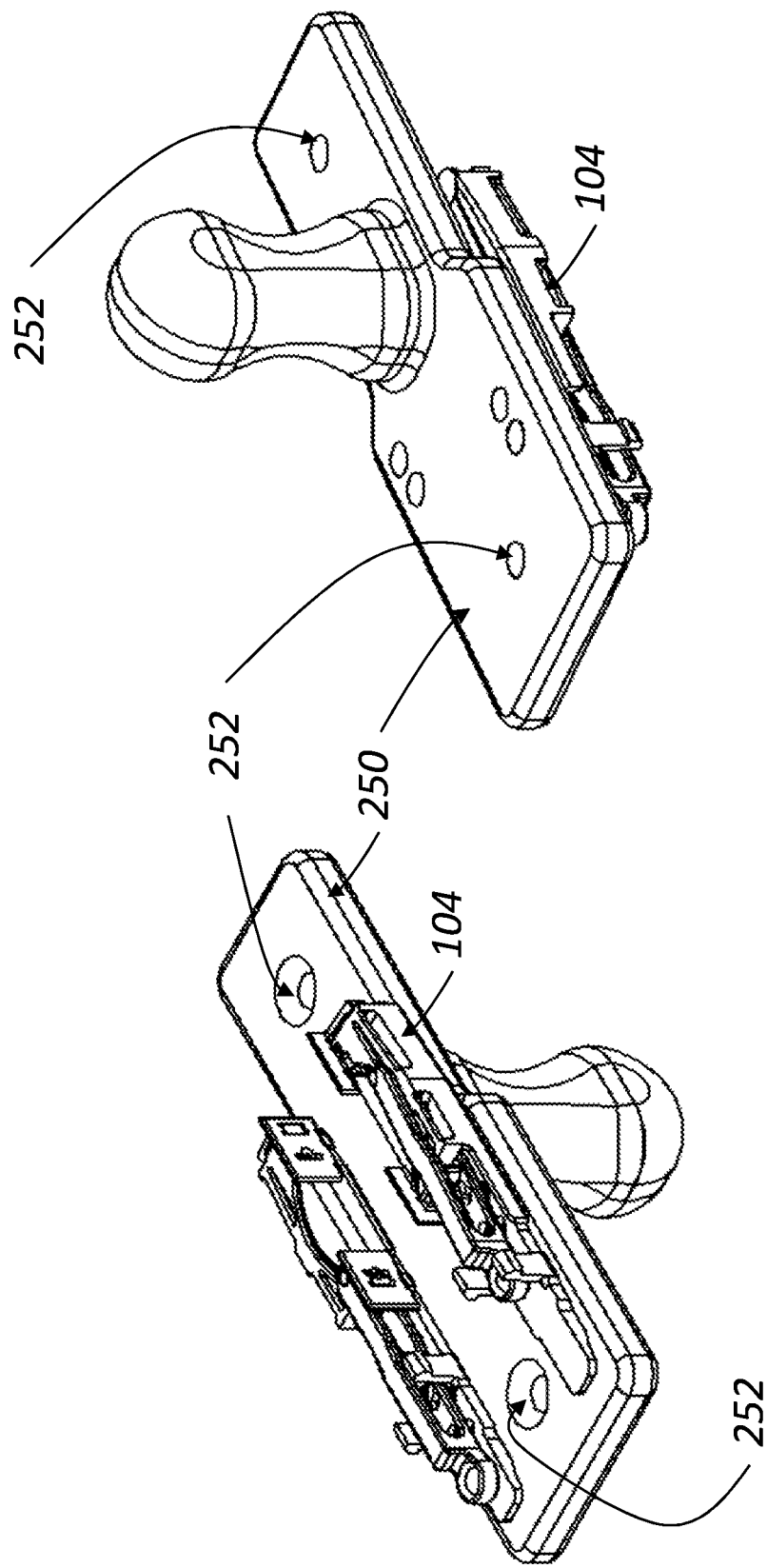
FIG. 11A is a bottom perspective view of the cartridge of FIG. 2 on a delivery device.
FIG. 11B is a top perspective view of the cartridge and delivery device of FIG. 11A.

FIG. 11A and FIG. 11B are a bottom perspective view and a top perspective view, respectively, of the cartridge 104 on a delivery device 250. The delivery device 250 may position the cartridge 104 such that the cartridge 104 may be introduced to the base mechanism 102. The delivery device 250 may include openings 252 sized and positioned to interface with the protrusions 152 of the loading tray 150, as demonstrated in FIG. 12.

Figure 12:
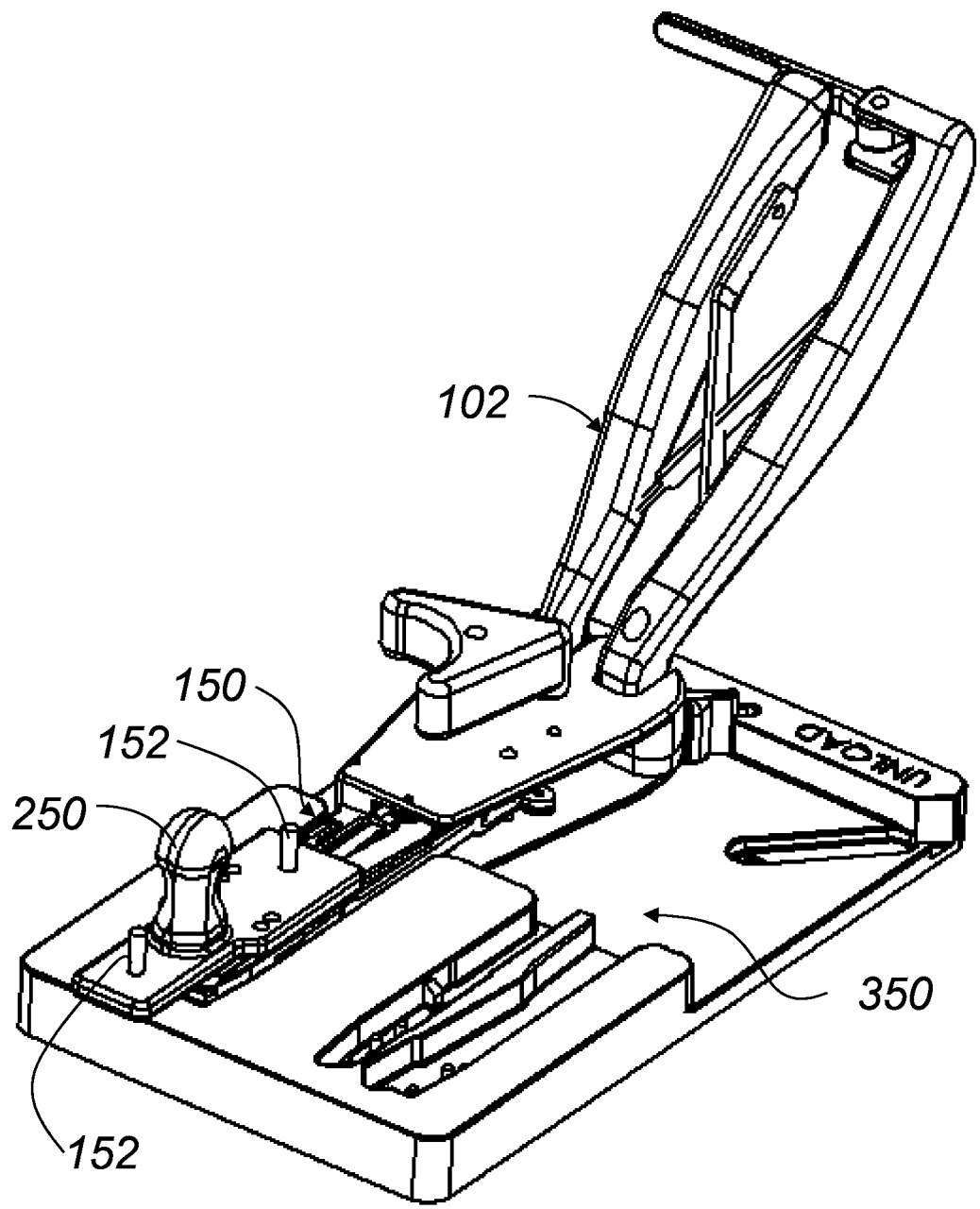
FIG. 12 is a top perspective view of the base mechanism and example loading tray of FIG. 10 including the cartridge and delivery device of FIG. 11A.

FIG. 12 is a top perspective view of the base mechanism 102 and loading tray 150 including the delivery device 250. The openings 252 of the delivery device 250 may fit over the protrusions 152 such that the cartridge 104 (shown in FIGS. 11A and 11B) is properly aligned to allow the cartridge 104 to be attached to the base mechanism 102.

Figure 13:
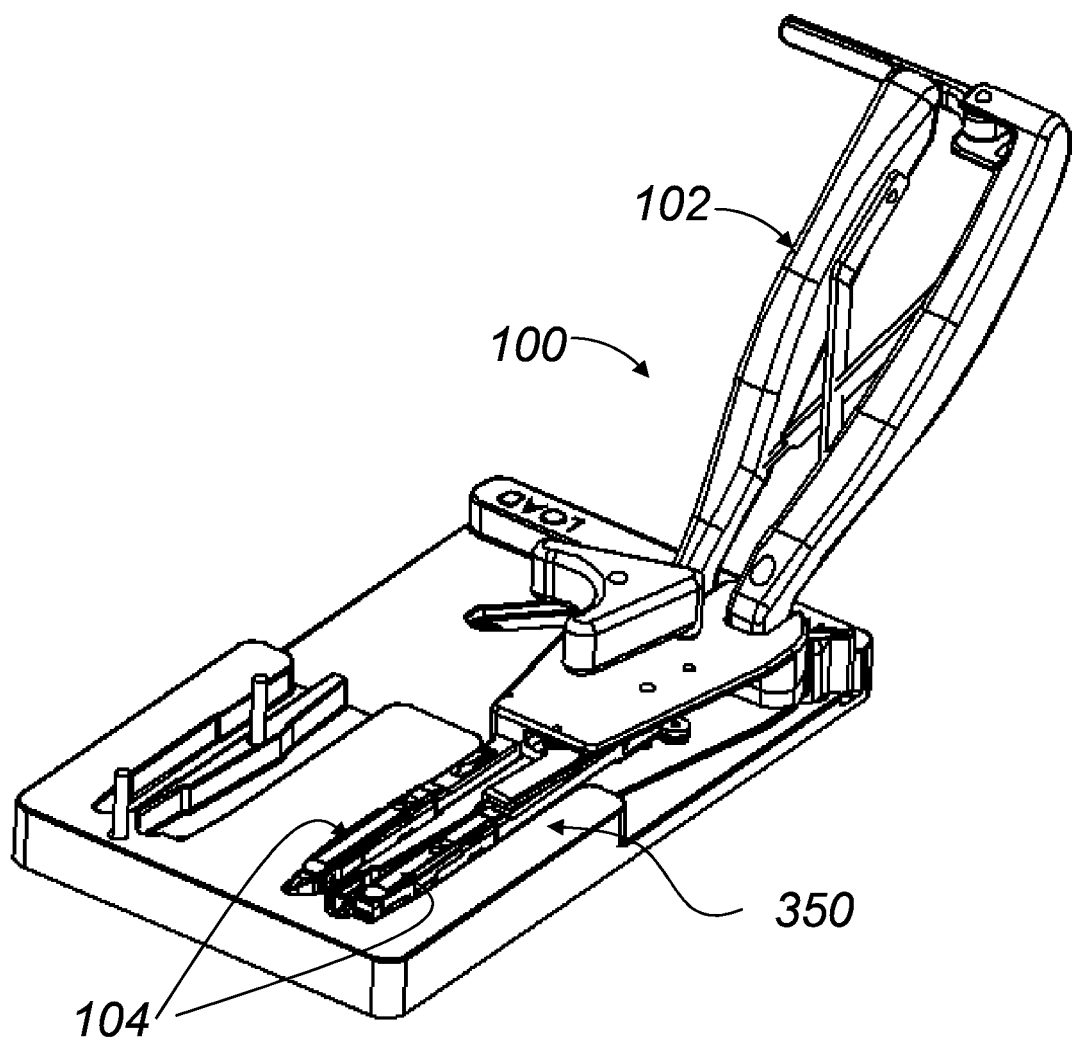
FIG. 13 is a top perspective view of the example suture passer of FIG. 1A in an example unloading tray.

FIG. 12 also shows an unloading tray 350. Although the unloading tray 350 is shown attached to the loading tray 150, they may be separate. The unloading tray may include protrusions 352 positioned to eject the cartridge 104 from the base mechanism 102 when the suture passer 100 is placed in the unloading tray 350. Like the loading tray 150, the unloading tray 350 may be shaped such that the suture passer 100 is properly positioned to eject the cartridge 104, as demonstrated in FIG. 13.

FIG. 3A is a top view of the suture passer 100 in an open configuration shown proximate to a diagrammatic anatomic wall 302. In the open configuration, arms 304A and 304B (collectively "arms 304") may be positioned to easily straddle the anatomic wall 302.

FIG. 3B is a top view of the suture passer 100 in a closed configuration about the anatomic wall 302. In the closed configuration, the arms 304 may be generally positioned such that the guide surfaces 220 (shown in FIG. 2A) are nominally concentric. In some embodiments, the arms 304 may be substantially parallel in the closed configuration. The suture passer 100 may be moved from the open configuration to the closed configuration by moving the handles 306 together. In some embodiments, the suture passer 100 may include a spring mechanism 308 for providing a resistance force when the handles 306 are moved together.

FIG. 3C is a top view of the suture passer 100 in a clamped configuration about the anatomic wall 302. In the clamped configuration, the arms 304 may remain in the same position as in the closed configuration, but a finger 310 may move to secure the suture passer 100 relative to the anatomic wall 302. Keeping the arms 304 in the same position may provide a suitable path for the needle 210 (shown in FIGS. 2A and 2B) as described with reference to FIG. 2A. The suture passer 100 may be moved from the closed configuration to the clamped configuration by moving the handles 306 closer together. The clamped configuration may also be described as an operating position. The suture passer 100 may be held in the clamped configuration by a securing mechanism 312, which may engage to prevent inadvertent opening of the instrument.

FIGS. 4A-4C show various configurations of an example linkage mechanism 406 configured to allow the suture passer 100 to move between the open, closed, and clamped configurations. The linkage mechanisms for driving the needle have been omitted for convenience. In some embodiments, the arm 304A and a grip 404 of the handle 306 may be positioned on a body 402 of the suture passer 100. The arm 304B may be functionally coupled to grip 408 of the handle 306 via a linkage mechanism 406. In moving from the open configuration (FIG. 4A) to the closed configuration (FIG. 4B), the arm 304B may be moved toward the arm 304A until the arm 304B contacts a stop (not shown). In moving from the closed configuration to the clamped configuration (FIG. 4C), further movement of the grip 408 may cause the linkage mechanism 406 to move a finger 310 functionally coupled toward the arm 304A.

FIGS. 5A-5E are top views of the example suture passer 100 in various states of passing a suture needle through the anatomic wall 302. When the suture passer 100 is in the clamped configuration, a lever 502 may be rotated to drive the needle 210 (shown in FIG. 2A) from one arm to the other. Optionally, the lever 502 may be accessible from both sides of the suture passer 100 as shown in FIGS. 5A-5E.

FIGS. 6A-6C show an embodiment of linkage mechanisms 602 for driving the needle 210 through the anatomic wall 302. The outer housings of the arms and the linkage mechanism for moving the arms have been omitted for convenience. FIG. 6A is a top cutaway view of the example suture passer of FIG. 5A. FIG. 6B is a top cutaway view of the example suture passer of FIG. 5C. FIG. 6C is a top cutaway view of the example suture passer of FIG. 5E.

Figure 7B:
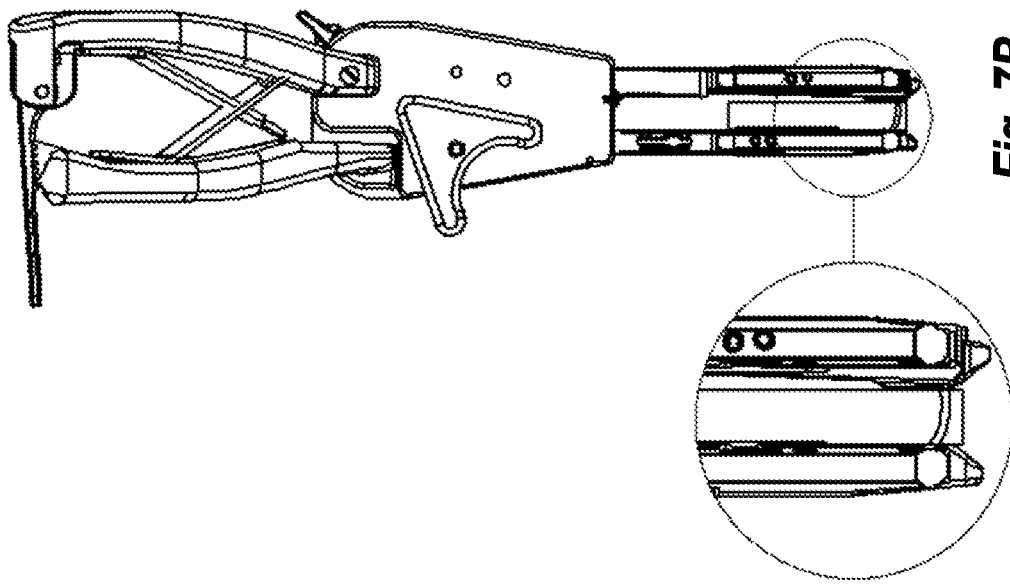
FIG. 7B is a top view of the example suture passer of FIG. 7A in the clamped configuration.
Figure 7A:
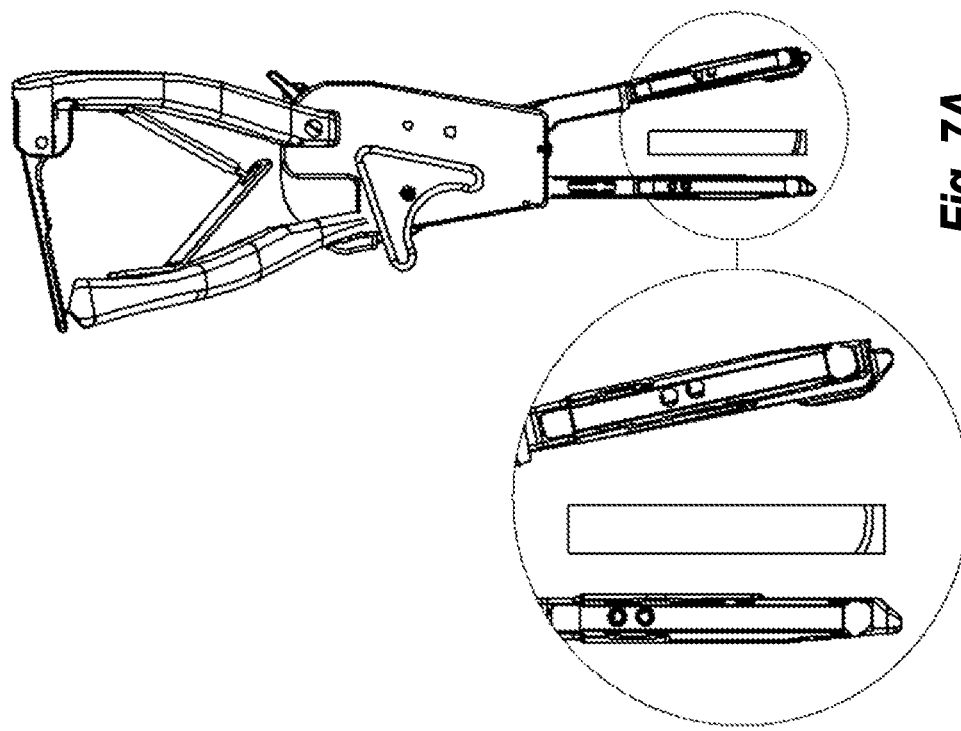
FIG. 7A is a top view of the example suture passer of FIG. 5E in the open configuration.
Figure 8E:
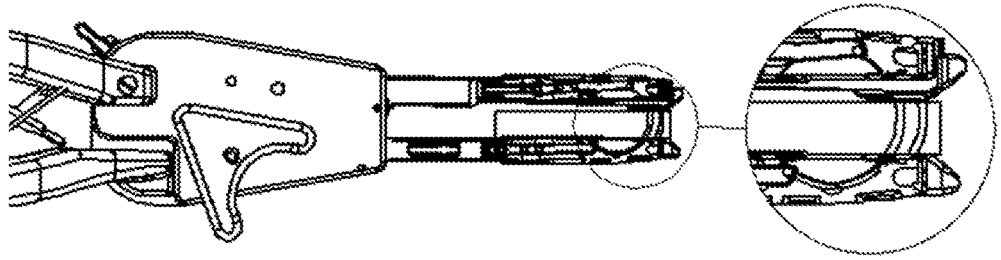
FIGS. 8A-8E are top views of the example suture passer of FIG. 7B in various states of passing the suture needle through the anatomic wall.
Figure 8D:
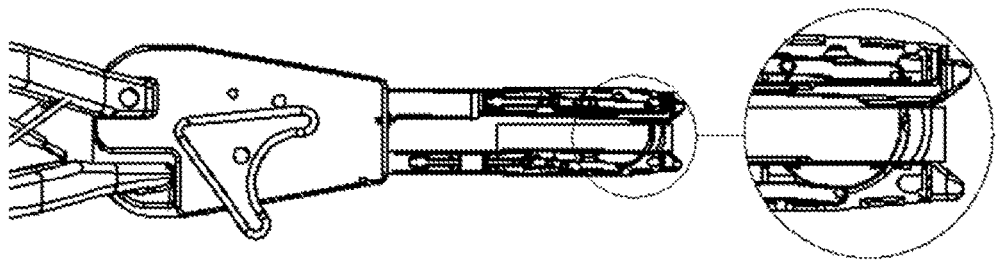
Figure 8C:
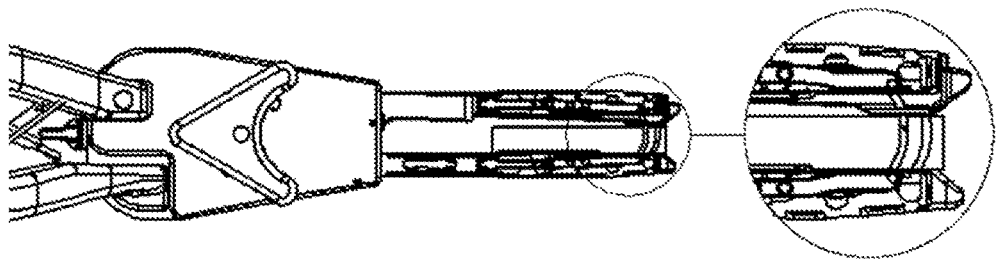
Figure 8B:
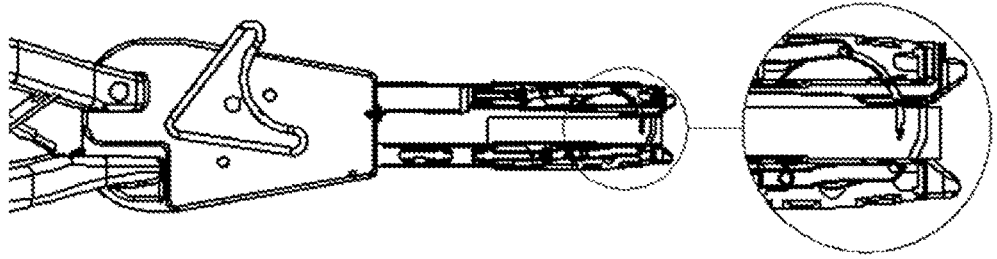
Figure 8A:
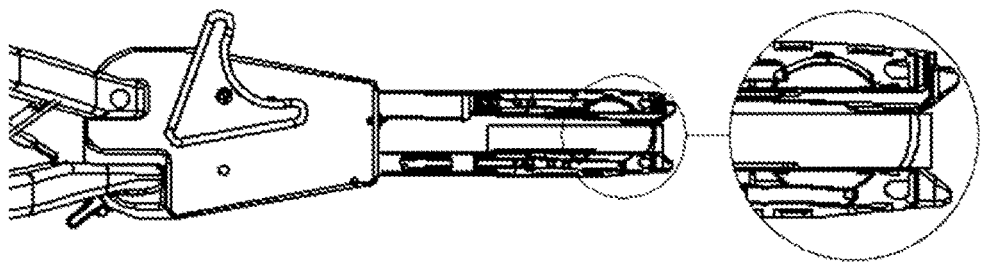

Once the suture has been passed through the anatomic wall 302, the suture passer 100 may be opened as shown in FIG. 7A. The suture passer 100 may then be repositioned relative to the anatomic wall 302 and clamped again in a new desired position as shown in FIG. 7B. The needle 210 and the suture may then be passed back through the anatomic wall 302 in the new desired position as shown in FIGS. 8A-8E. The practitioner may continue placing sutures in a similar manner as the practitioner deems necessary.

Figure 9B:
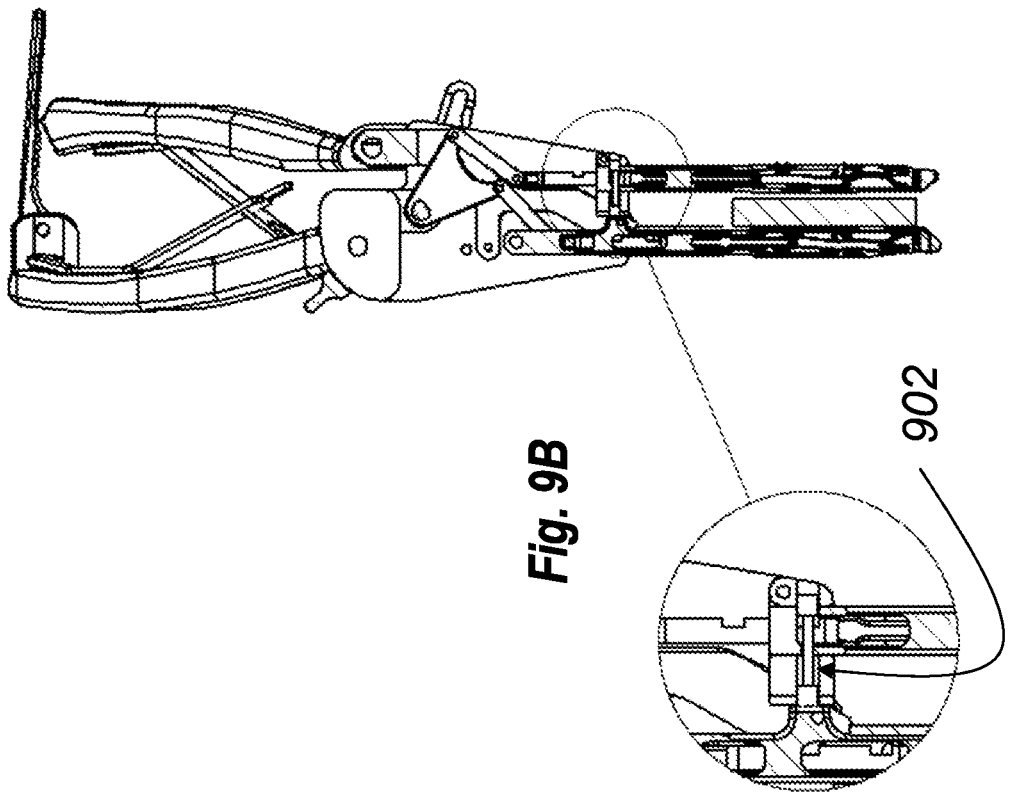
FIG. 9B is a bottom cutaway view of the example suture passer of FIG. 9A in the clamped configuration.
Figure 9A:
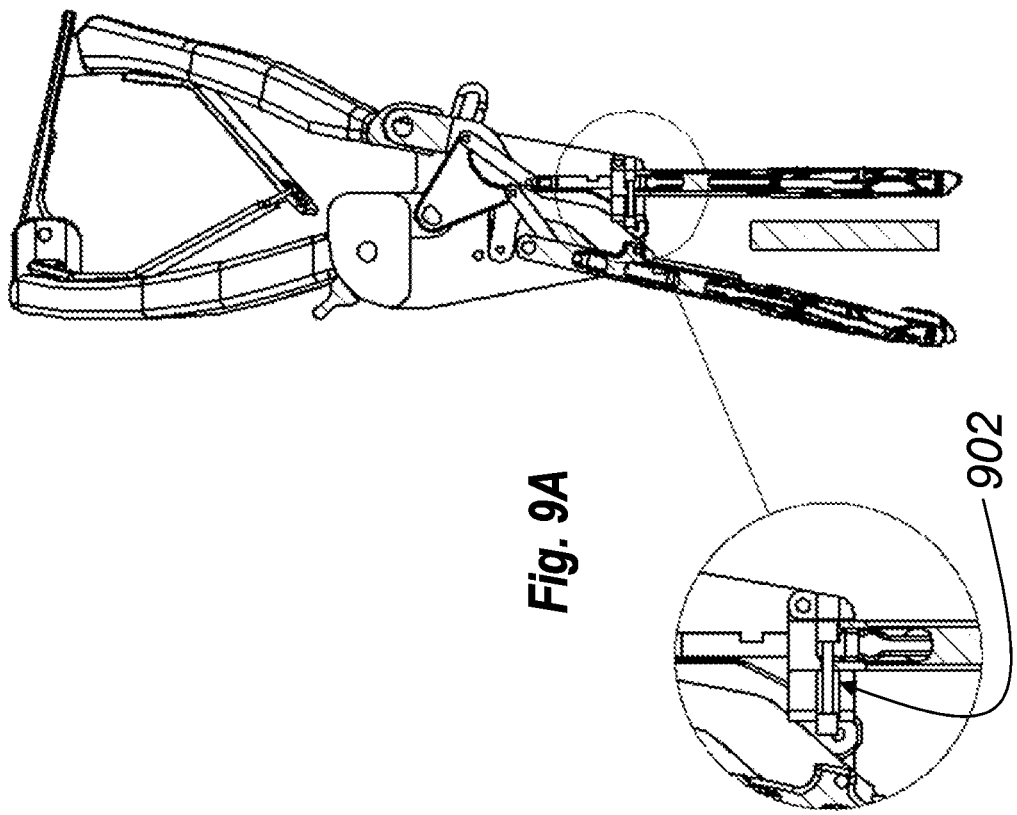
FIG. 9A is a bottom cutaway view of the example suture passer of FIG. 1A in an open configuration.

FIG. 9A is a bottom cutaway view of the suture passer 100 in the open configuration. FIG. 9B is a bottom cutaway view of the suture passer 100 in the clamped configuration. As shown in FIGS. 9A and 9B, in some embodiments, the suture passer 100 may include a locking mechanism 902. The locking mechanism 902 may prevent the lever 502 from being rotated and the needle 210 from exiting the arms 304 while the suture passer 100 is in the open configuration. However, when the suture passer is in the closed and/or clamped configuration, the locking mechanism 902 may be positioned such that the lever 502 may be rotated and the needle 210 may be passed between arms 304.

Figure 14:
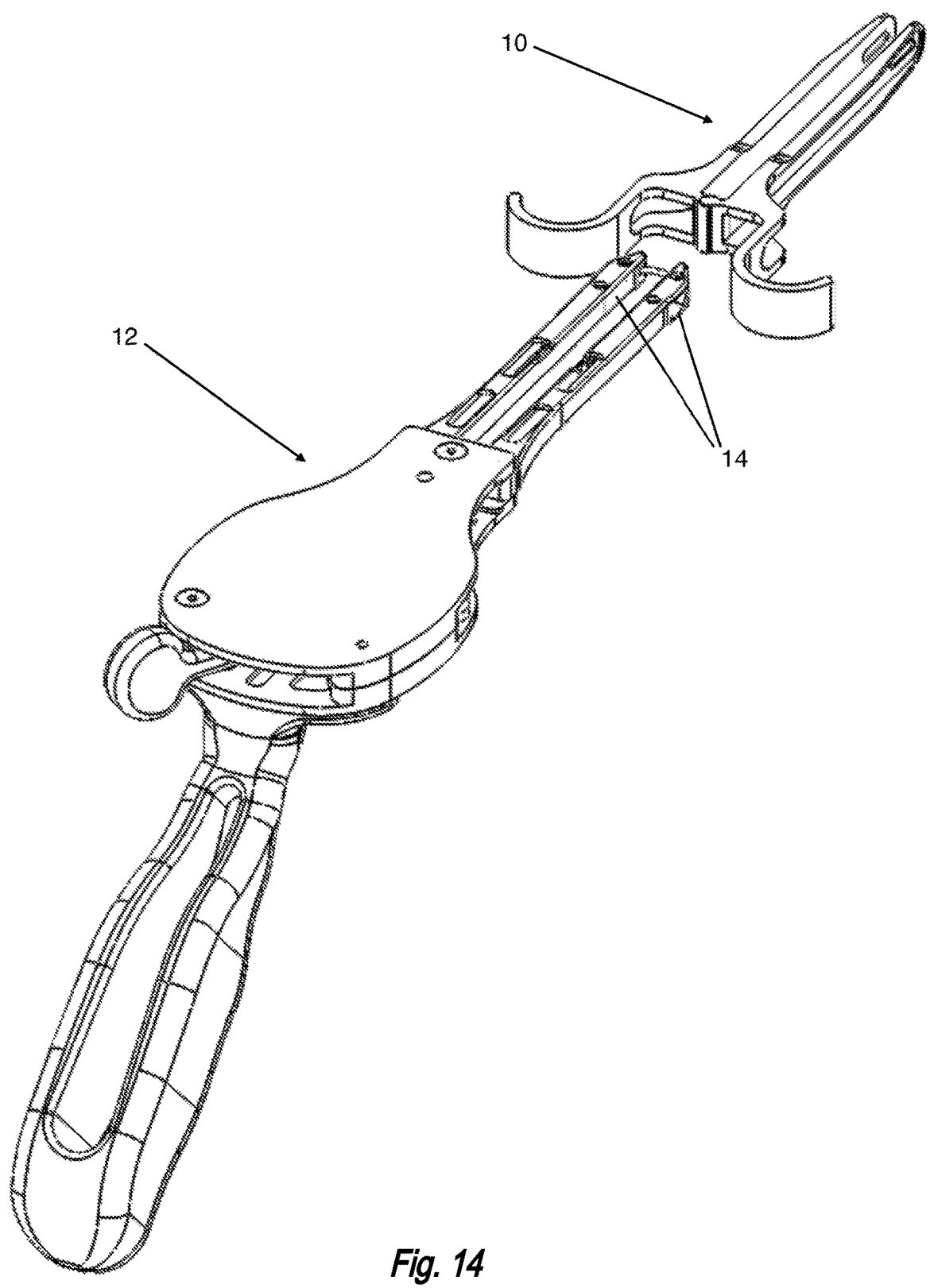
FIG. 14 is a perspective view of a fully assembled suture-passing device.

FIG. 14 depicts another example device for suturing tissue. The device includes a tissue-manipulating cannula assembly 10, a suture activation assembly 12, and removable suture housing assemblies 14. During a surgical procedure, such as the medialization of the middle turbinate or septoplasty, the components of the tissue-manipulating cannula assembly 10 are applied to the nasal cavity first. The suture activation assembly 12 with the disposable suture housing assemblies 14 are applied next, allowing tissue compression assembly to constrain the soft tissue to be sutured. The suture activation assembly 12 may then be actuated, thereby actuating disposable suture housing assemblies 14 and allowing for the suturing of soft tissue.

Figure 15:
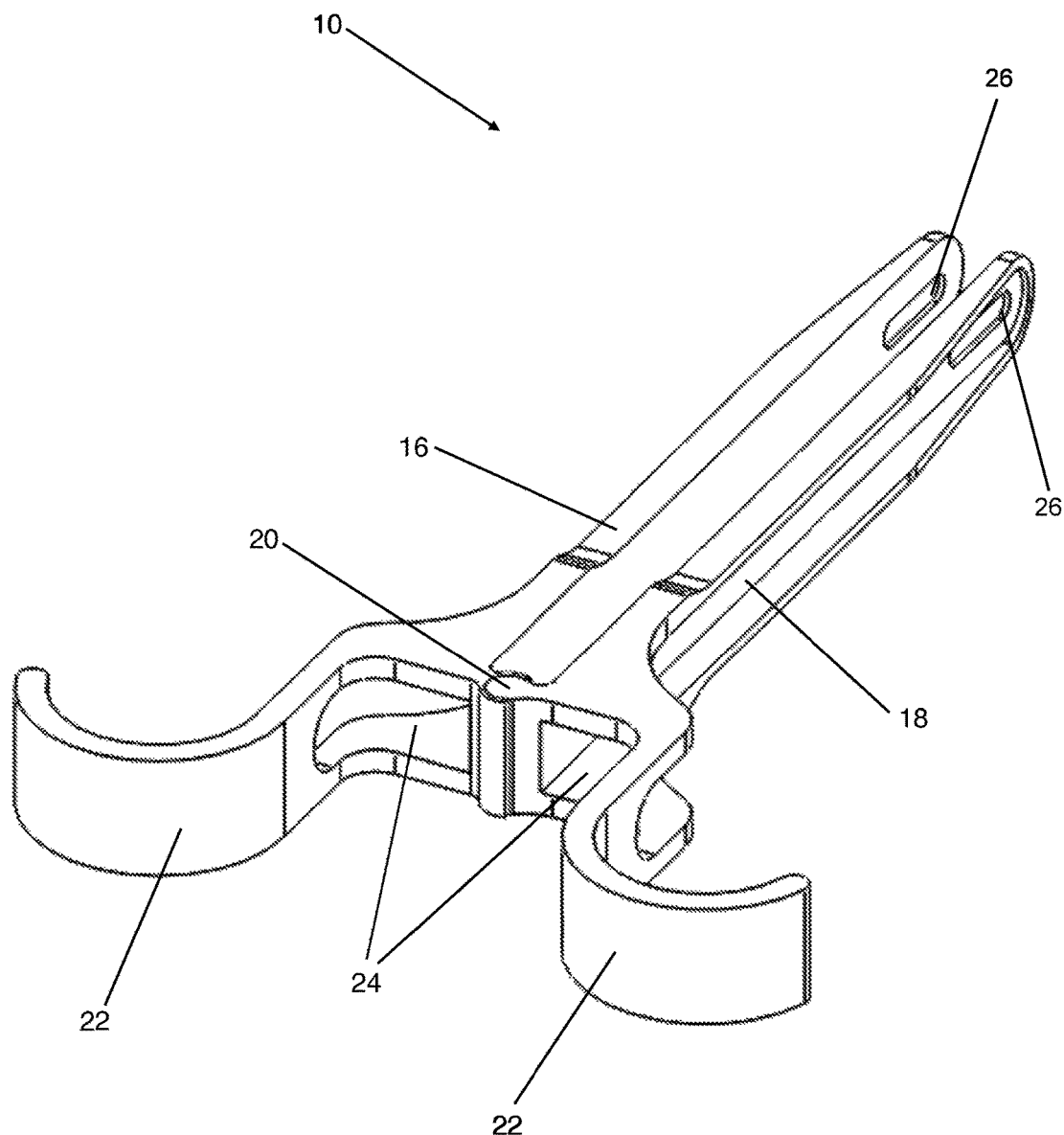
FIG. 15 is a perspective view of a tissue-manipulating cannula assembly of FIG. 14.

An embodiment of the tissue-manipulating cannula assembly 10 is illustrated in FIG. 15. The tissue-manipulating cannula assembly 10 may be made of titanium, cobalt chrome, or any other material that will allow for the manipulation of material at the surgical site. The material may be able to undergo and withstand a sterilizing process, such as a steam autoclave, radiation sterilization, or any other form of sterilization known in the art. The tissue-manipulating cannula assembly 10 may include a first manipulating member 16 and a second manipulating member 18. First 16 and second 18 manipulating members are configured to readily engage and disengage with each other using a connection interface 20. The connection interface 20 is configured to allow first 16 and second 18 manipulating members to engage and disengage readily using a clip configuration. First manipulating member 16 may be inserted into one nasal cavity first. Second manipulating member 18 may be inserted into the other nasal cavity second. The first 16 and second 18 manipulating members may then be coupled or clipped together with connection interface 20. The first 16 and second 18 manipulating members further include a number of member manipulation handles 22. Member manipulation handles 22 are configured to allow the operator of the device to manipulate and place the first 16 and second 18 manipulating members during the procedure. The tissue-manipulating cannula assembly 10 further includes a number of cannula-receiving apertures 24. The cannula-receiving apertures 24 are configured to receive a pair of suture application arms (described below). As this pair of arms is inserted through the cannula-receiving apertures 24, the first 16 and second 18 manipulating members will abut against the arms (see FIG. 14) and compress the first 16 and second 18 manipulating members around a pivot point created by the connection interface 20. This will allow the tissue to be constrained and held in place while the suturing takes place.

The tissue-manipulating cannula assembly 10 further includes a number of suture-passing openings 26. The suture-passing openings 26 are positioned at the distal ends of the first 16 and second 18 manipulating members. They are configured to allow the passage of a suture and suture needle through them and into the soft tissue. The suture-passing openings 26 may be configured having an oblong geometry, as shown in FIG. 15. This enables the suture application arms (described below) to be moved once the suture has been passed through the tissue. Once the suture has been passed, the application arms may be repositioned proximally or distally relative to the operator to allow the suture to be passed back through the tissue. The oblong geometry of the suture-passing openings 26 allow this repositioning without requiring the tissue-manipulating cannula assembly 10 to be repositioned or lose its compression on or constraint of the tissue. It is to be understood that the suture-passing openings 26 may be configured having any suitable shapes or dimensions to enable movement of the arms without repositioning of the tissue-manipulating cannula assembly 10 or loss of compression on the tissue.

Figure 16A:
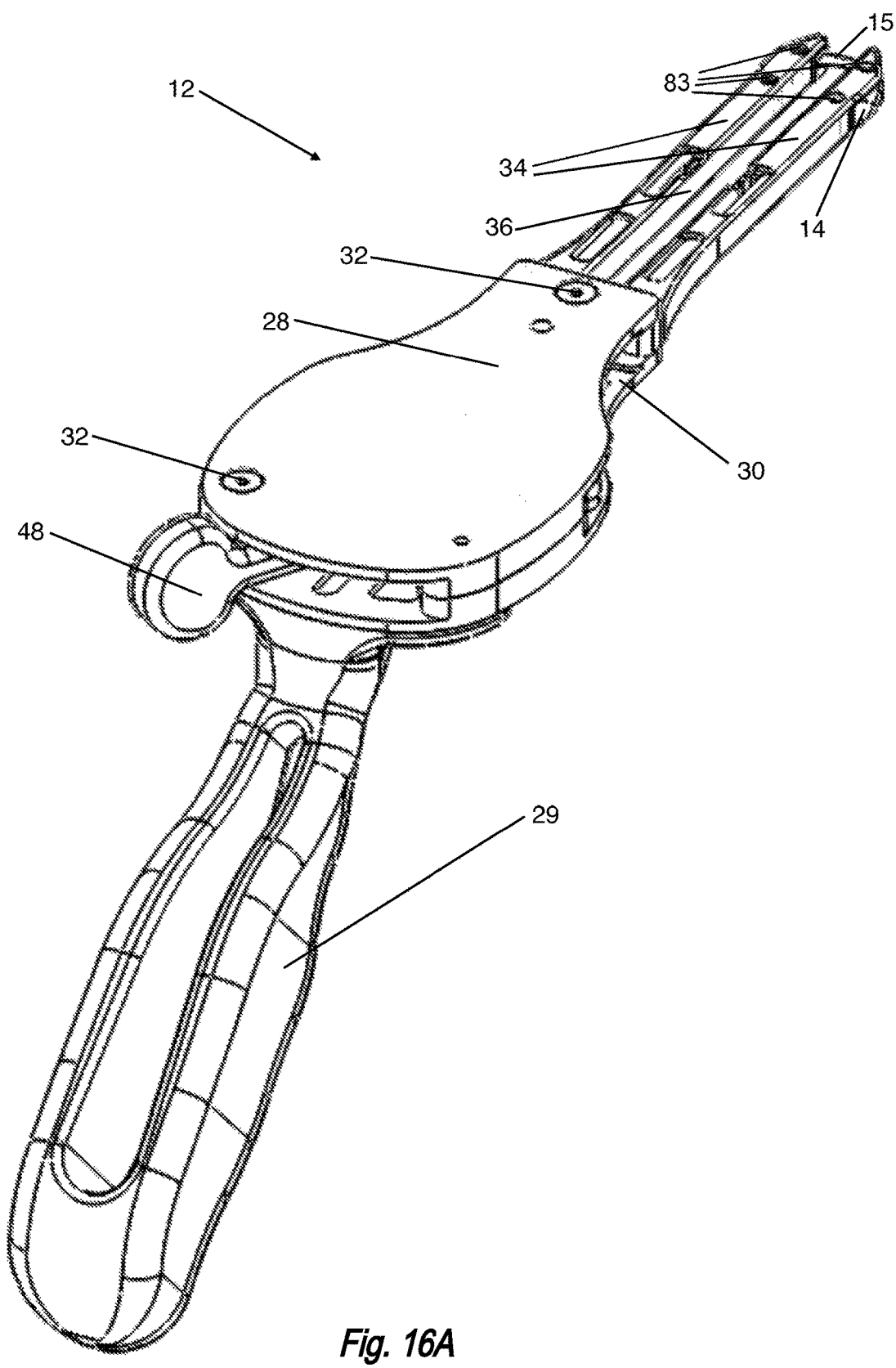
FIGS. 16A-16B are perspective views of a suture activation assembly of FIG. 14.
Figure 16B:
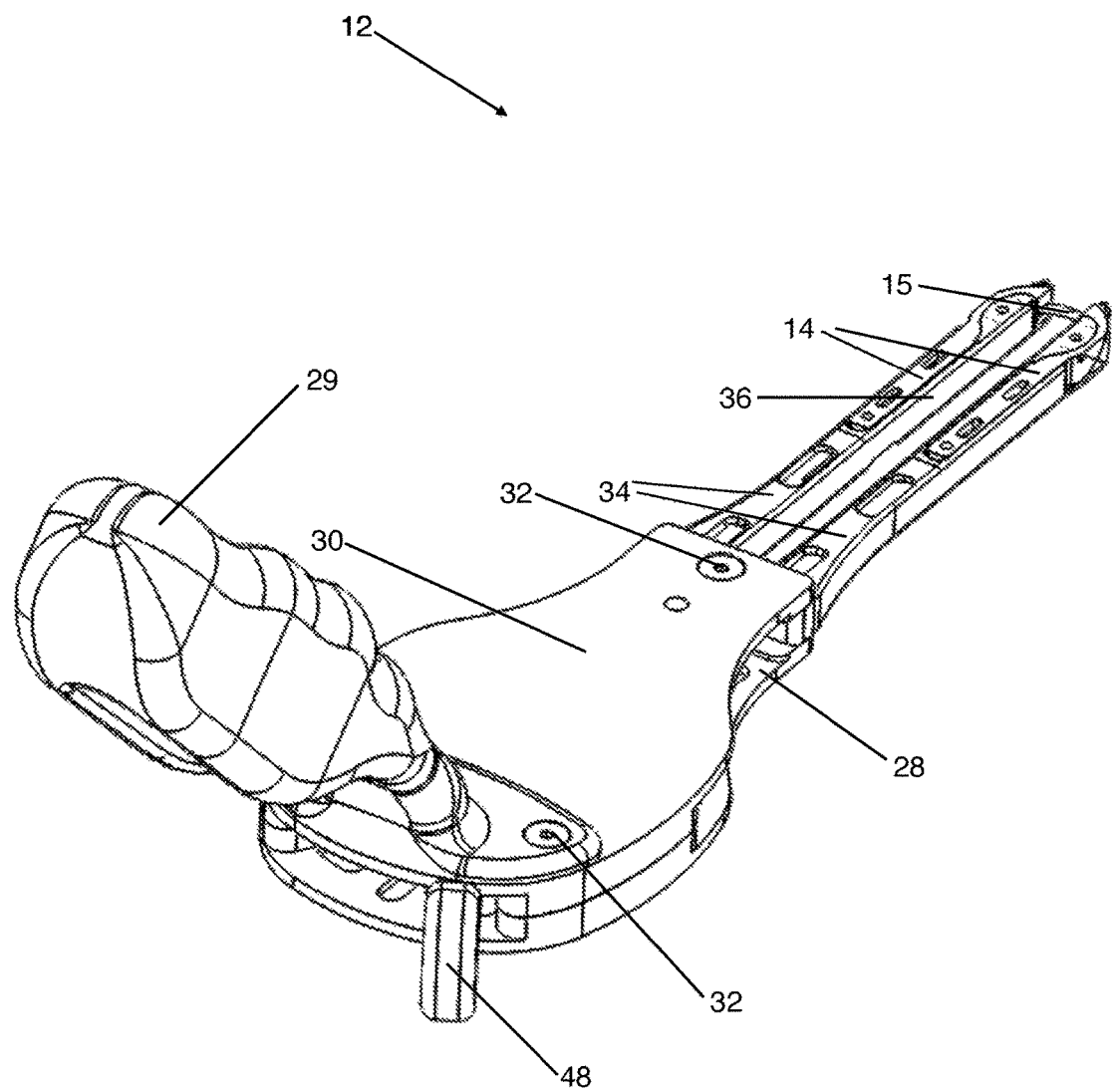
Figure 16C:
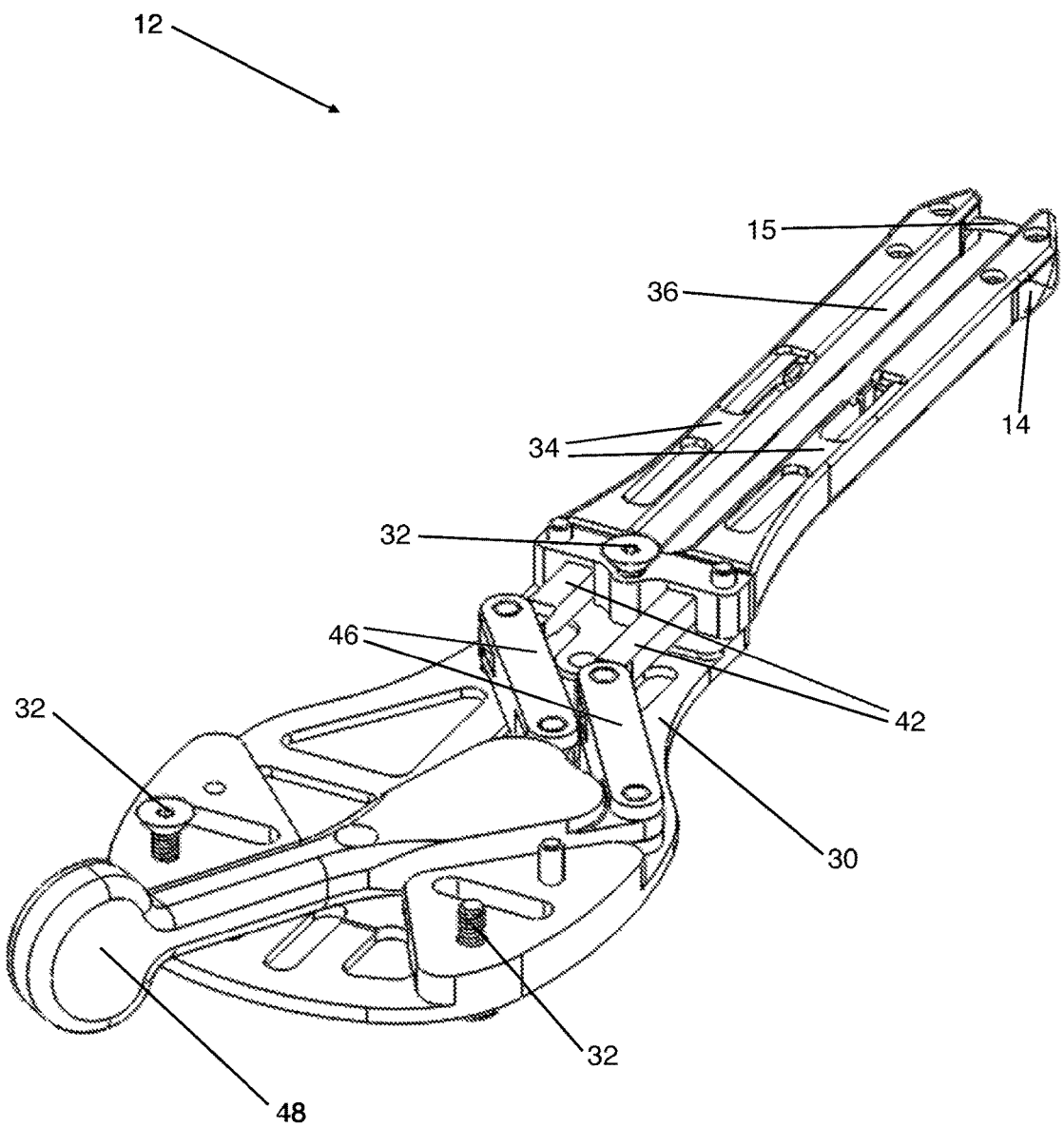
FIGS. 16C-16D are exploded perspective views of the suture activation assembly of FIG. 14.
Figure 16D:
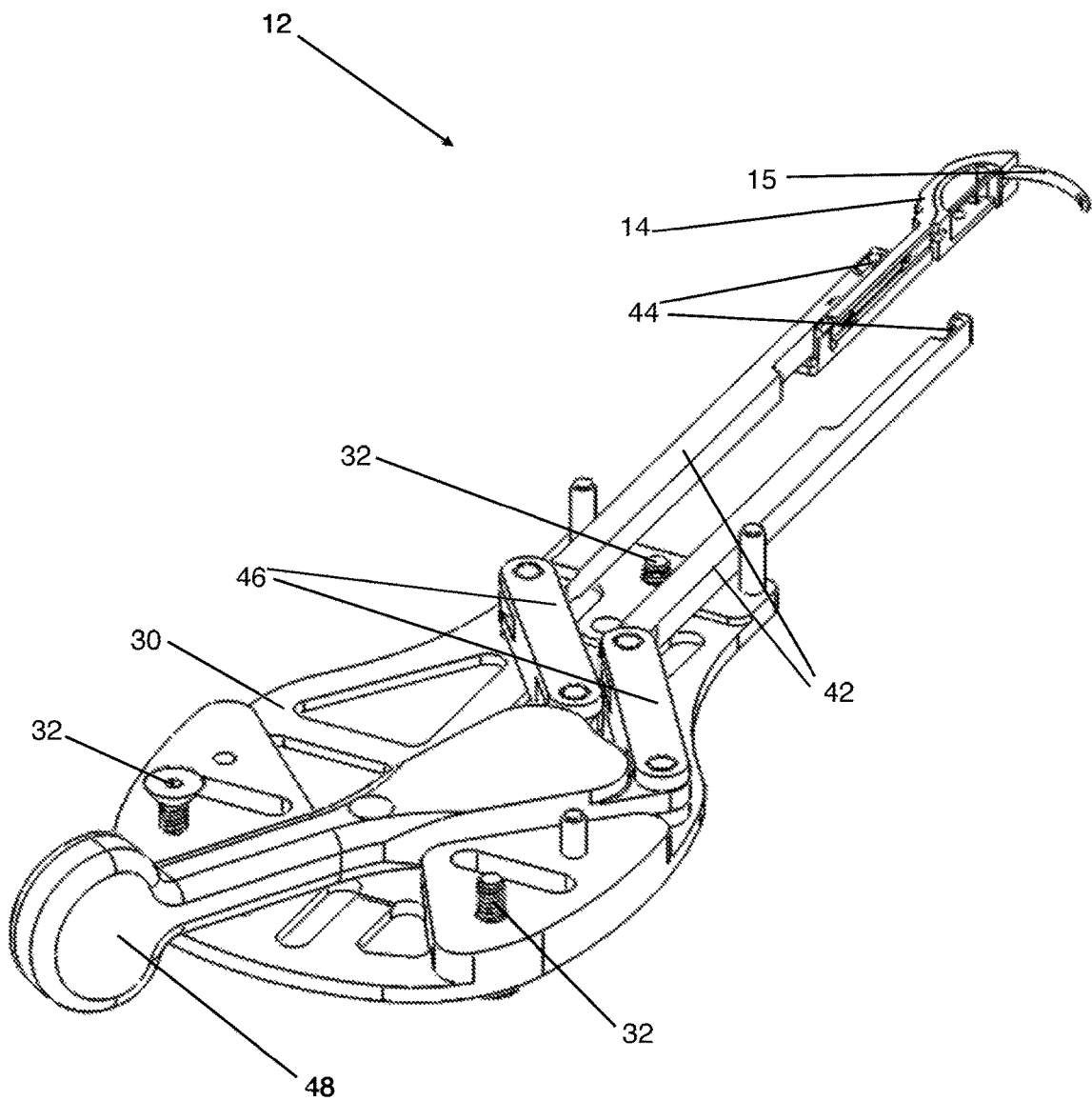
Figure 16E:
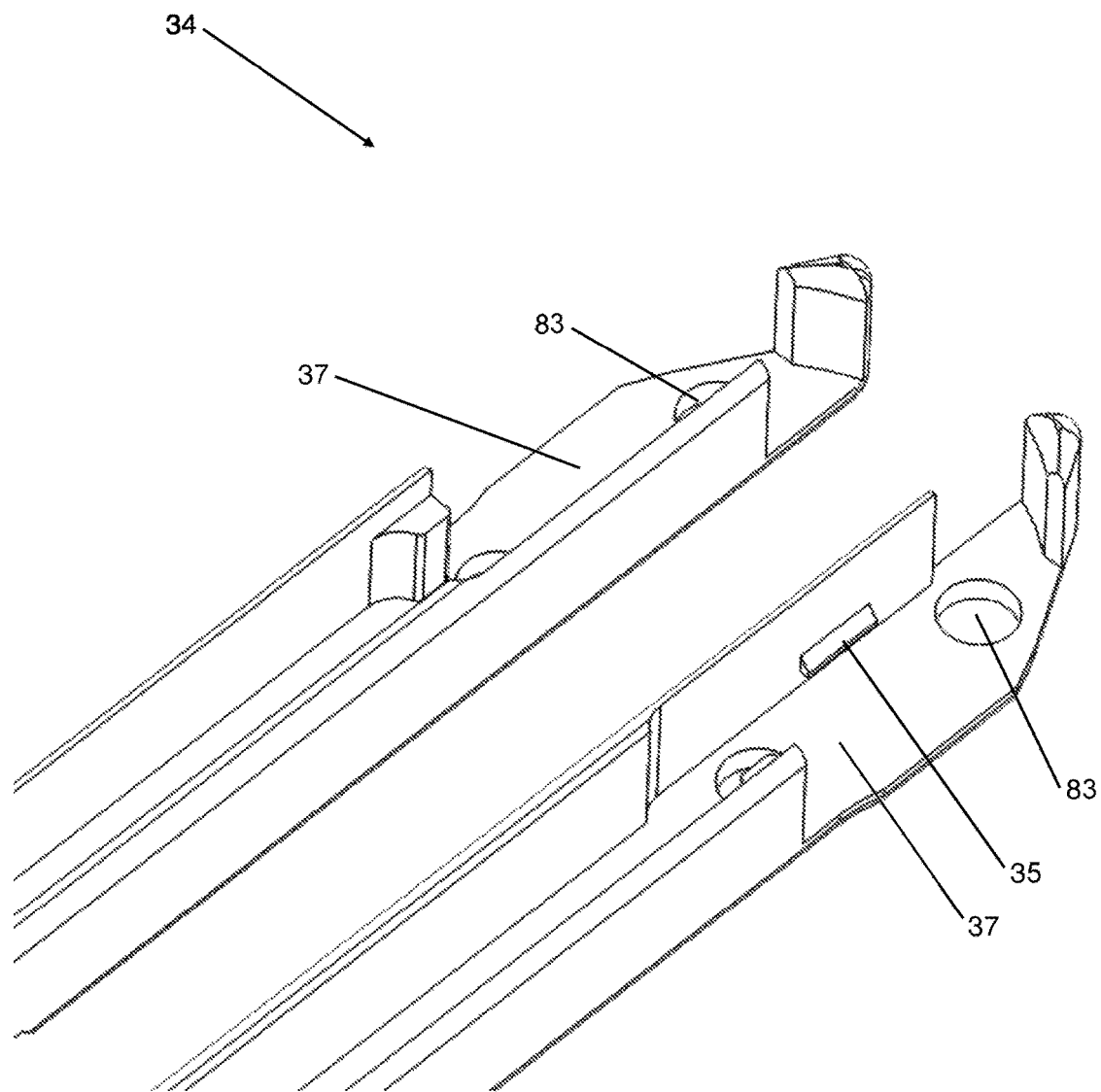
FIG. 16E is a detailed perspective view of a suture activation arm of the suture activation assembly of FIG. 14.

An embodiment of a suture activation assembly 12 and its various components are illustrated in FIGS. 16A-16D. The suture activation assembly 12 may be made of stainless steel, titanium, rigid plastic, or any other material suitable for the application of a suture. The material may be able to undergo a sterilizing process, such as steam autoclave, radiation sterilization, or any other form of sterilization known in the art. Suture application handle assembly includes a superior housing 28 and an inferior housing 30. Superior 28 and inferior 30 housings are configured to retain and house internal mechanical components of the suture activation assembly 12 during operation. They are further configured to facilitate easy manipulation and positioning of the device by an operator during the procedure. It should be noted that the configuration of the superior 28 and inferior 30 housings allows for the tissue-manipulating cannula assembly 10 to be operated with either housing in the superior position. The superior 28 and inferior 30 housings are bound together with a number of fasteners 32. The suture activation assembly 12 may further include an actuating handle 29. For example, the actuating handle 29 may be constructed of titanium, steel, or any other material capable of withstanding an effective sterilization process. By way of example and not limitation, the actuating handle 29 may be attached to the inferior housing 30 by means of a number of fasteners 32. It may also be attached by any other means of attachment including, but not limited to, adhesives, welding, or any other means known in the art. The suture activation assembly 12 further includes multiple suture application arms 34. The suture application arms 34 are configured to be retained by a fastener 32 and connected to superior 28 and inferior 30 housings. The suture application arms 34 are further configured to retain a number of disposable suture housing assemblies 14. The disposable suture housing assemblies 14 may be placed in a housing-receiving space 37. A deforming bar 63 (FIGS. 17A-17B) on the disposable suture housing assembly 14 will deform and engage a housing clip 35 (FIG. 16E) on the suture application arms 34. The suture housing assemblies 14 are retained by the suture application arms 34 by means of a snap fit. The suture application arms 34 are further configured in a hollow geometry to allow for the passage of a number of driving members 42. The connection between a driving ribbon 56 (FIGS. 17A and 17C) of disposable suture housing assembly 14, the disposable suture housing assembly 14 being retained and constrained by the suture application arms 34, allows the suture to be driven through the tissue.

The suture application arms 34 each include a compression member abutment surface 36. The compression member abutment surface 36 allows the suture application arms 34 to engage in compression of the desired anatomy through first 16 and second 18 manipulating members. The suture application arms 34 retain a rigid geometry. When they are inserted and engage with first 16 and second 18 manipulating members, they may force the first 16 and second 18 manipulating members into a similar geometry, constraining the anatomy in a desired position for suturing. The suture application arms 34 further include a number of disposable assembly removal apertures, such as guide apertures 83. The assembly removal apertures are configured to receive a number of disposable assembly removal members (described below). These members allow the disposable suture housing assembly 14 to be removed from the suture activation assembly 12 with little effort on the part of the operator. The suture activation assembly 12 further includes a number of driving members 42. The driving members 42 each include a ribbon engagement notch 44. The ribbon engagement notch 44 is configured to engage with driving ribbon 56. Driving ribbon 56 is further configured to engage with suture needle 15. The alternate actuation of driving members 42 (described in greater detail below) allows the suture needle 15 to pass between the suture application arms 34. The suture activation assembly 12 further includes a number of linkages 46. The linkages 46 connect the driving member 42 with a driving lever 48. The linkages 46 are connected to the driving lever 48 by means of an articulating joint. The articulating joint may include a number of prominent appendages on the driving lever 48 to allow for easier engagement with a number of spaces disposed at either end of the linkages 46. The driving lever 48 may include a similar geometry of prominent appendages. The linkages 46 are further connected to the driving members 42 by means of an articulating joint. The driving lever 48 is connected to both linkages 46, allowing the lever to actuate both linkages 46 as well as both driving members 42 simultaneously and in concert with each other. The actuation of driving lever 48 transfers force into the linkages 46, which is then transferred to driving members 42. The force is then transferred into the driving ribbon 56 by means of the ribbon engagement notch 44. This then actuates the suture needle 15 and allows the suture needle 15 to puncture the desired soft tissue and bone. Actuation of the driving lever 48 in one direction will pass the suture needle 15 between the suture application arms 34 in one direction. Actuation of the driving lever 48 in the opposite direction will pass the suture needle 15 between the suture application arms 34 in the opposite direction.

Figure 17A:
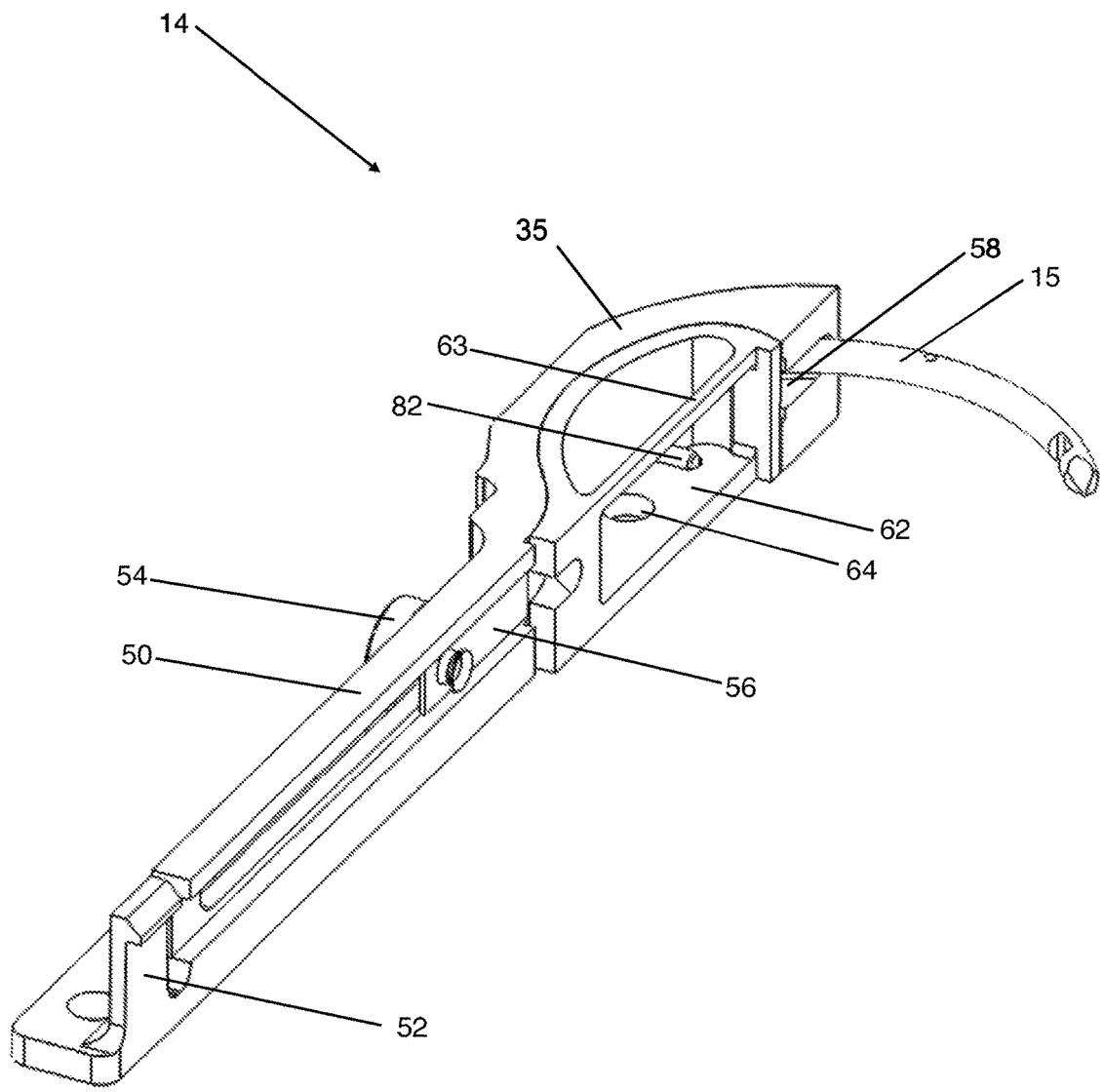
FIGS. 17A-17C are perspective views of a disposable suture housing assembly of the suture activation assembly of FIG. 14.
Figure 17B:
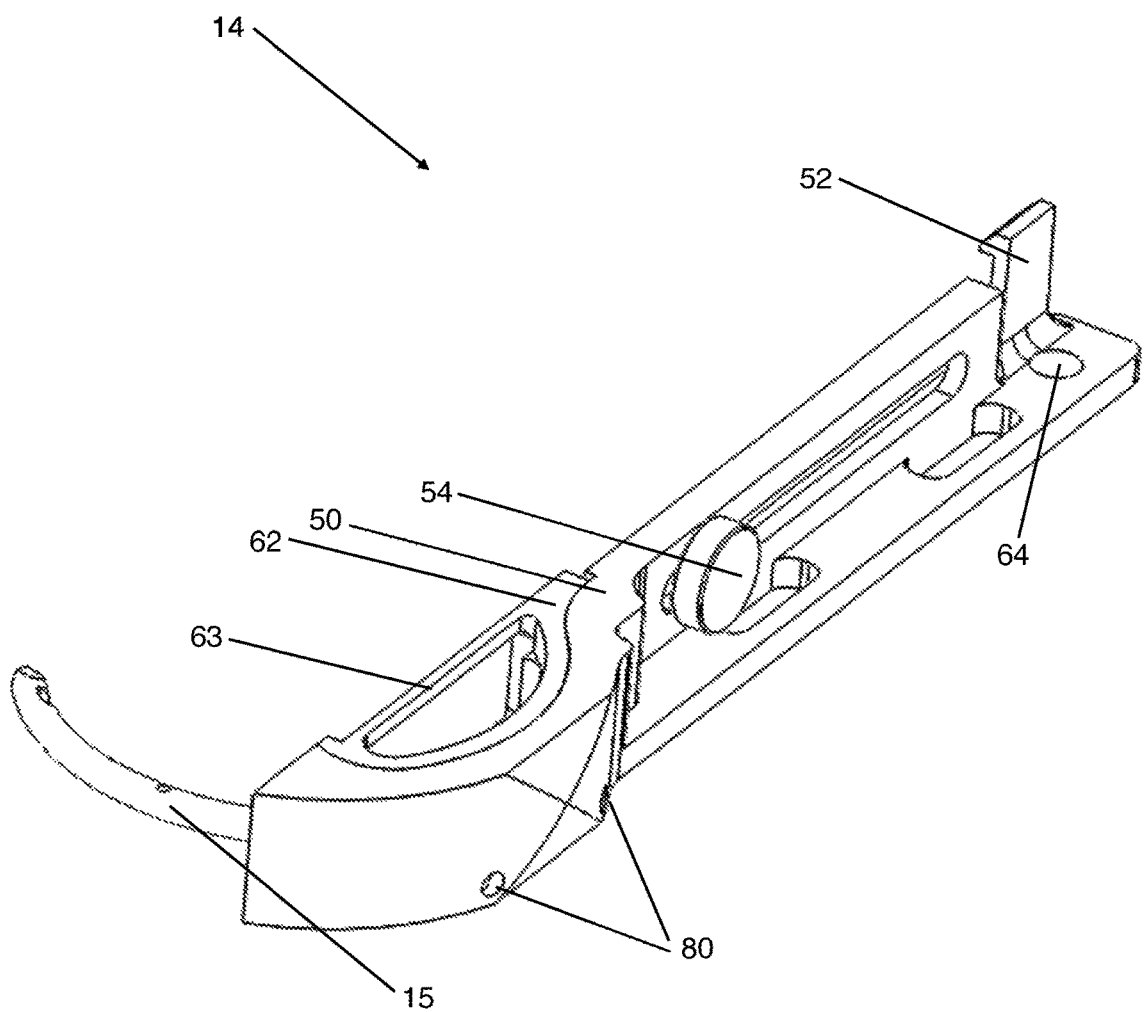
Figure 17C:
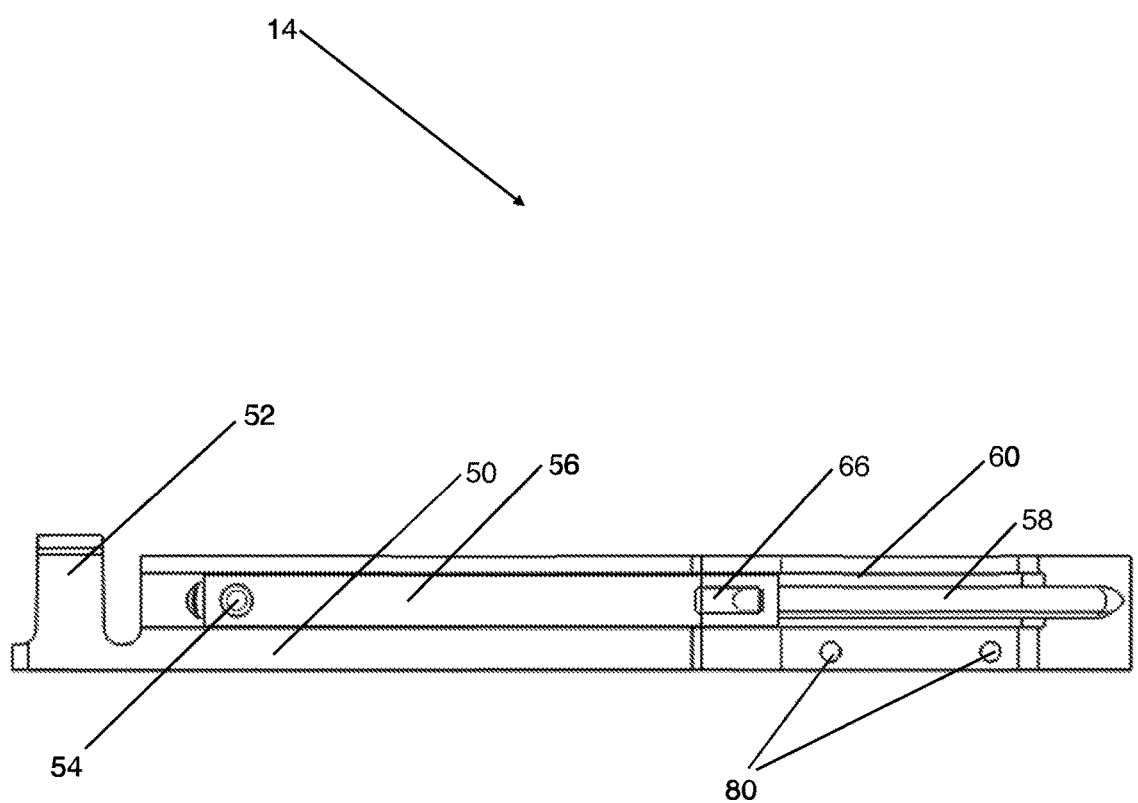

An embodiment of the disposable suture housing assembly 14 is illustrated in FIGS. 17A-17C. The various components of the suture housing assembly 14 may be made of plastic or any other material suitable to retain and protect a suture. The disposable suture housing assembly 14 includes a top needle track housing 50. The top needle track housing 50 is configured to hold and restrain the other components of the assembly as described below. The top needle track housing 50 includes an attachment snap hook 52. The attachment snap hook 52 is configured to engage with one of the suture application arms 34. The engagement between the attachment snap hook 52 and the suture application arms 34 retains the suture housing assembly 14 for the course of the procedure. It may then be disengaged and disposed of. The top needle track housing 50 further includes a suture needle track 58. The suture needle track 58 is configured to allow the suture needle 15 to be disposed within it. It should be noted that the suture needle 15 will be completely protected when disposed in the suture needle track 58. This allows for the protection of adjacent tissue from potential damage caused by the suture needle 15. It is further configured to allow the suture needle 15 to move through the passage when force is applied by the driving ribbon 56 as described below. The suture needle track 58 may then allow for both the pitching and catching of the suture needle 15 during the surgical procedure. The suture needle track 58 is further configured to house the suture needle 15 during the loading of the suture housing assembly 14 (described below). This allows the suture needle 15 to be disposed within the device before the procedure begins with a minimum of effort on the part of the operator. The top needle track housing 50 further includes a driving ribbon track 60. The driving ribbon track 60 is configured to allow the driving ribbon 56 to be disposed within it when the driving ribbon 56 is engaged by the driving members 42. It is further configured to allow movement of the driving ribbon 56 during engagement. This allows a full range of motion for the driving ribbon 56 during the pitching and catching of the suture needle 15. It should be noted that the driving ribbon track 60 and the suture needle track 58 have different geometries. This is to allow the driving ribbon 56 to engage with the suture needle 15 as long as possible while the suture needle 15 is still disposed in the suture needle track 58. The extended length of time the driving ribbon 56 engages the suture needle 15 allows more stability when the suture needle 15 is passed through the anatomical wall. It further hinders the suture needle 15 from wavering off course, ensuring a more stable capture of the suture needle 15 on the other side of the anatomical wall by the opposing driving ribbon 56. This process will be described in more detail below. The top needle track housing 50 further includes a number of alignment apertures 80. The alignment apertures 80 are configured to align with a separate set of alignment apertures 82 disposed on the bottom needle track housing 62. The alignment of both sets of alignment apertures 80, 82 allow the top 50 and the bottom 62 needle track housings to be properly aligned. A pin or similar device may then be placed through the alignment apertures 80, 82 to make the alignment permanent. This then ensures the proper operation of the device. The disposable suture housing assembly 14 further includes a ribbon driving button 54. The ribbon driving button 54 is configured to engage on one end with a driving ribbon 56 and on the other with a ribbon engagement notch 44 of a driving member 42. This engagement allows the force from the driving member 42 to be transferred into the driving ribbon 56 and then into the suture needle 15. The disposable suture housing assembly 14 further includes a bottom needle track housing 62. The bottom needle track housing 62 is configured to restrain the driving ribbon 56 into the driving ribbon track 60 during engagement from a driving member 42. The driving ribbon 56 may be guided along the path of the driving ribbon track 60, ensuring that the driving ribbon 56 has a full range of motion to manipulate the suture needle 15. The bottom needle track housing 62 further includes a deforming bar 63. The deforming bar 63 is configured to engage with the housing clip 35 on a suture application arm 34. The deforming bar 63 will be bent as the disposable suture housing assembly 14 is attached to the suture application arm 34. The deforming bar 63 will them snap back into place below the housing clip 35, creating an effective snap fit that will help retain the disposable suture housing assembly 14 at the distal end of the device. Bottom needle track housing 62 includes a loading retention aperture 64. The loading retention aperture 64 is configured to engage with loading clips 78 (FIG. 19A) during the loading of the disposable suture housing assembly 14 into the suture activation assembly 12. The top needle track housing 50 also includes a loading retention aperture 64 for an identical purpose. The disposable suture housing assembly 14 includes a driving ribbon 56 as has been noted above. The driving ribbon 56 includes a suture needle capture slot 66. The suture needle capture slot 66 is configured to engage with a driving ribbon engagement slot 72 of suture needle 15 (not clearly visible in the figure; see FIG. 18 for reference). This allows the driving ribbon 56 to engage and disengage with the suture needle 15 during the procedure. It is further configured to both push and pull the suture needle 15 depending on the force applied from driving member 42. It should also be noted that, as described above, the operation of the driving ribbon 56 requires that the driving ribbon 56 be made of a flexible and durable material. This material may be nitinol, spring stainless steel, or any durable material capable of elastic deformation.

Figure 18:
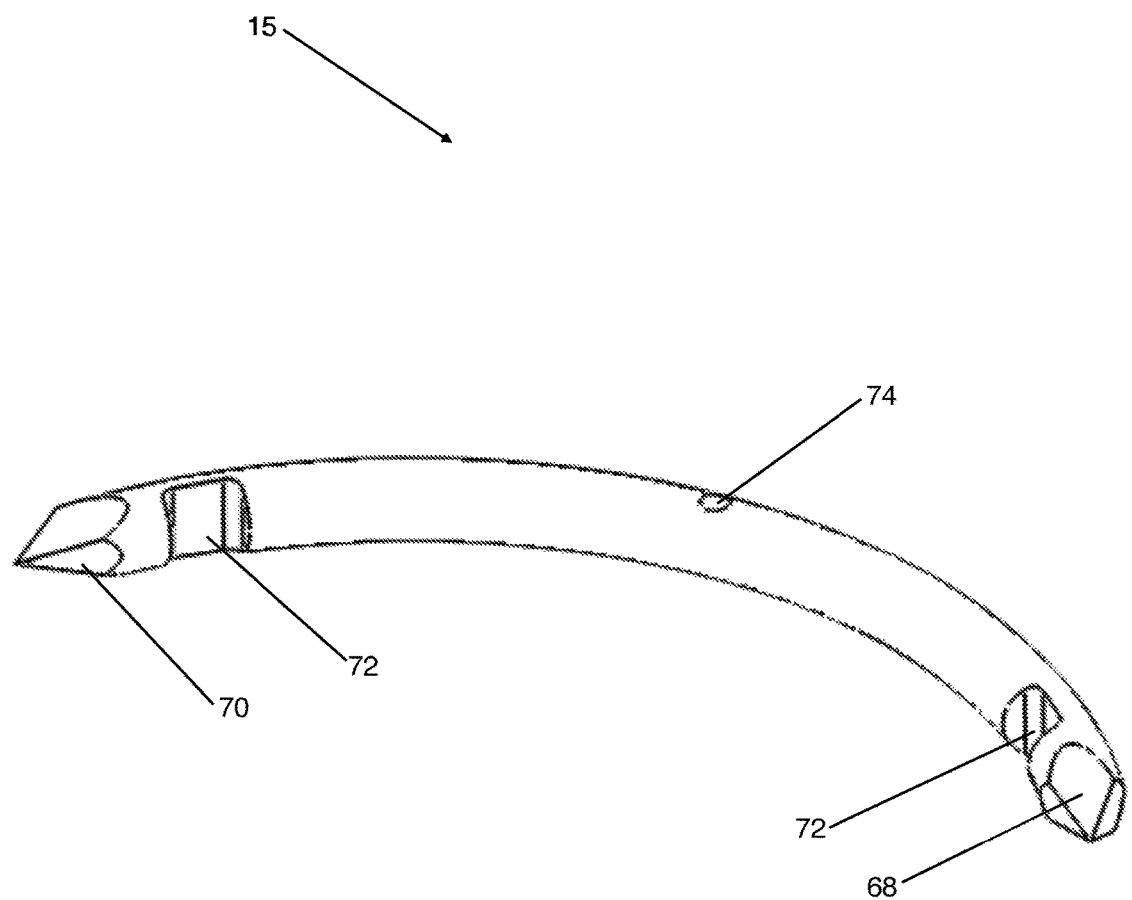
FIG. 18 is a perspective view of a suture needle of the suture activation assembly of FIG. 14.

An embodiment of the suture needle 15 is illustrated in FIG. 18. The suture needle 15 may be made of stainless steel, titanium, or any other material suitable to puncture soft tissue and/or bone without substantial deformation. The suture needle 15 is curved in shape. It includes a first puncturing end 68 and a second puncturing end 70. The first 68 and second 70 puncturing ends are configured to penetrate an anatomical wall or other piece of soft tissue or bone. They are further configured to allow an application and a return of suture needle 15 without the necessity of rotating the suture needle 15 for application back through the anatomical wall. The first puncturing end 68 may penetrate and pass through an anatomical wall. Once the suture needle 15 is completely on the other side of the anatomical wall, the second puncturing end 70 may penetrate and pass back through the anatomical wall. The suture needle 15 further includes a number of driving ribbon engagement slots 72. The driving ribbon engagement slots 72 are configured to engage with the suture needle capture slot 66 of driving ribbon 56. The driving ribbon engagement slots 72 are further configured to allow the driving ribbon 56 to both push and pull the suture needle 15. This allows for the application and return of the suture needle 15 as described above. A full description of this method is described below. The suture needle 15 further includes a suture attachment aperture 74. The suture attachment aperture 74 is configured to allow the attachment of a suture (not shown) to the suture needle 15. This may be achieved through a knot in the suture or any other means applicable to the art. It will be recognized by those familiar in the art that the suture attachment aperture 74 may include more than one suture passage space. They will further recognize that more than one suture may be passed through one or more suture attachment apertures 74. This may allow for a various number of sutures to be passed with the single suture needle 15.

Figure 19A:
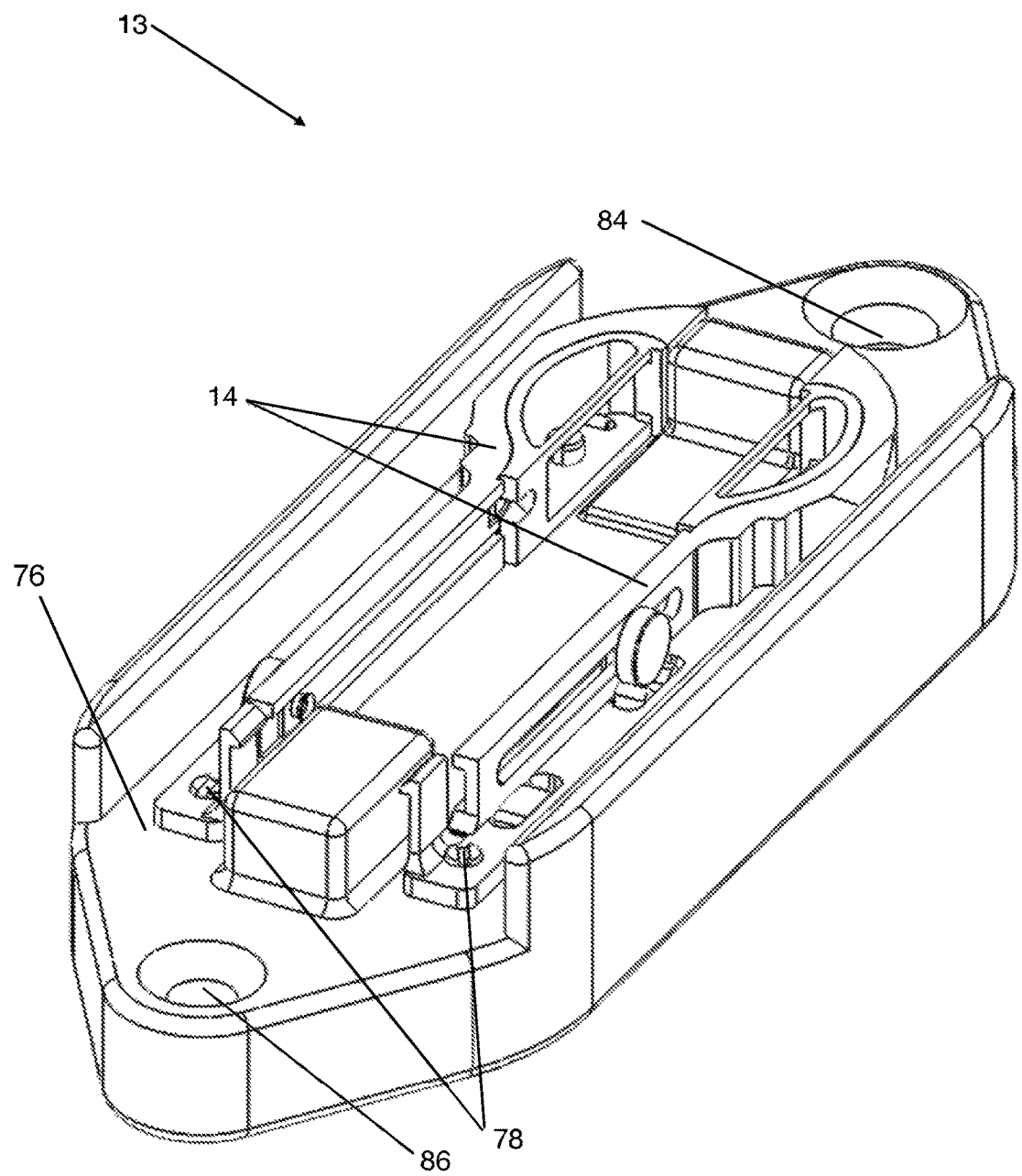
FIG. 19A is a perspective view of a disposable assembly application block coupled with a number of disposable suture housing assemblies.
Figure 19B:
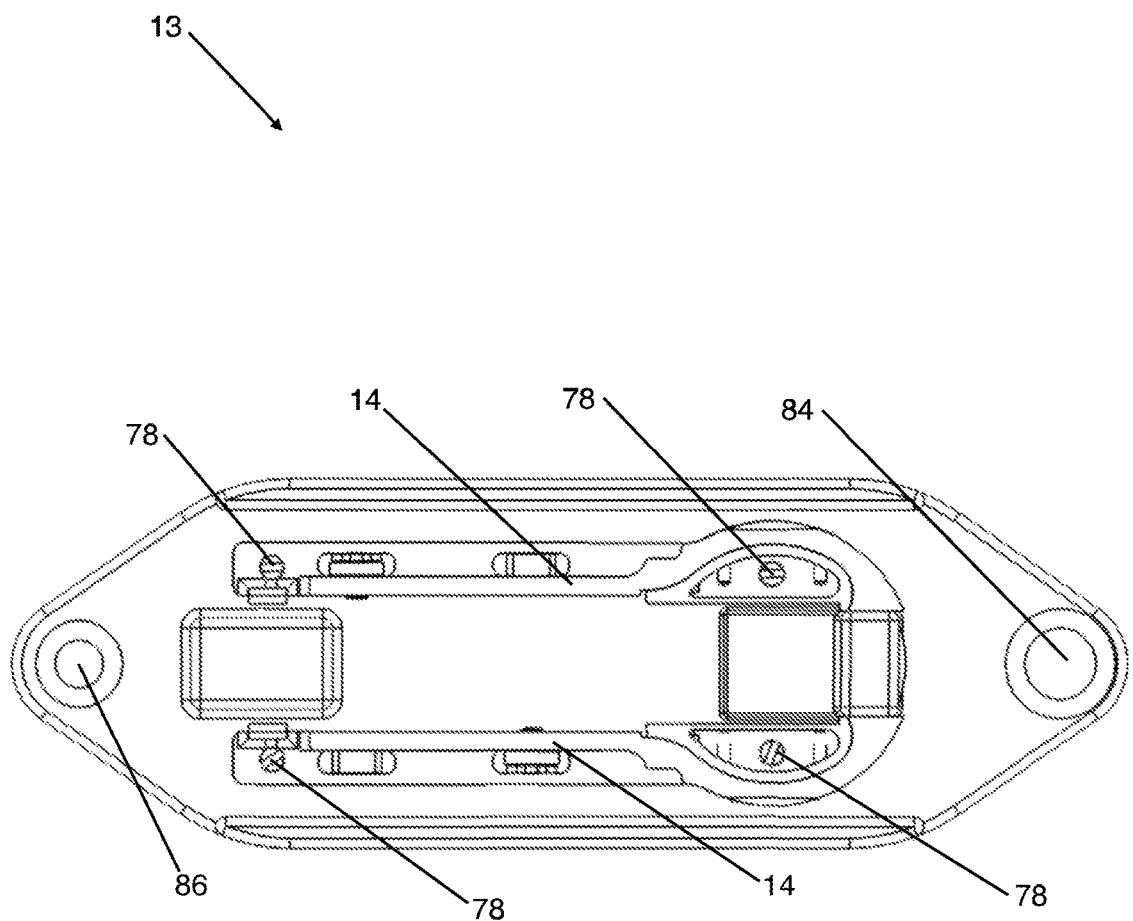
FIG. 19B is a top view of the disposable assembly application block of FIG. 19A.
Figure 19C:
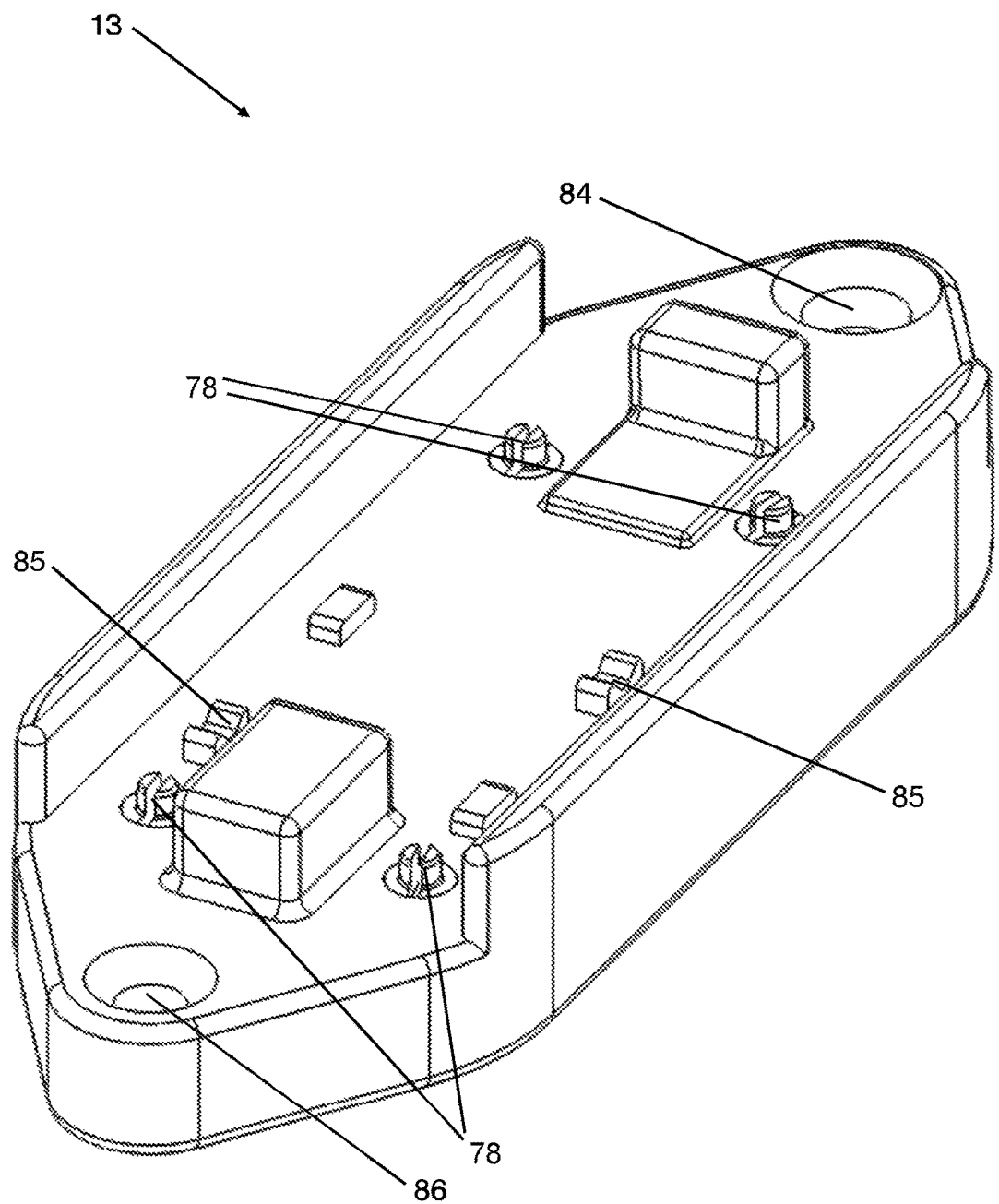
FIG. 19C is a perspective view of the disposable assembly application block of FIG. 19A.
Figure 20A:
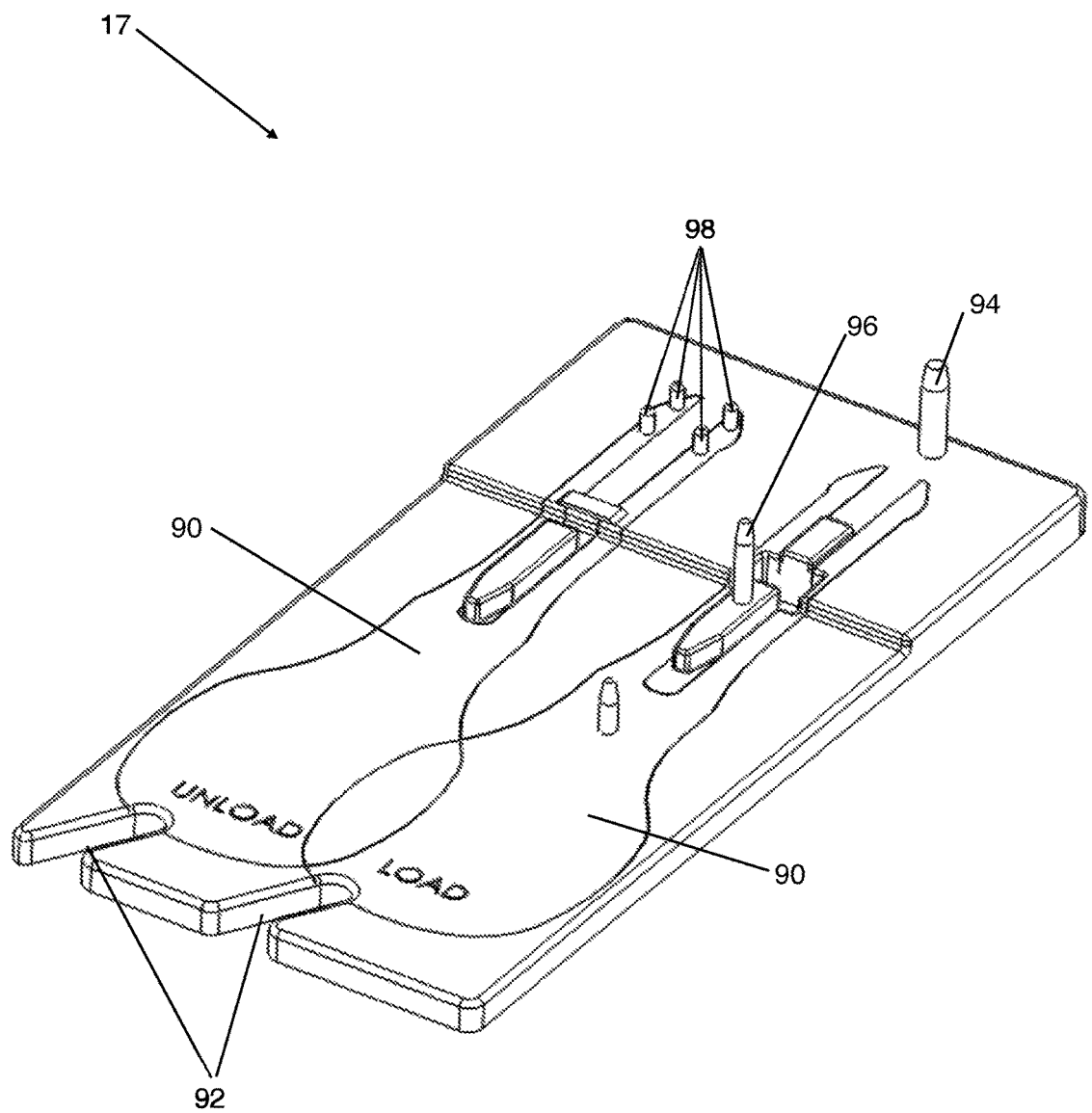
FIG. 20A is a perspective view of a suture housing loading/unloading plate.
Figure 20B:
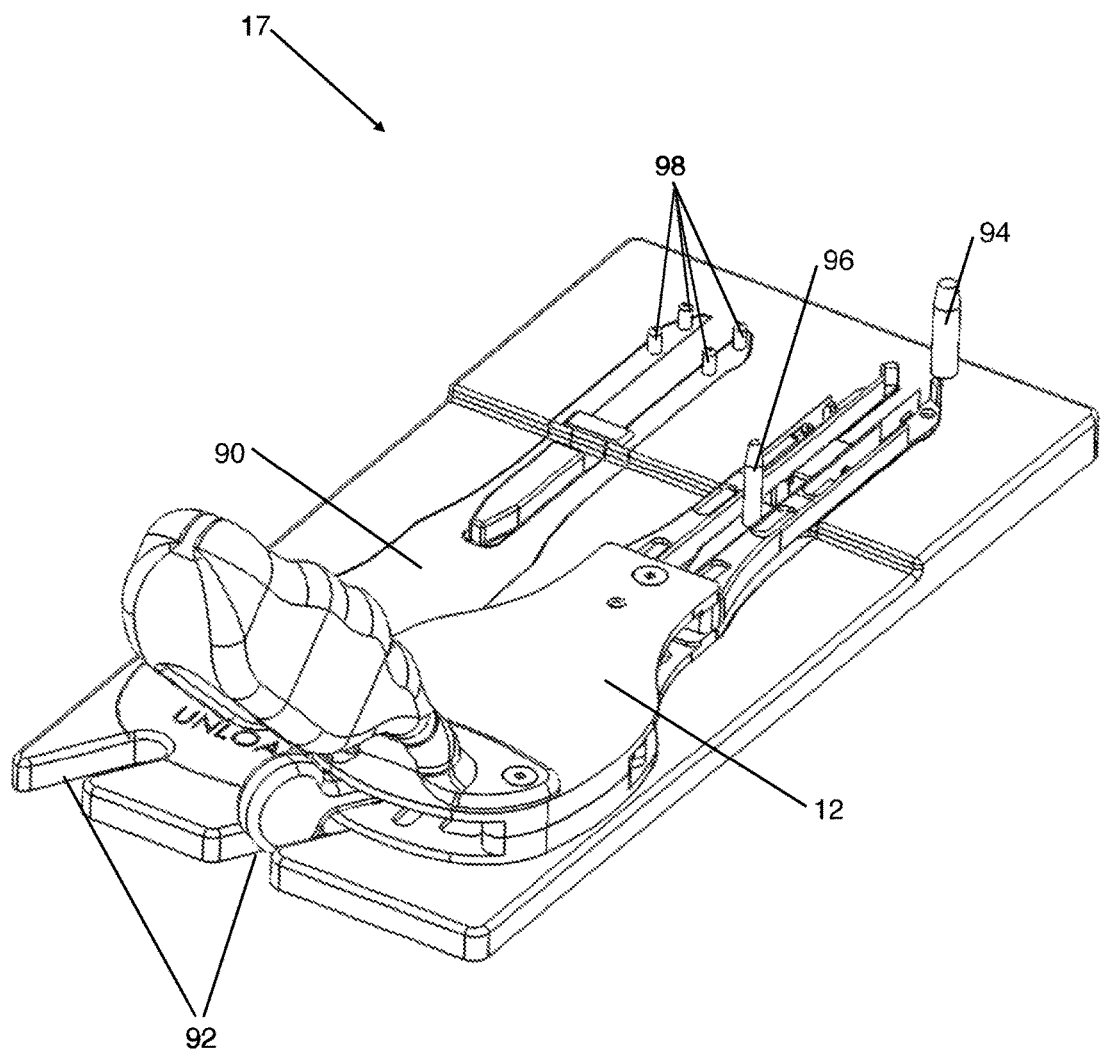
FIGS. 20B-20C are perspective views of the suture housing loading/unloading plate of FIG. 20A with a suture activation assembly in the process of having a number of disposable suture housing assemblies applied.
Figure 20C:
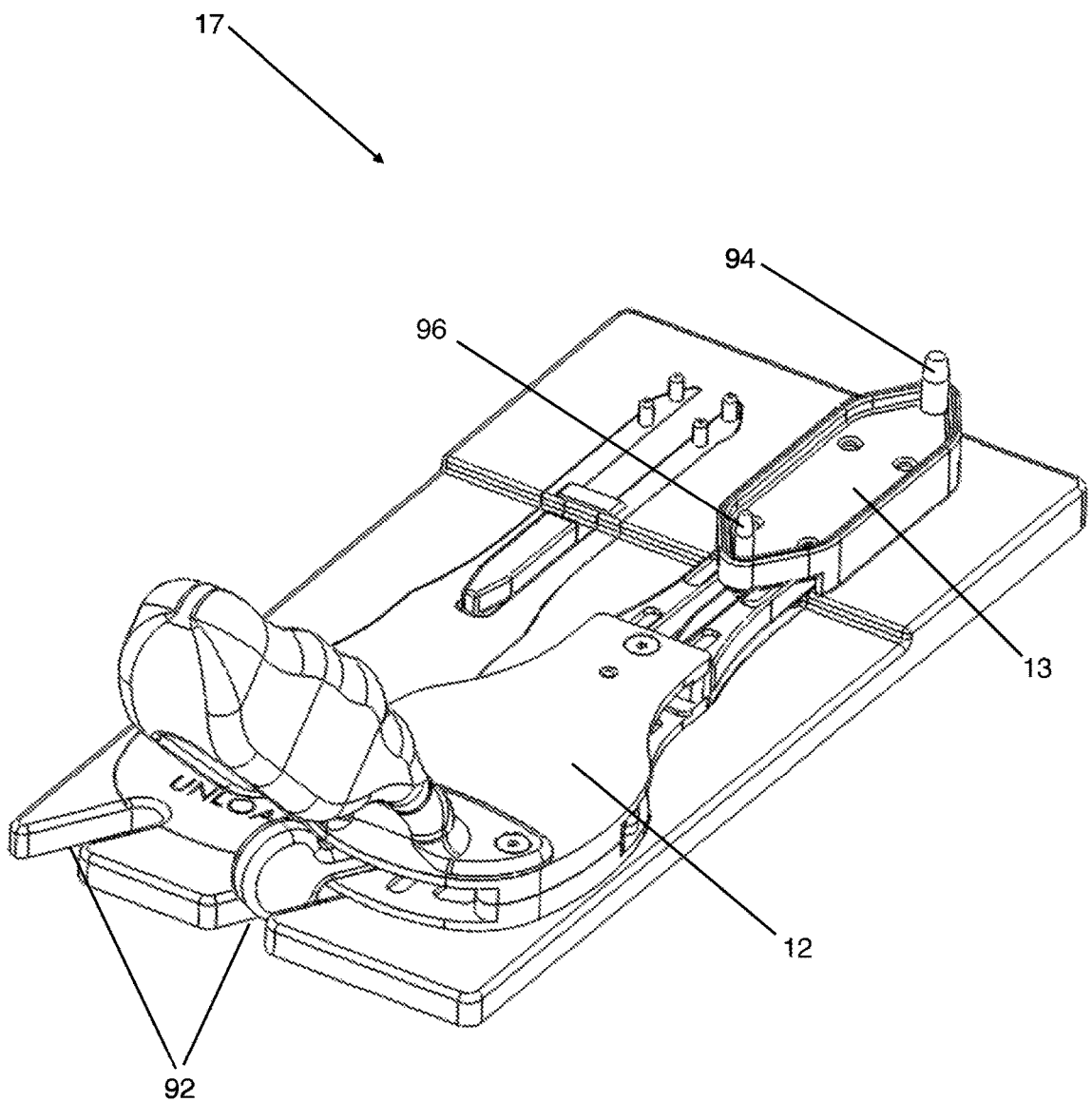
Figure 20D:
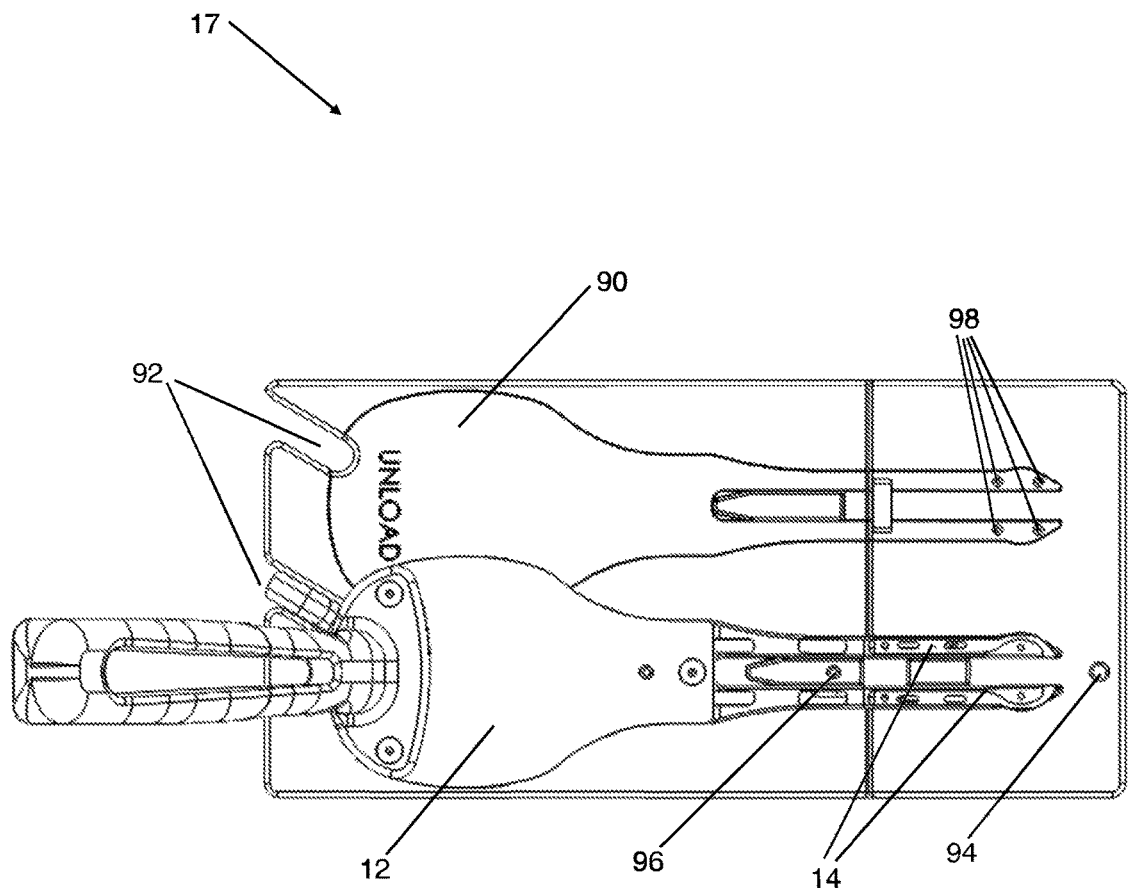
FIG. 20D is a top view of the suture housing loading/unloading plate of FIG. 20A with a suture activation assembly having a number of disposable suture housing assemblies applied.

An embodiment of a disposable assembly application block 13 is illustrated in FIGS. 19A-19C. The disposable assembly application block 13 may be made of rigid plastic or any other material suitable for applying a number of disposable suture housing assemblies 14. The disposable assembly application block 13 includes a disposable assembly application body 76. The disposable assembly application body 76 is configured to allow the disposal of a number of disposable suture housing assemblies 14 on its superior surface. These disposable suture housing assemblies 14 are retained on the disposable assembly application body 76 by a number of loading clips 78. The loading clips 78 are configured to retain the disposable suture housing assemblies 14 while they are applied to the suture application arms 34 of the suture activation assembly 12. The disposable suture housing assemblies 14 may be retained on the suture application arms 34 as previously described. The retention clips present on the disposable suture housing assembly 14 allows the disposable suture housing assembly 14 to be lifted from the disposable assembly application block 13 once it has been engaged by the suture activation assembly 12. The purpose of the disposable assembly application block 13 is to allow easy assembly of a device for the medialization of the turbinate. The suture needle 15 will have already been loaded into the disposable suture housing assembly 14 and, thereby, protected from injuring tissue during the procedure. The disposable assembly application block 13 further includes a number of ribbon configuration guides 85. The ribbon configuration guides 85 are configured to engage with a number of ribbon driving buttons 54 of the disposable suture housing assemblies 14. This will ensure that the driving ribbon 56 of the disposable suture housing assembly 14 will be in a proper orientation to protect and retain the suture needle 15. The disposable assembly application block 13 further includes a large guide aperture 84 and a small guide aperture 86. The large 84 and small 86 guide apertures are configured to guide the disposable assembly application block 13 into a proper coordination to allow for application of the disposable suture housing assemblies 14. The large 84 and small 86 guide apertures have different geometries to ensure that the disposable assembly application block 13 is in the correct orientation. The large 84 and small 86 guide apertures are further configured to have geometries similar to a number of guide members of a suture housing loading/unloading plate 17 (described below). The engagement between these guide members and the large 84 and small 86 guide apertures aligns the disposable assembly application block 13 for the application of its disposable suture housing assemblies 14.

An embodiment of a suture housing loading/unloading plate 17 is illustrated in FIGS. 20A-20D. The suture housing loading/unloading plate 17 may be made of plastic, steel, or any other material suitable for the loading and unloading of a number of disposable suture housing assemblies 14. The material may be further able to undergo a sterilizing process, such as steam autoclave, radiation sterilization, or any other form of sterilization known in the art. The suture housing loading/unloading plate 17 includes a number of suture activation assembly guides 90. The suture activation assembly guides 90 are configured to receive and guide the suture activation assembly 12 during the loading and unloading of the disposable suture housing assemblies 14. The suture housing loading/unloading plate 17 further includes a number of driving lever guides 92. The driving lever guides 92 are configured to guide driving lever 48 into a position for the loading and unloading of the disposable suture housing assemblies 14. The position of the driving lever 48 enables the suture needle 15 to remain securely in the disposable suture housing assembly 14 and, in addition, enables the internal geometry of the suture activation assembly 12 to receive and activate the internal geometry of the disposable suture housing assembly 14. The suture housing loading/unloading plate 17 further includes a large guide member 94 and a small guide member 96. The large 94 and small 96 guide members are configured to engage with the large 84 and small 86 guide apertures, respectively, of disposable assembly application block 13. The engagement between the large 94 and small 96 guide members and the large 84 and small 86 guide apertures ensures that the disposable assembly application block 13 is properly aligned with the suture activation assembly 12 (disposed in a suture activation assembly guide 90) in order to load a number of disposable suture housing assemblies 14 into the suture activation assembly 12. As noted in the description of the disposable assembly application block 13, the disposable suture housing assemblies 14 may be deposited securely into the suture activation assembly 12 before the assembly application block 13 is removed and disposed of. The suture housing loading/unloading plate 17 further includes a number of disposable assembly removal members 98. The disposable assembly removal members 98 are configured to be received by a number of disposable assembly removal apertures 88 of the suture activation assembly 12. The purpose of this configuration is to allow the disposable assembly removal members 98 to contact the disposable suture housing assemblies 14. This contact will disengage the disposable suture housing assemblies 14 and allow the operator to dispose of them. The operator may place the suture activation assembly 12 with the disposable suture housing assembly 14 still attached into the suture activation assembly guides 90. By applying downward pressure, the operator will engage the disposable assembly removal members 98 through the disposable assembly removal apertures 88 and into contact with the underside of the disposable suture housing assemblies 14. This contact will force the disposable suture housing assemblies 14 out of engagement with the suture activation assembly 12 and allow for their disposal.

Figure 21A:
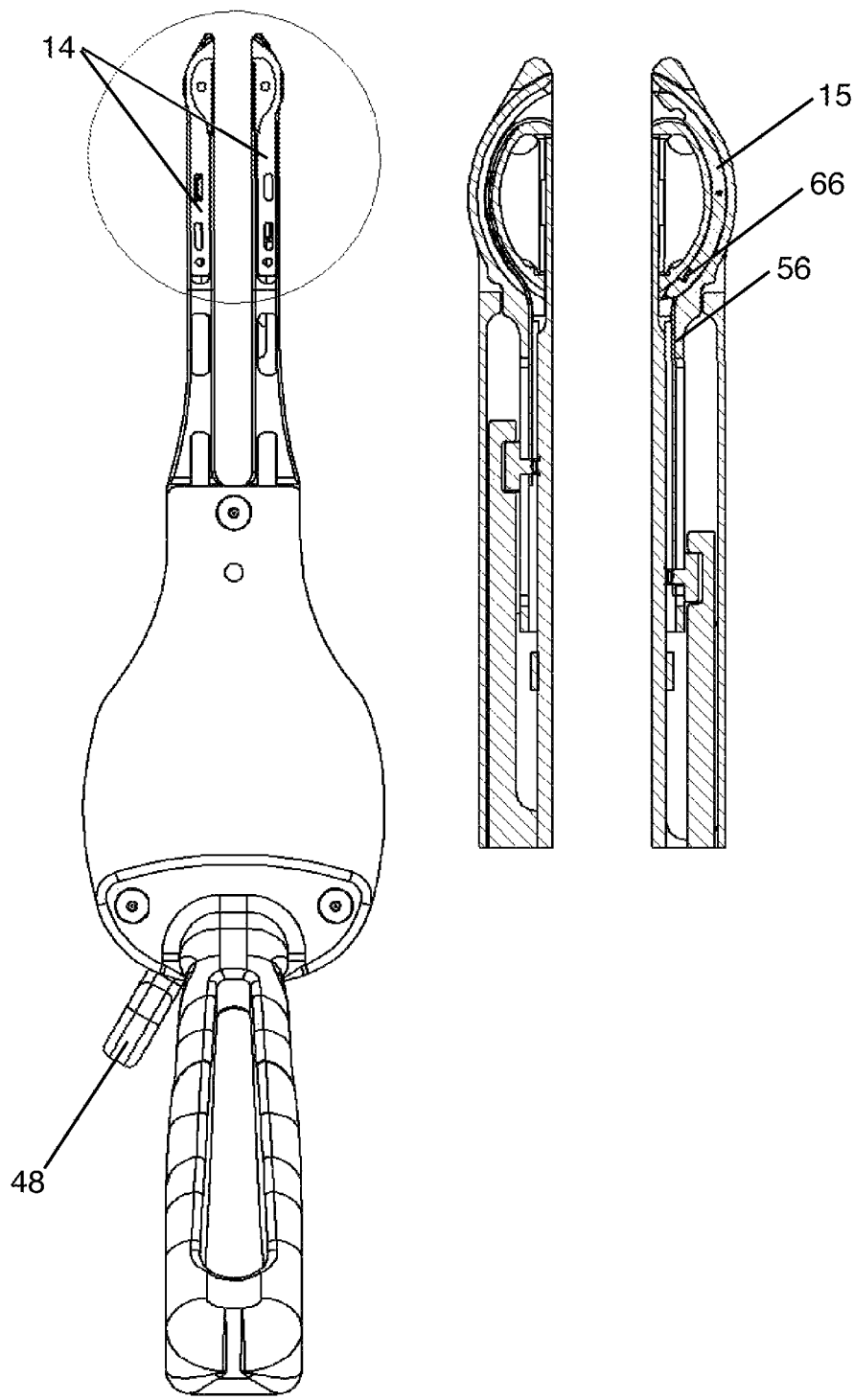
FIGS. 21A-21E are top views and top detail section views of the suture activation assembly of FIG. 14 in various configurations of passing a suture from one disposable suture housing assembly and into another disposable suture housing assembly.
Figure 21B:
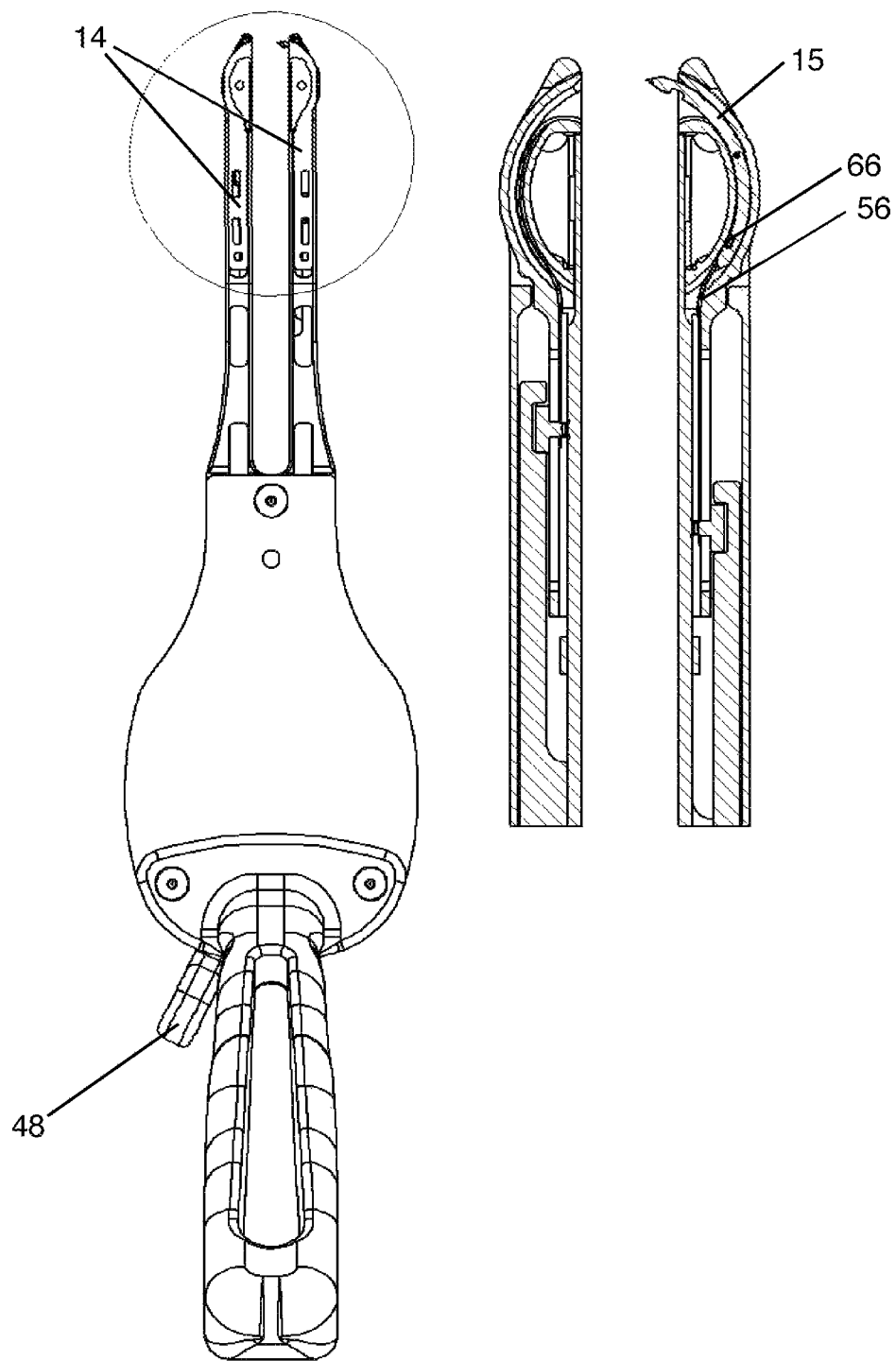
Figure 21C:
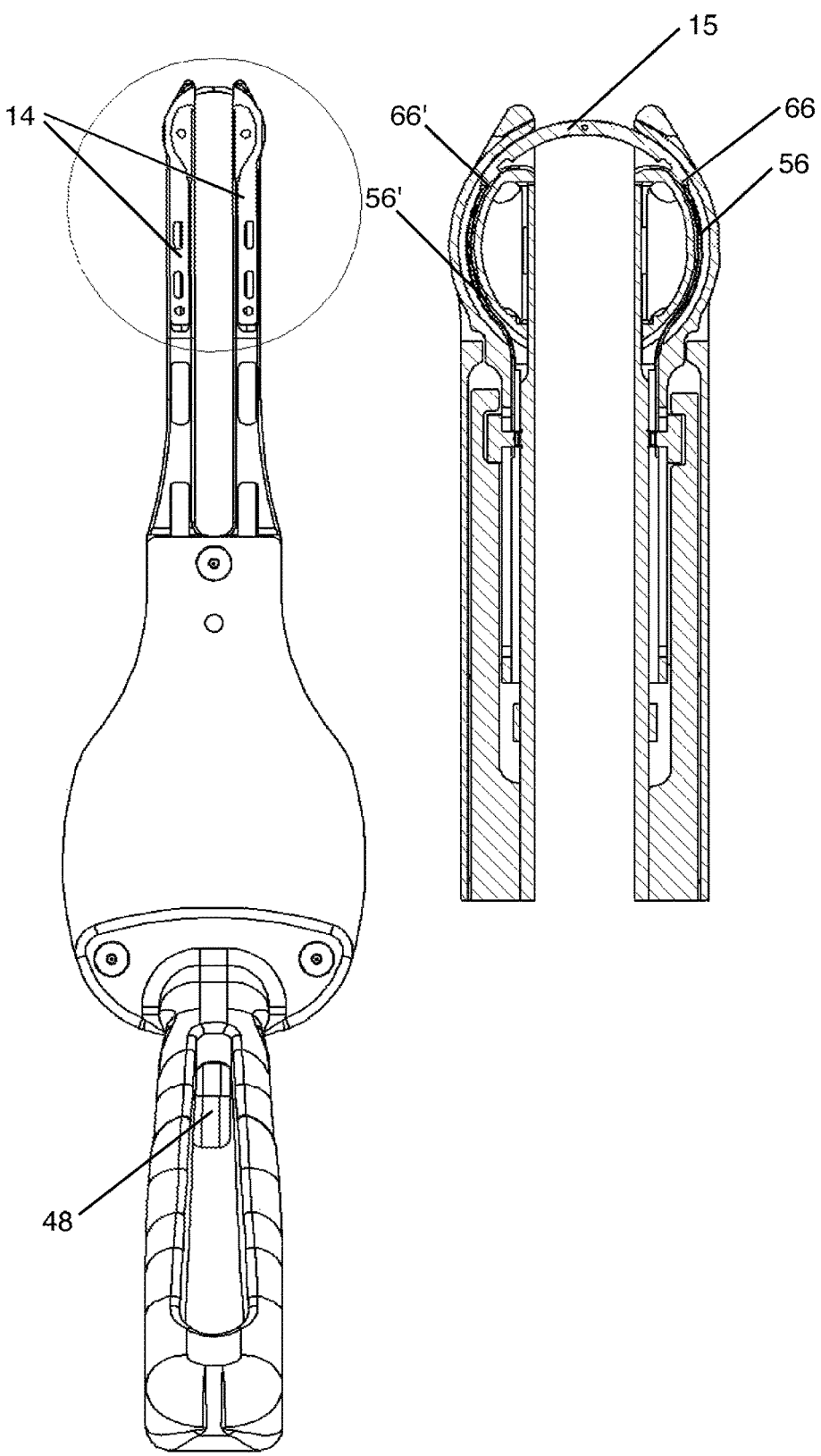
Figure 21D:
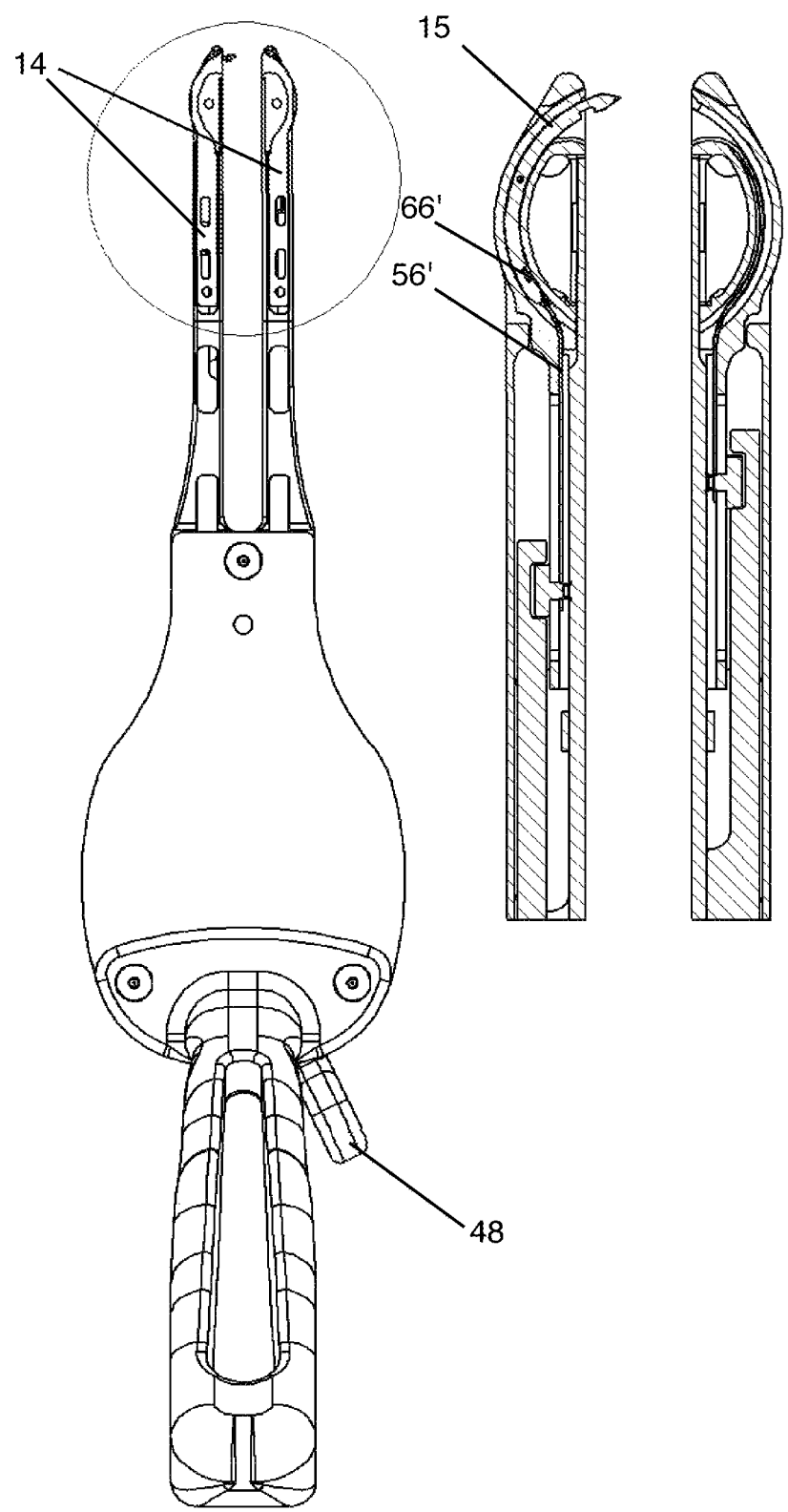
Figure 21E:
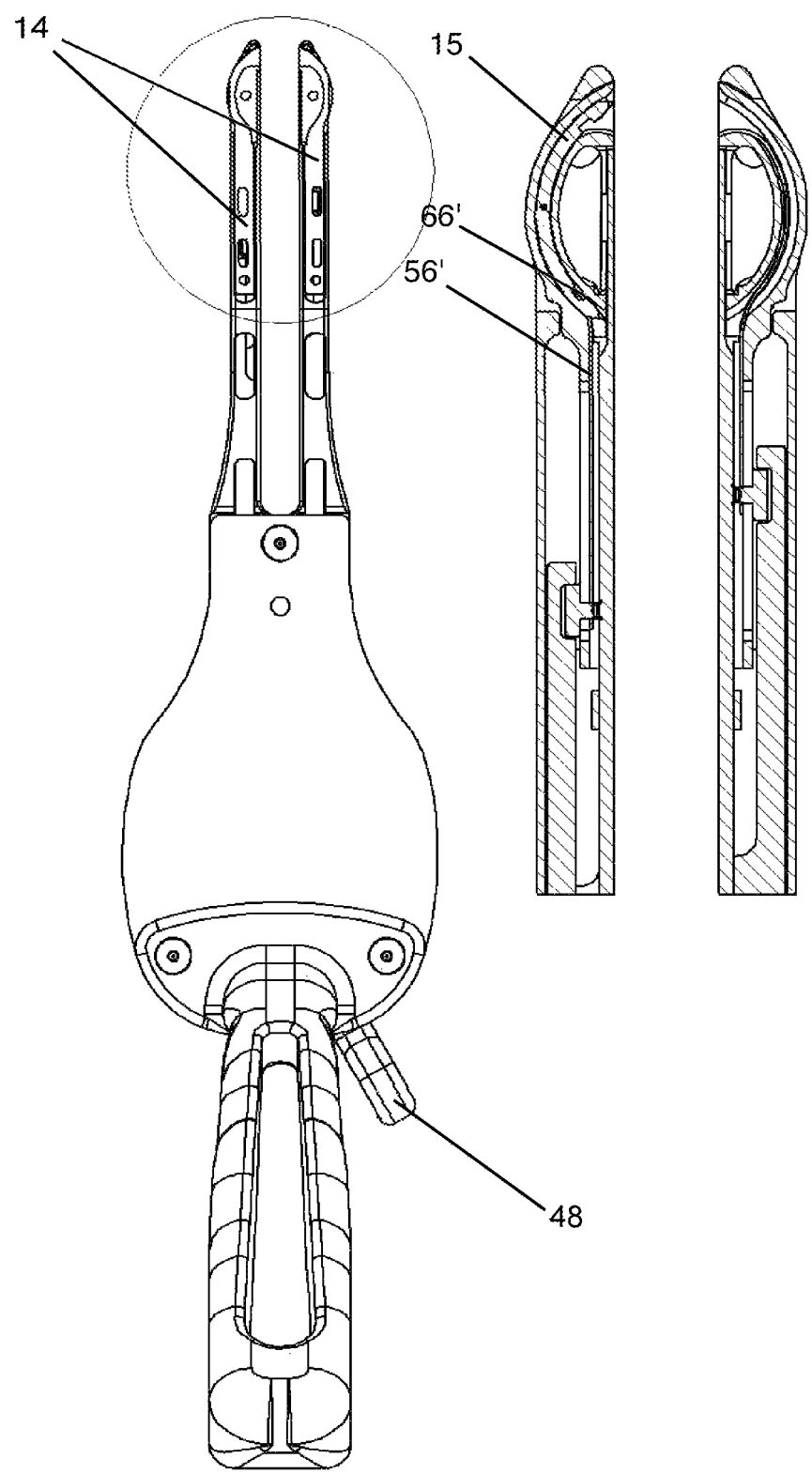

An embodiment of the passing of a suture needle 15 through an anatomical wall is illustrated in FIGS. 21A-21E. The initial position of the suture needle 15 is disposed and protected within the disposable suture housing assembly 14. The suture needle 15 is disposed within the suture needle track 58. The driving ribbon engagement slot 72 of the suture needle 15 is further engaged with the suture needle capture slot 66 of a first driving ribbon 56 (depicted in FIG. 21A). As the driving lever 48 is engaged and driving member 42 advances driving ribbon 56, suture needle 15 is advanced out of the suture needle track 58 and towards the opposing suture needle track (FIG. 21B). As this occurs, the opposing driving ribbon 56' is put in position to accept the suture needle 15 as it is advanced. At full advancement, the suture needle 15 is directly between the disposable suture housing assemblies 14. At this midpoint, the driving ribbon engagement slot 72 of the suture needle 15 has been disengaged from the suture needle capture slot 66. The driving ribbon 56 has been bent out of engagement with the suture needle 15 as it follows the driving ribbon track 60. Further, the opposing driving ribbon 56' has also been bent out of engagement. At this midpoint, neither the suture needle capture slot 66 nor the suture needle capture slot 66' is engaged with either driving ribbon engagement slot 72 or 72' (FIG. 21C). As the driving lever 48 is engaged further, the driving ribbon 56' is withdrawn and allowed to return to a position of engagement with the suture needle 15. The suture needle capture slot 66' is allowed to engage with the driving ribbon engagement slot 72'. This then allows the driving ribbon 56' to begin drawing the suture needle 15 into another suture needle track 58, as shown in FIG. 21D. As the driving lever 48 is engaged completely, the driving ribbon 56' withdraws the suture needle 15 completely into a disposable suture housing assembly 14. The suture needle 15 is now protected again (see FIG. 21E). This then allows the operator to relocate the suture activation assembly 12. The process described above may be repeated in reverse to pass the suture needle 15 back to its original position, carrying a suture thread with it and thus achieving effective suturing of soft tissue and/or bone.

To construct the suture passing device, take driving members 42 of suture activation assembly 12 (please refer to FIGS. 16A-16E when referencing construction). Connect them to linkages 46 by means of a screw, pin, or any other suitable device. Connect the linkages 46 to the driving lever 48 by means of a screw, pin, or any other suitable device. Dispose the suture application arms 34 around the driving members 42, allowing the driving members 42 to move within the suture application arms 34. Dispose this entire assembly on top of the inferior housing 30. Place the superior housing 28 on top such that it is aligned with the inferior housing 30. Attach the inferior 30 and superior 28 housings together using a number of fasteners 32. This will restrain the interior geometry of the suture activation assembly 12 and prepare it for receipt of a disposable suture housing assembly 14. The disposable suture housing assembly 14 may be constructed by taking a top needle track housing 50. A driving ribbon 56 may then be disposed into the driving ribbon track 60. A ribbon driving button 54 may then be attached to the driving ribbon 56. A bottom needle track housing 62 may then be attached to the top needle track housing 50, as was described above in reference to the disposable suture housing assembly 14. This will then allow the disposable suture housing assembly 14 to be attached to a disposable assembly application block 13. The application of the suture needle 15 may then be actuated as described above.

A method for preparing the surgical area, the procedure is disclosed as follows: the first manipulating member 16 of the tissue-manipulating cannula assembly 10 may be inserted into a first nasal cavity. The first manipulating member 16 may be inserted to a desired depth in the nasal cavity to restrain soft tissue such as, for example, a turbinate or loose tissue after a septoplasty. A second manipulating member 18 may then be inserted into a second nasal cavity. The second manipulating member 18 may be inserted to a desired depth in the second nasal cavity. It should be noted that these separate manipulating members need not be of similar geometry. Each may have a unique geometry dependent on the piece of tissue the operator desires to restrain and control. Once the first 16 and second 18 manipulating members have been separately applied, the first 16 and second 18 manipulating members may be coupled together using a connection interface 20. The connection interface, as disclosed above, uses a snap fit, allowing the first 16 and second 18 manipulating members to pivot around the point generated by the connection interface 20. It should be noted that the connection interface 20 may also have a series of other articulating features, allowing for additional pivotal or rotational motion around the point generated by the connection interface 20. Once first 16 and second 18 manipulating members have been coupled together using the connection interface 20, the suture activation assembly 12 may be applied to the surgical area. A number of suture application arms 34 may be inserted through a number of cannula-receiving apertures 24 of the tissue-manipulating cannula assembly 10. As described above, the insertion of the suture application arms 34 through the cannula-receiving apertures 24 will compress the first 16 and second 18 manipulating members onto the anatomy, holding the anatomy in place during the procedure. It should be noted that the compression of first 16 and second 18 manipulating members is not the only method for restraint of tissue. The first 16 and second 18 manipulating members may be configured to be attached directly to the anatomy, restraining and controlling it before the application of the suture activation assembly 12. Similarly, the first 16 and second 18 manipulating members may be configured to attach to an external piece of anatomy. This would not preclude an internal component that would control and restrain the tissue, but would rather allow for the first 16 and second 18 manipulating members to remain uncoupled while still restraining and controlling the inner anatomy. The rest of the procedure involving the passing of suture through soft tissue has been described above with reference to FIGS. 21A-21E.

Figure 22:
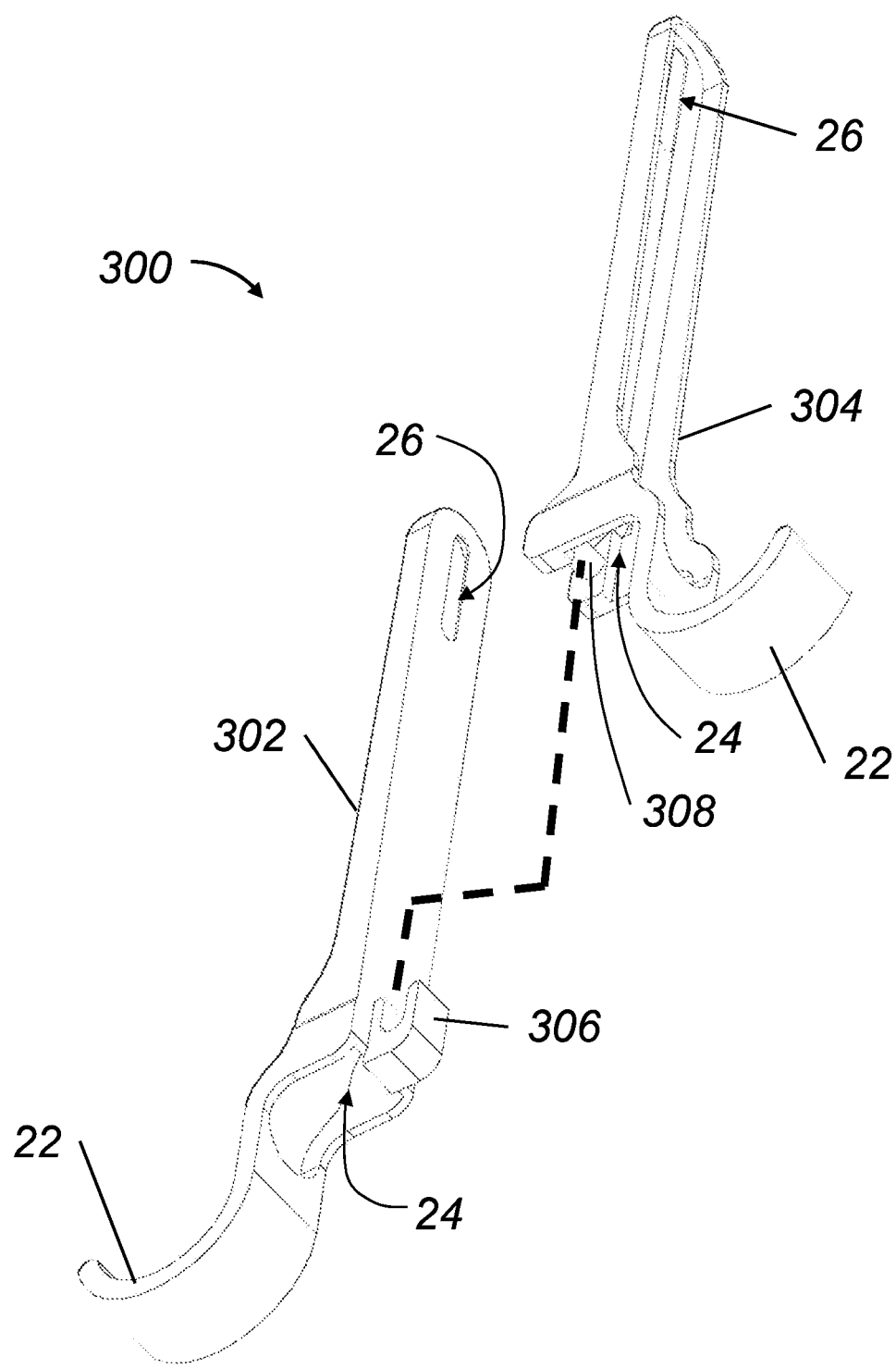
FIG. 22 is a perspective view of another example tissue-manipulating cannula assembly.

FIG. 22 depicts another example tissue-manipulating cannula assembly 300. The tissue-manipulating cannula assembly 300 may generally function in a manner similar to the tissue-manipulating cannula assembly 10. The tissue-manipulating cannula assembly 300 may include a first manipulating member 302 and a second manipulating member 304. The tissue-manipulating cannula assembly 300 may include a connection interface including a connection interface seat 306 and a connection interface post 308. The connection interface seat 306 may include a forward-facing opening, which may slip over the connection interface post 308 in a manner that facilitates assembly of the tissue-manipulating cannula assembly 300 in an anatomical cavity such as a nasal cavity.

Figure 23A:
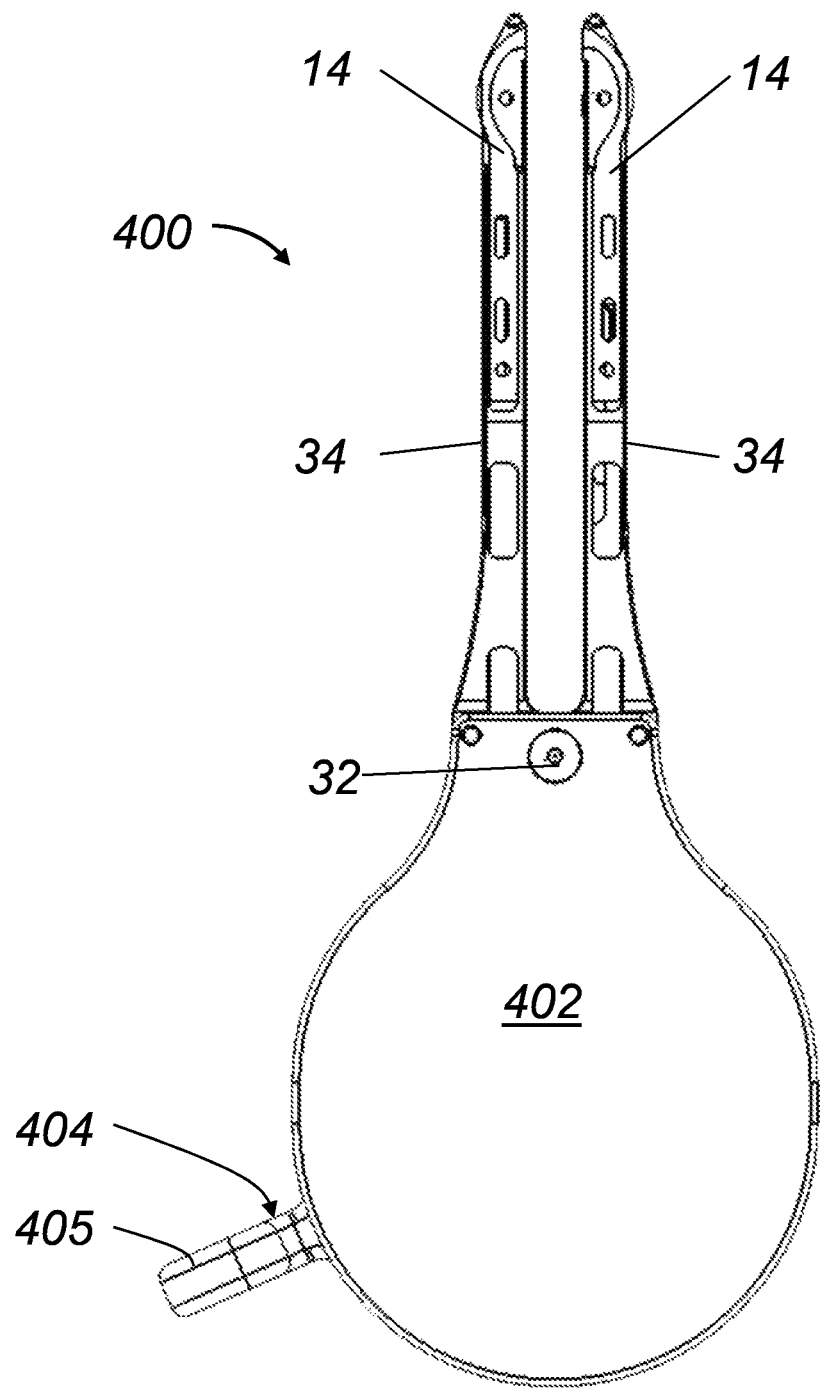
FIGS. 23A-23C are top views of another example suture activation assembly.
Figure 23B:
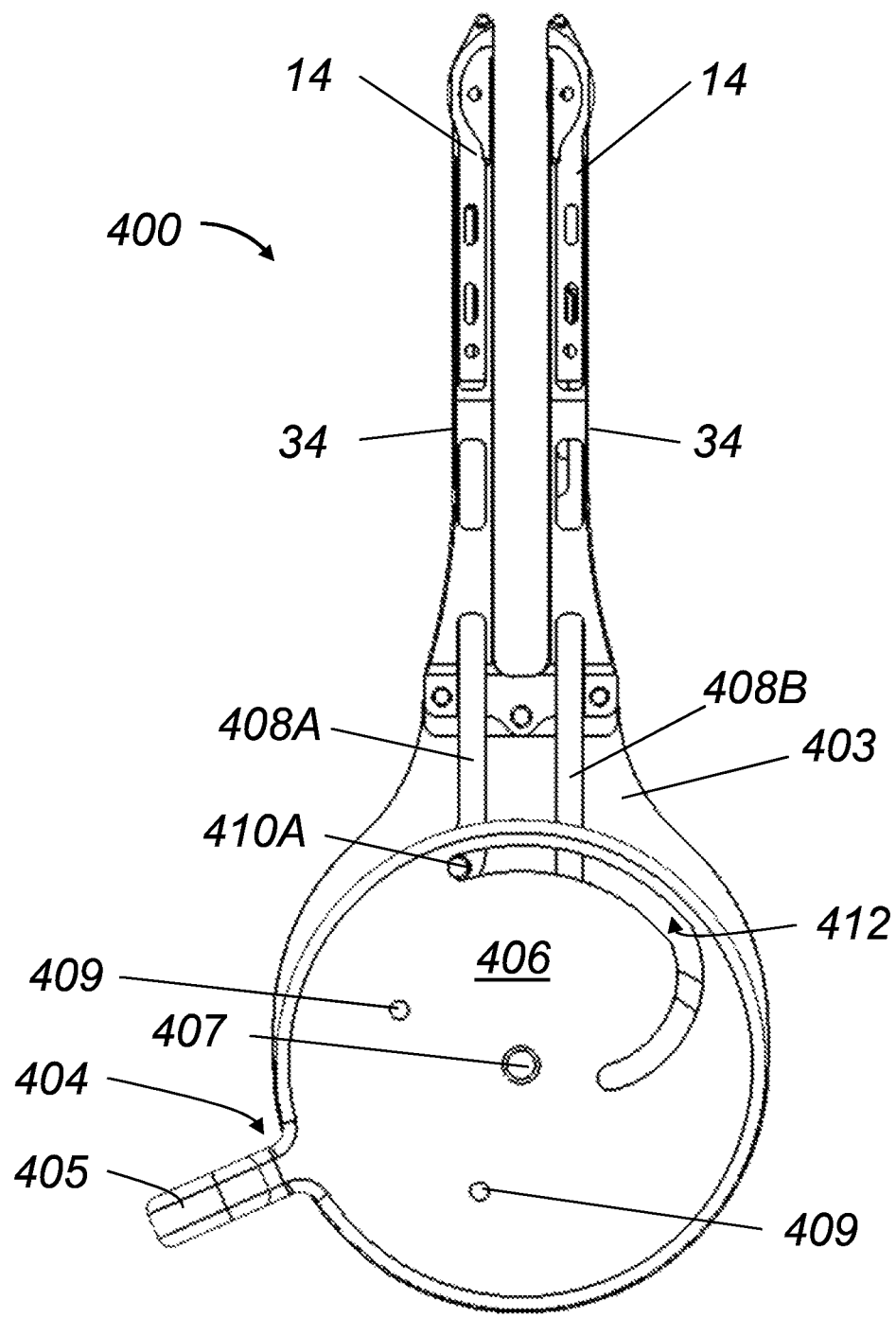
Figure 23C:
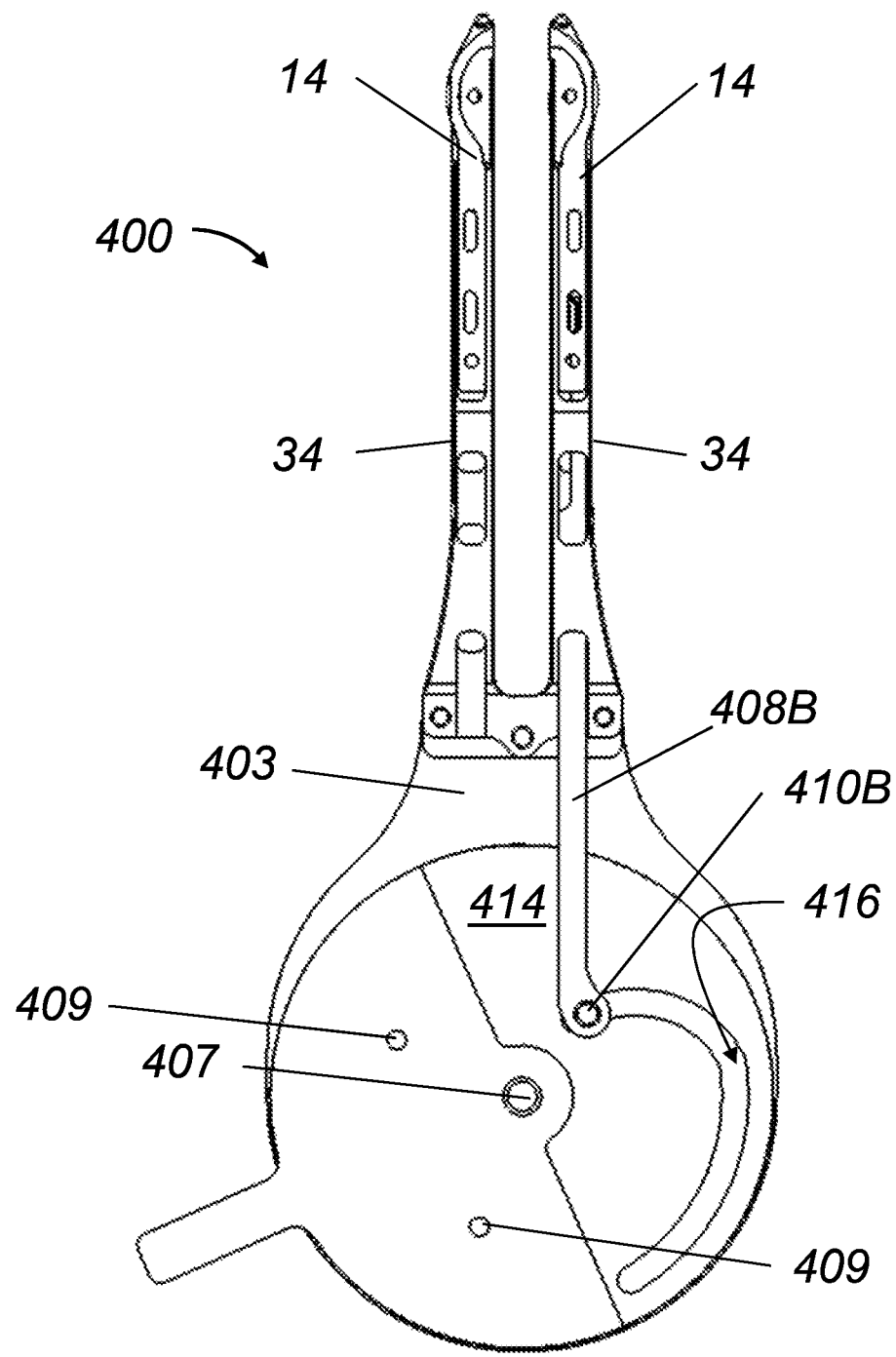

FIGS. 23A-23C are various top views of another example suture activation assembly 400. FIG. 23A is a top view of the suture activation assembly 400. FIG. 23B is top view of the suture activation assembly 400 with a superior housing 402 and the fastener 32 omitted. FIG. 23C is a top view of the suture activation assembly 400 with a top cam section 406 and a first driving member 408A omitted.

With combined reference to FIGS. 23A-23C, the suture activation assembly 400 may include a superior housing 402 and an inferior housing 403 connected by fasteners 32, welding, adhesive, or the like or any combination thereof. In some embodiments, the suture activation assembly 400 may not include a separate handle, but may be generally held by the superior housing 402 and/or the inferior housing 403 during use.

The superior housing 402 and the inferior housing 403 may house a top cam section 406 and a bottom cam section 414. The top cam section 406 and the bottom cam section 414 may be connected by fasteners 409, welding, adhesive, or the like or any combination thereof to collectively form a cam 404.

The cam 404 may include a projection 405 to allow a user to rotate the cam 404 about a shaft 407 positioned on the superior housing 402 and/or the inferior housing 403.

Rotating the cam 404 about the shaft 407 may urge a first driving member 408A and a second driving member 408B (collectively "driving members 408") to follow paths to actuate a suture needle between the suture application arms 34 in a manner similar to that described above.

In some embodiments, the first driving member 408A may include a projection 410A that extends into and interfaces with an opening 412 formed in the top cam section 406. As the cam 404 is rotated, the opening 412 may urge the projection 410A such that the first driving member 408A is linearly actuated.

The second driving member 408B may include a projection 410B that extends into and interfaces with an opening 416 formed in the bottom cam section 414. As the cam 404 is rotated, the opening 416 may urge the projection 410B such that the second driving member 408B is linearly actuated.

The openings 412 and 416 may be sized and shaped such that the driving members 408 are actuated relative to one another in a manner that actuates the suture needle in a manner similar to or the same as is described above.

In some embodiments, the suture activation assembly 400 may include disposable suture housing assemblies 14. Alternately, the suture activation assembly 400 may be entirely disposable such that the function of the suture housing assemblies may be non-removably included in the suture activation assembly 400.

Figure 24A:
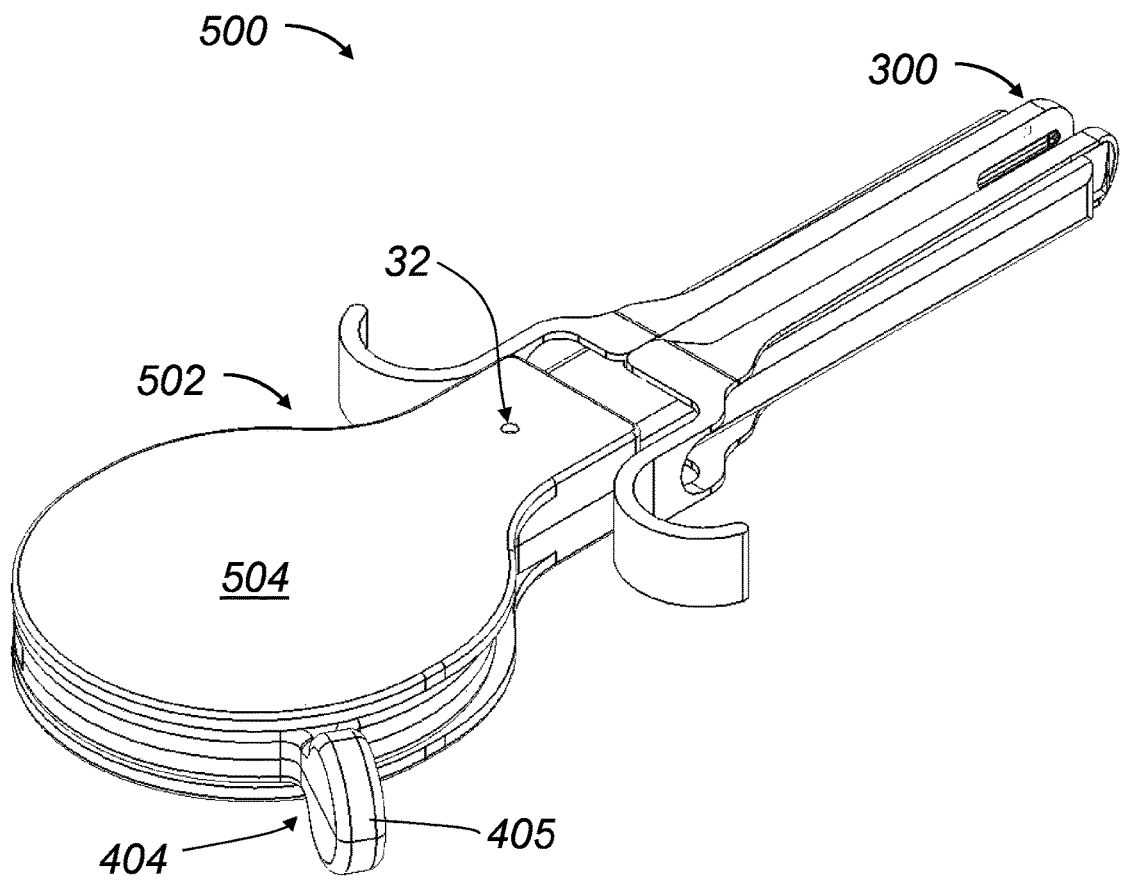
FIG. 24A is a perspective view of another example suturing device.
Figure 24B:
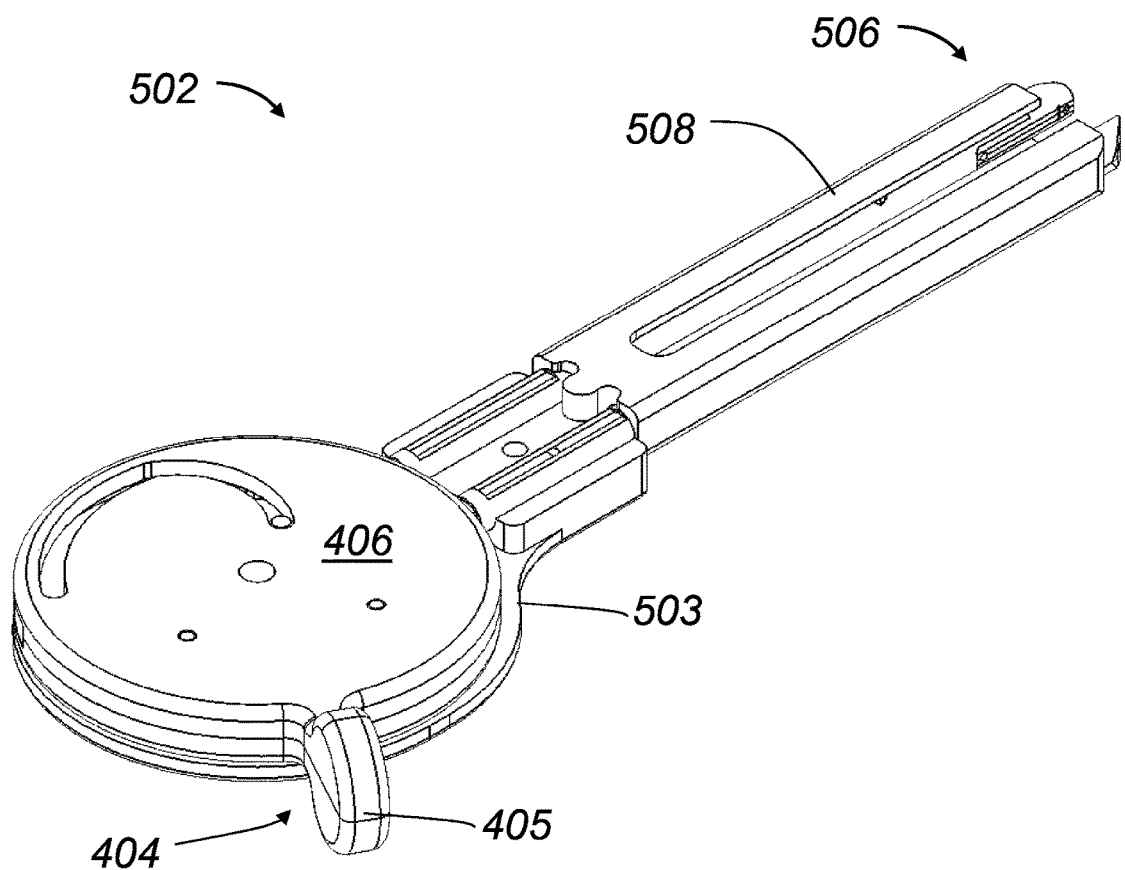
FIGS. 24B-24D are perspective views of a suture activation assembly of FIG. 24A.
Figure 24C:
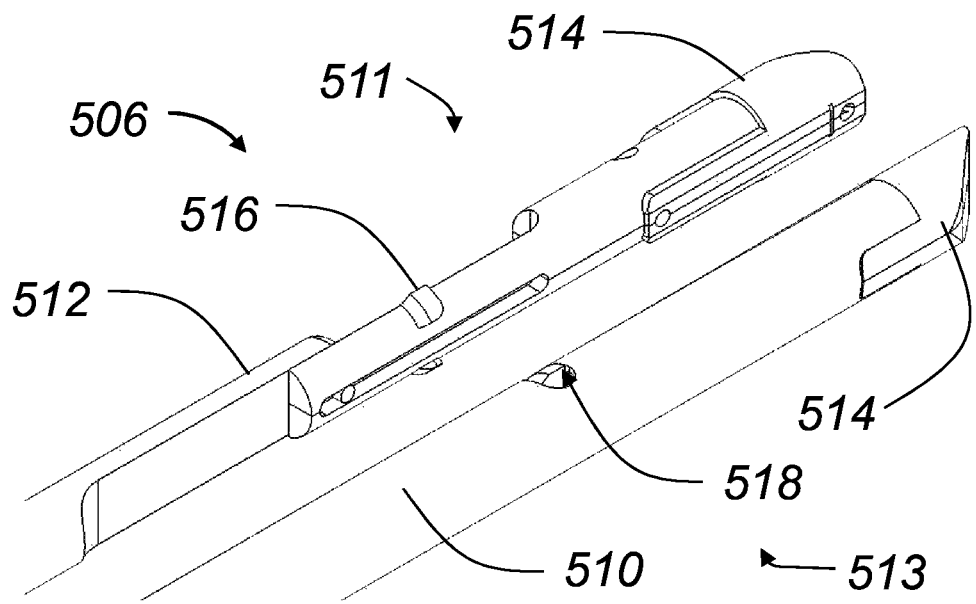
Figure 24D:
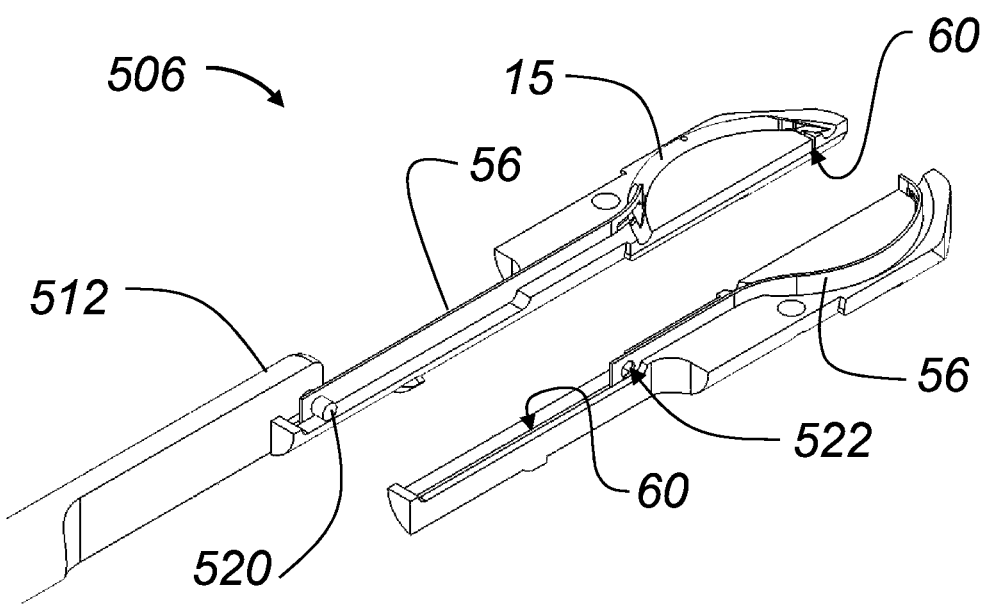

FIG. 24A is a perspective view of another example suturing device 500. FIG. 24B is a perspective view of a suture activation assembly 502 of the suturing device 500 with a superior housing 504 omitted. FIG. 24C is a detailed view of an end section 506 of the suture activation assembly 502 having various structures omitted. FIG. 24D is a detailed view of the end section 506 of the suture activation assembly 502 having various additional structures omitted.

With combined reference to FIGS. 24A-24D, the suturing device 500 may include the suture activation assembly 502 and the tissue-manipulating cannula assembly 300. The suture activation assembly 502 may be entirely disposable.

The suture activation assembly 502 may include a superior housing 504 and an inferior housing 503 connected by fasteners 32, welding, adhesive, or the like or any combination thereof. In some embodiments, the suture activation assembly 502 may not include a separate handle, but may be generally held by the superior housing 504 and/or the inferior housing 503 during use.

The suture activation assembly 502 may include an arm housing 508. The arm housing 508 may include a first arm 511 and a second arm 513, and each of the first 511 and second 513 arms may include a driving member 512 and a suture housing assembly 514 at least partially covered by a sheath 510. In some embodiments, the sheaths 510 may include openings 518 sized to receive protrusions 516 of the suture housing assemblies 514 to encourage a desired positioning of the suture housing assemblies 514.

As best seen in FIG. 24D, the driving members 512 may interface with the driving ribbons 56 by way of a protrusion received by a corresponding opening 522 of the driving ribbons 56.

Rotating the cam 404 in a first direction may actuate the driving members 512 such that the driving ribbons 56 are moved along the driving ribbon tracks 60 in a manner that moves the suture needle 15 from an enclosure in the first arm 511 into an enclosure in the second arm 513, as described in more detail above. Rotating the cam 404 in a second direction may actuate the driving members 512 such that the driving ribbons 56 are moved along the driving ribbon tracks 60 in a manner that moves the suture needle 15 from the enclosure in the second arm 513 into the enclosure in the first arm 511, as described in more detail above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture-passing system comprising:
   a suture passer including:
     a housing;
     a driving lever rotatably attached to the housing;
     a first arm attached to the housing, the first arm including a first needle track and a first driving ribbon;
     a second arm attached to the housing, the second arm including a second needle track and a second driving ribbon;
     a first driver attached to the first driving ribbon; and
     a second driver attached to the second driving ribbon;

a needle including a first notch configured to interface with the first driving ribbon and a second notch configured to interface with the second driving ribbon; and a cannula including:
- a first cannula member including a first suture-passing opening, and a first receiving aperture sized to receive the first arm of the suture passer; and
- a second cannula member including a second suture-passing opening, and a second receiving aperture sized to receive the second arm of the suture passer, wherein the first driving ribbon is configured to interface with the needle such that the needle is moved out of the first arm in response to the first driving ribbon being moved in a first direction.

2. The suture-passing system of claim 1, wherein the first cannula member and the second cannula member are selectively coupled via a connector.

3. The suture-passing system of claim 1, wherein the first cannula member includes a first handle and the second cannula member includes a second handle.

4. The suture-passing system of claim 1, wherein the first cannula member and the second cannula member are sized to fit within a human nasal cavity.

5. The suture-passing system of claim 1, wherein the first suture-passing opening and the second suture-passing opening include oblong shapes.

6. The suture-passing system of claim 1, wherein the first arm further includes a first driving ribbon track and the second arm further includes a second driving ribbon track.

7. The suture-passing system of claim 1, wherein the first needle track is sized to receive the entire needle within the first arm such that no portion of the needle extends out of the first arm, and the second needle track is sized to receive the entire needle within the second arm such that no portion of the needle extends out of the second arm.

8. The suture-passing system of claim 1, wherein the first driving ribbon is configured to interface with the needle such that the needle is moved into the first arm in response to the first driving ribbon being moved in a second direction.

9. The suture-passing system of claim 8, wherein the second driving ribbon is configured to interface with the needle such that the needle is moved into the second housing in response to the second driver being moved in the second direction.

10. The suture-passing system of claim 9, wherein the second driving ribbon is configured to interface with the needle such that the needle is moved out of the second housing in response to the second driver being moved in the first direction.

11. The suture-passing system of claim 1, wherein the driving lever includes a cam having a projection.

12. The suture-passing system of claim 11, wherein the cam includes an opening configured to linearly actuate the first driver and the second driver as the driving lever is rotated.

* * * * *